United States Patent [19]
Arnaout

[11] Patent Number: 5,877,275
[45] Date of Patent: Mar. 2, 1999

[54] CONTROLLING CELLULAR IMMUNE/INFLAMMATORY RESPONSES WITH β2 INTEGRINS

[75] Inventor: M. Amin Arnaout, Chestnut Hill, Mass.

[73] Assignee: The General Hospital Corporation, Boston, Mass.

[21] Appl. No.: 476,062

[22] Filed: Jun. 7, 1995

Related U.S. Application Data

[63] Continuation of Ser. No. 216,081, Mar. 21, 1994, abandoned, which is a continuation of Ser. No. 637,830, Jan. 4, 1991, abandoned, which is a continuation-in-part of Ser. No. 539,842, Jun. 18, 1990, abandoned, which is a continuation-in-part of Ser. No. 212,573, Jun. 28, 1988, abandoned.

[51] Int. Cl.$^6$ .................................................. C07K 14/705
[52] U.S. Cl. ........................................... 530/324; 530/350
[58] Field of Search ...................... 530/300, 350, 530/324; 514/12, 13, 14, 15, 16, 17

[56] References Cited

U.S. PATENT DOCUMENTS

| | | | |
|---|---|---|---|
| 4,840,793 | 6/1989 | Todd, III et al. | 424/153.1 |
| 5,114,842 | 5/1992 | Plow et al. | 424/1.49 |

FOREIGN PATENT DOCUMENTS

| | | | |
|---|---|---|---|
| 0 364 690 | 4/1990 | European Pat. Off. . | |
| US91/04338 | 8/1991 | WIPO . | |

OTHER PUBLICATIONS

Arnaout et al., Blood 75:1037–1190.
Dana et al., J. Clin. Invest. 73:153–159 1984.
Arnaout et al., J. Clin. Invest. 74:1291–1300 1984.
Dana et al., The Journal of Immunology, vol. 137, No. 10, pp. 3259–3263, Nov. 15, 1986.
Mehra et al., Proc. Natl. Acad. Sci., USA, vol. 83, pp. 7013–7017, Sep. 1986.
Kishimoto et al., Cell, vol. 48, pp. 681–690, Feb. 27, 1987.
Pytela, The Embo Journal, vol. 7, No. 5, pp. 1371–1378, 1988.
Corbi et al., The Journal of Biological Chemistry, vol. 263, No. 25, pp. 12403–12411, Sep. 5, 1988.
Arnaout et al., New Eng. J. Med. 321:457 1985.
Todd et al., J. Clin. Invest. 74:1280 1984.
Arnaout et al., J. Clin. Invest. 72:171 1983.
Wallis et al., J. Immunol. 135:2323 1985.
Beatty et al., J. Immunol. 131:2913 1983.
Law et al., EMBO J. 6:915 1987.
Todd et al., Hybridoma 1:329 1982.
Hickstein et al., Proc. Nat'l. Acad. Sci. USA 86:275 1989.
Larson et al., J. Cell. Biol. 108:703 1989.
Cosgrove et al. Proc. Nat'l. Acad. Sci. USA 83:752 1986.
Sastre et al. Proc. Nat'l. Acad. Sci. USA 83:5644 1986.
Hutchings et al., Mature 348:639 1990.
Carlos et al., Immunol. Rev. 114:5, 1990.
Pierce et al., Biochem. Biophys. ACTA 874:368 1986.
Arnaout et al., J. Clin. Invest. 85:977 1990.
Ruoslahti et al., Science 238:491 1987.
Hynes et al., Cell 48:549 1987.
Bowie et al. 1990. Science 247: 1306–1310.
Miller, et al, 1987, "Purification and ∝subunit N–terminal suquences of . . . " J. Immunol. 138:2381–83.
Tamkun, et al., 1986, "Structure of integrin, a glycoprotein involved in . . . " Cell vol. 46:271–282.
Arnaout, et al., 1988, J. Cell Biol. 106: 2153–2158.
Corbi, et al., 1987, EMBO Journal vol. 6: 4023–4028.
Simpson, et al., 1988, J. Clin. Invest. 81: 624–628.
Vedder, et al., 1988, J. Clin. Invest. 81:939–944.

*Primary Examiner*—Stephen Walsh
*Assistant Examiner*—Karen E. Brown
*Attorney, Agent, or Firm*—Fish & Richardson P.C.

[57] ABSTRACT

The invention features human CD11 recombinant or synthetic peptide capable of inhibiting a CD11/CD18-mediated immune response, a purified DNA encoding a human CD11b peptide, soluble heterodimeric molecules composed of a CD11 peptide and a CD18 peptide, and a method of controlling any phagocyte-mediated tissue damage such as that associated with reduced perfusion of heart tissue during acute cardiac insufficiency.

4 Claims, 17 Drawing Sheets

```
                        TGGCTTCCTTGTGGTTCCTCAGTGGTGCCTGCAACCCCTGGTTCACCTCCTTCC
AGGTTCTGGCTCCTTCCAGCCATGGCTCTCAGAGTCCTTCTGTTAACAGCCTTGACCTTATGTCATGGG
                        M   A   L   R   V   L   L   L   T   A   L   T   L   C   H   G         -1
TTCAACTTGGACACTGAAAACGCAATGACCTTCCAAGAGAACGCAAGGGGCTTCGGGCAGAGCGTGGTC
 F   N   L   D   T   E   N   A   M   T   F   Q   E   N   A   R   G   F   G   Q   S   V   V    23
CAGCTTCAGGGATCCAGGGTGGTGGTTGGAGCCCCCCAGGAGATAGTGGCTGCCAACCAAAGGGGCAGC
 Q   L   Q   G   S   R   V   V   V   G   A   P   Q   E   I   V   A   A   N   Q   R   G   S    46
CTCTACCAGTGCGACTACAGCACAGGCTCATGCGAGCCCATCCGCCTGCAGGTCCCCGTGGAGGCCGTG
 L   Y   Q   C   D   Y   S   T   G   S   C   E   P   I   R   L   Q   V   P   V   E   A   V    69
AACATGTCCCTGGGCCTGTCCCTGGCAGCCACCACCAGCCCCCCTCAGCTGCTGGCCTGTGGTCCCACC
 N   M   S   L   G   L   S   L   A   A   T   T   S   P   P   Q   L   L   A   C   G   P   T    92
GTGCACCAGACTTGCAGTGAGAACACGTATGTGAAAGGGCTCTGCTTCCTGTTTGGATCCAACCTACGG
 V   H   Q   T   C   S   E   N   T   Y   V   K   G   L   C   F   L   F   G   S   N   L   R   115
CAGCAGCCCCAGAAGTTCCCAGAGGCCCTCCGAGGGTGTCCTCAAGAGGATAGTGACATTGCCTTCTTG
 Q   Q   P   Q   K   F   P   E   A   L   R   G   C   P   Q   E   D   S   D   I   A   F   L   138
ATTGATGGCTCTGGTAGCATCATCCCACATGACTTTCGGCGGATGAAGGAGTTTGTCTCAACTGTGATG
 I   D   G   S   G   S   I   I   P   H   D   F   R   R   M   K   E   F   V   S   T   V   M   161
GAGCAATTAAAAAAGTCCAAAACCTTGTTCTCTTTGATGCAGTACTCTGAAGAATTCCGGATTCACTTT
 E   Q   L   K   K   S   K   T   L   F   S   L   M   Q   Y   S   E   E   F   R   I   H   F   184
ACCTTCAAAGAGTTCCAGAACAACCCTAACCCAAGATCACTGGTGAAGCCAATAACGCAGCTGCTTGGG
 T   F   K   E   F   Q   N   N   P   N   P   R   S   L   V   K   P   I   T   Q   L   L   G   207
CGGACACACACGGCCACGGGCATCCGCAAAGTGGTACGAGAGCTGTTTAACATCACCAACGGAGCCCGA
 R   T   H   T   A   T   G   I   R   K   V   V   R   E   L   F   N   I   T   N   G   A   R   230
AAGAATGCCTTTAAGATCCTAGTTGTCATCACGGATGGAGAAAAGTTTGGCGATCCCTTGGGATATGAG
 K   N   A   F   K   I   L   V   V   I   T   D   G   E   K   F   G   D   P   L   G   Y   E   253
GATGTCATCCCTGAGGCAGACAGAGAGGGAGTCATTCGCTACGTCATTGGGGTGGGAGATGCCTTCCGC
 D   V   I   P   E   A   D   R   E   G   V   I   R   Y   V   I   G   V   G   D   A   F   R   276
AGTGAGAAATCCCGCCAAGAGCTTAATACCATCGCATCCAAGCCGCCTCGTGATCACGTGTTCCAGGTG
 S   E   K   S   R   Q   E   L   N   T   I   A   S   K   P   P   R   D   H   V   F   Q   V   299
AATAACTTTGAGGCTCTGAAGACCATTCAGAACCAGCTTCGGGAGAAGATCTTTGCGATCGAGGGTACT
 N   N   F   E   A   L   K   T   I   Q   N   Q   L   R   E   K   I   F   A   I   E   G   T   322
CAGACAGGAAGTAGCAGCTCCTTTGAGCATGAGATGTCTCAGGAAGGCTTCAGCGCTGCCATCACCTCT
 Q   T   G   S   S   S   F   E   H   E   M   S   Q   E   G   F   S   A   A   I   T   S       345
AATGGCCCCTTGCTGAGCACTGTGGGGAGCTATGACTGGGCTGGTGGAGTCTTTCTATATACATCAAAG
 N   G   P   L   L   S   T   V   G   S   Y   D   W   A   G   G   V   F   L   Y   T   S   K   368
GAGAAAAGCACCTTCATCAACATGACCAGAGTGGATTCAGACATGAATGATGCTTACTTGGGTTATGCT
 E   K   S   T   F   I   N   M   T   R   V   D   S   D   M   N   D   A   Y   L   G   Y   A   391
GCCGCCATCATCTTACGGAACCGGGTGCAAAGCCTGGTTCTGGGGCACCTCGATATCAGCACATCGGC
 A   A   I   I   L   R   N   R   V   Q   S   L   V   L   G   A   P   R   Y   Q   H   I   G   414
CTGGTAGCGATGTTCAGGCAGAACACTGGCATGTGGGAGTCCAACGCTAATGTCAAGGGCACCCAGATC
 L   V   A   M   F   R   Q   N   T   G   M   W   E   S   N   A   N   V   K   G   T   Q   I   437
GGCGCCTACTTCGGGGCCTCCCTCTGCTCCGTGGACGTGGACAGCAACGGCAGCACCGACCTGGTCCTC
 G   A   Y   F   G   A   S   L   C   S   V   D   V   D   S   N   G   S   T   D   L   V   L   460
ATCGGGGCCCCCCATTACTACGAGCAGACCCGAGGGGGCCAGGTGTCCGTGTGCCCCTTGCCCAGGGGG
 I   G   A   P   H   Y   Y   E   Q   T   R   G   G   Q   V   S   V   C   P   L   P   R   G   483
AGGGCTCGGTGGCAGTGTGATGCTGTTCTCTACGGGGAGCAGGGCCAACCCTGGGGCCGCTTTGGGGCA
 R   A   R   W   Q   C   D   A   V   L   Y   G   E   Q   G   Q   P   W   G   R   F   G   A   506
GCCCTAACAGTGCTGGGGGACGTAAATGGGGACAAGCTGACGGACGTGGCCATTGGGCCCCAGGAGAG
 A   L   T   V   L   G   D   V   N   G   D   K   L   T   D   V   A   I   G   A   P   G   E   529
GAGGACAACCGGGGTGCTGTTTACCTGTTTCACGGAACCTCAGGATCTGGCATCAGCCCCTCCCATAGC
 E   D   N   R   G   A   V   Y   L   F   H   G   T   S   G   S   G   I   S   P   S   H   S   552
CAGCGGATAGCAGGCTCCAAGCTCTCTCCCAGGCTCCAGTATTTTGGTCAGTCACTGAGTGGGGGCCAG
 Q   R   I   A   G   S   K   L   S   P   R   L   Q   Y   F   G   Q   S   L   S   G   G   Q   575
GACCTCACAATGGATGGACTGGTAGACCTGACTGTAGGAGCCCAGGGGCACGTGCTGCTGCTCAGGTCC
 D   L   T   M   D   G   L   V   D   L   T   V   G   A   Q   G   H   V   L   L   L   R   S   598
CAGCCAGTACTGAGAGTCAAGGCAATCATGGAGTTCAATCCCAGGGAAGTGGCAAGGAATGTATTTGAG
 Q   P   V   L   R   V   K   A   I   M   E   F   N   P   R   E   V   A   R   N   V   F   E   621
TGTAATGATCAAGTGGTGAAAGGCAAGGAAGCCGGAGAGGTCAGAGTCTGCCTCCATGTCCAGAAGAGC
 C   N   D   Q   V   V   K   G   K   E   A   G   E   V   R   V   C   L   H   V   Q   K   S   644
ACACGGGATCGGCTAAGAGAAGGACAGATCCAGAGTGTTGTGACTTATGACCTGGCTCTGGACTCCGGC
 T   R   D   R   L   R   E   G   Q   I   Q   S   V   V   T   Y   D   L   A   L   D   S   G   667
CGCCCACATTCCCGCGCCGTCTTCAATGAGACAAAGAACAGCACACGCAGACAGACACAGGTCTTGGGG
 R   P   H   S   R   A   V   F   N   E   T   K   N   S   T   R   R   Q   T   Q   V   L   G   690
CTGACCCAGACTTGTGAGACCCTGAAACTACAGTTGCCGAATTGCATCGAGGACCCAGTGAGCCCCATT
 L   T   Q   T   C   E   T   L   K   L   Q   L   P   N   C   I   E   D   P   V   S   P   I   713
```

FIG. 1A

```
GTGCTGCGCCTGAACTTCTCTCTGGTGGGAACGCCATTGTCTGCTTTCGGGAACCTCCGGCCAGTGCTG
 V  L  R  L  N  F  S  L  V  G  T  P  L  S  A  F  G  N  L  R  P  V  L       736
GCGGAGGATGCTCAGAGACTCTTCACAGCCTTGTTTCCCTTTGAGAAGAATTGTGGCAATGACAACATC
 A  E  D  A  Q  R  L  F  T  A  L  F  P  F  E  K  N  C  G  N  D  N  I       759
TGCCAGGATGACCTCAGCATCACCTTCAGTTTCATGAGCCTGGACTGCCTCGTGGTGGGTGGGCCCCGG
 C  Q  D  D  L  S  I  T  F  S  F  M  S  L  D  C  L  V  V  G  P  R          782
GAGTCTAACGTGACAGTGACTGTGAGAAATGATGGTGAGGACTCCTACAGGACACAGGTCACCTTCTTC
 E  S  N  V  T  V  T  V  R  N  D  G  E  D  S  Y  R  T  Q  V  T  F  F       805
TTCCCGCTTGACCTGTCCTACCGGAAGGTGTCCACACTCCAGAACCAGCGCTCACAGCGATCCTGGCGC
 F  P  L  D  L  S  Y  R  K  V  S  T  L  Q  N  Q  R  S  Q  R  S  W  R       828
CTGGCCTGTGAGTCTGCCTCCTCCACCGAAGTGTCTGGGGCCTTGAAGAGCACCAGCTGCAGCATAAAC
 L  A  C  E  S  A  S  S  T  E  V  S  G  A  L  K  S  T  S  C  S  I  N       851
CACCCCATCTTCCCGGAAAACTCAGAGGTCACCTTTAATATCACGTTTGATGTAGACTCTAAGGCTTCC
 H  P  I  F  P  E  N  S  E  V  T  F  N  I  T  F  D  V  D  S  K  A  S       874
CTTGGAAACAAACTGCTCCTCAAGGCCAATGTGACCAGTGAGAACAACATGCCCAGAACCAACAAAACC
 L  G  N  K  L  L  L  K  A  N  V  T  S  E  N  N  M  P  R  T  N  K  T       897
GAATTCCAACTGGAGCTGCCGGTGAAATATGCTGTCTACATGGTGGTCACCAGCCATGGGGTCTCCACT
 E  F  Q  L  E  L  P  V  K  Y  A  V  Y  M  V  V  T  S  H  G  V  S  T       920
AAATATCTCAACTTCACGGCCTCAGAGAATACCAGTCGGGTCATGCAGCATCAATATCAGGTCAGCAAC
 K  Y  L  N  F  T  A  S  E  N  T  S  R  V  M  Q  H  Q  Y  Q  V  S  N       943
CTGGGGCAGAGGAGCCCCCCCATCAGCCTGGTGTTCTTGGTGCCCGTCCGGCTGAACCAGACTGTCATA
 L  G  Q  R  S  P  P  I  S  L  V  F  L  V  P  V  R  L  N  Q  T  V  I       966
TGGGACCGCCCCCAGGTCACCTTCTCCGAGAACCTCTCGAGTACGTGCCACACCAAGGAGCGCTTGCCC
 W  D  R  P  Q  V  T  F  S  E  N  L  S  S  T  C  H  T  K  E  R  L  P       989
TCTCACTCCGACTTTCTGGCTGAGCTTCGGAAGGCCCCCGTGGTGAACTGCTCCATCGCTGTCTGCCAG
 S  H  S  D  F  L  A  E  L  R  K  A  P  V  V  N  C  S  I  A  V  C  Q      1012
AGAATCCAGTGTGACATCCCGTTCTTTGGCATCCAGGAAGAATTCAATGCTACCCTCAAAGGCAACCTC
 R  I  Q  C  D  I  P  F  F  G  I  Q  E  E  F  N  A  T  L  K  G  N  L      1035
TCGTTTGACTGGTACATCAAGACCTCGCATAACCACCTCCTGATCGTGAGCACAGCTGAGATCTTGTTT
 S  F  D  W  Y  I  K  T  S  H  N  H  L  L  I  V  S  T  A  E  I  L  F      1058
AACGATTCCGTGTTCACCCTGCTGCCGGGACAGGGGGCGTTTGTGAGGTCCCAGACGGAGACCAAAGTG
 N  D  S  V  F  T  L  L  P  G  Q  G  A  F  V  R  S  Q  T  E  T  K  V      1081
GAGCCGTTCGAGGTCCCCAACCCCCTGCCGCTCATCGTGGGCAGCTCTGTCGGGGGACTGCTGCTCCTG
 E  P  F  E  V  P  N  P  L  P  L  I  V  G  S  S  V  G  G  L  L  L  L      1104
GCCCTCATCACCGCCGCGCTGTACAAGCTCGGCTTCTTCAAGCGGCAATACAAGGACATGATGAGTGAA
 A  L  I  T  A  A  L  Y  K  L  G  F  F  K  R  Q  Y  K  D  M  M  S  E      1127
GGGGGTCCCCCGGGGGCCGAACCCCAGTAG
 G  G  P  P  G  A  E  P  Q  *                                             1136
(SEQ ID NO:40)
```

FIG. 1B

```
                                    GAATTCCCTCTTTCACCCTGTCTAGGT
     ATG AAG GAT TCC TGC ATC ACT GTG ATG GCC ATG GCG CTG CTG TCT GGG TTC TTT TTC TTC
 13   M   K   D   S   C   I   T   V   M   A   M   A   L   L   S   G   F   F   F   F

CCA CCG CGC GCC GGG AGG CAC TTT GGA TAC CGC GTC CTG CTG CAG AAC GGG GGA GTC ATC
 50   P   P   R   A   G   R   H   F   G   Y   R   V   L   L   Q   N   G   G   V   I

TCG GGC ACA GGA CAC TGC CTG CCA GTC ACG CTG AAC ACC TAT TAT AGT TCC TCC TGT TAC CTC
 87   S   G   T   G   H   C   L   P   V   T   L   N   T   Y   Y   S   A   S   C   Y   L

GAC CCT GGG CTG TCT CGA ACG TGT GAC CAG GTA GAC TAT GGC ATG TCG AGC TTG CAG
124   D   P   G   L   S   R   T   C   D   Q   V   D   Y   G   M   S   S   L   Q

GAA TGT ATC AAG GGC AAC GTA TAC CAG TTT CTG TTT GCT CCA ACA AGC TAC AAA ACA GAA
161   E   C   I   K   G   N   V   Y   Q   F   L   F   A   T   S   Y   K   T   E

CTC AGC AAC ACT TCG ATG CAC TTG CTG CAG GTT ACC AAT GAT AGT ATC AAT TAT GTC GCG ACA
198   L   S   N   T   S   M   H   L   L   Q   V   T   N   D   S   I   N   Y   V   A   T

CAT GTA AAG CAC ATG GAT GAT TTT AAA GCC TCA AAA CCC GCG AGC GAG TTT GTG AAA GAC ATC
235   H   V   K   H   M   D   D   F   K   A   S   K   P   A   S   E   F   V   K   D   I

ATC ATC ACG CTC CAC CAT GCA CAG GAC CTG ACT GAC CTG TTC TCC AAG CTG TCC TCC AGC GGC
272   I   I   T   L   H   H   A   Q   D   L   T   D   L   F   S   K   L   S   S   S   G

GAG ACC CTC CAC ACA GGG GAT CTT CGG ATC GAG GAG CAG CTG GCA GAT GCC ACA TTT ATT
309   E   T   L   H   T   G   D   L   R   I   E   E   Q   L   A   D   A   T   F   I

ATT GAG GGC TGG ACA GAG CAT GGG CAA ACT CAT GAG CAG GAC TCG GCC TCT TAT ATC CGA TAC
346   I   E   G   W   T   E   H   G   Q   T   H   E   Q   D   S   A   S   Y   I   R   Y

AAG GAC TGG CTG ACC ACC CCC TCC ACA ATC GAG GAG CAG ACT CTG AAG ACT TCG CAG GCC ACA TTT
383   K   D   W   L   T   T   P   S   T   I   E   E   Q   T   L   K   T   S   Q   A   T   F

GTG ACC CTG CAG GTC TTC TAT CTG CAG CAG CAT GGG GAG GAG CAG GTG TTG CTG ATT GGC CGG GTG TAC
420   V   T   L   Q   V   F   Y   L   Q   Q   H   G   E   E   Q   V   L   L   I   G   R   V   Y

TGG AGC CAG CTG TAT GGG GAG GGT AGA CAG GGA ACT CAG CGG ATT GGC CCT GGG GAG CAG
457   W   S   Q   L   Y   G   E   G   R   Q   G   T   Q   R   I   G   P   G   E   Q

GCC CCA CTG TTC TAT GAG GAG ATC ACT CTG AAC GCC ACA GAC ATC TAC ATC GAT GGG GTA GAC
494   A   P   L   F   Y   E   E   I   T   L   N   A   T   D   I   Y   I   D   G   L   V   D

GGG CGG TTT GGA GAA GCC ATC ACA CTG GCT AAC GAC ATC AAC GGC GAT GGG CTG GTA GAC
     G   R   F   G   E   A   I   T   L   A   N   D   I   N   G   D   G   L   V   D
```

FIG. 6A

```
TGCCAGCAAATCCCACGGGCCTCCTGACGCTGCCCCTGGGCCACAGTCCCTCGAGTGCTGGAAGG                                    94

GCG CCG GCC TCG AGC TAC AAC CTG GAC GTG CGG GGC GCG CGG AGC TTC TCC              205
 A   P   A   S   S   Y   N   L   D   V   R   G   A   R   S   F   S

GTG GGA GCT CCA GGG GAG GCT CCA AAC GGG ACA AGC CTC TAT CAG TGC CAG              316
 V   G   A   P   G   E   A   P   N   G   T   S   L   Y   Q   C   Q

TTG GGA ACC TTG GCA ACA GAC GAC CCC ACA GAT GGA AGC ATT TTG GCC TGT              427
 L   G   M   T   L   A   T   D   D   P   T   D   G   S   I   L   A   C

TTC CGC CAG AAT CTG CAG GGT CCC ATG CTG CAG GGG CGC CCT GGT TTT CAG              538
 F   R   Q   N   L   Q   G   P   M   L   Q   G   R   P   G   F   Q

CCA GAT GAA TTT CAG AAA ATT CTG GAC TTC ATG AAG GAT GTG ATG AAG AAA              649
 P   D   E   F   Q   K   I   L   D   F   M   K   D   V   M   K   K

TTT GAT TTC TCA GAT TAT GTT GTT AAA TGG GCC CGG CAT GAG GCT GCT CTG AAG          760
 F   D   F   S   D   Y   V   V   K   W   A   D   H   E   A   A   L   K

GAG GTG TTC CGG GAG GAG CTG ATT GGA GCC AAG CAT CCA GAT GCC ACC AAA              871
 E   V   F   R   E   E   L   I   G   A   K   H   P   D   A   T   K

ATC CGC TAC ATC ATC GGG ATT CTA TTC ACT GAG CTG CAG CAG AAG AAG ATC TAT GTC      982
 I   R   Y   I   I   G   I   L   F   T   E   L   Q   Q   K   K   I   Y   V

TTT GAG AAG CTG GAC GAC AGG CCA TTC CAT GCA GTC GCA AGA GGC GCA GTA GGA GCC     1093
 F   E   K   L   D   D   R   P   F   H   A   V   A   R   G   A   V   G   A

ATC AGT GCT GAC CTC AGC ACA CCA TTG CTG CTG CAA GAA GAG CCA CTG TAT TTG GGT TAC ACC     1204
 I   S   A   D   L   S   T   P   L   L   L   Q   E   E   P   L   Y   L   G   Y   T

GGG AAT GAA ATG GAA GTG CGA GTC GAC TTC TTC GGG GGT ACA GAG CCA GAG ACA GGA GGA CAC     1315
 G   N   E   M   E   V   R   V   D   F   F   G   G   T   E   P   E   T   G   G   H

CAG CAC ATG GTC GAC GTG GAT GAT CAA CAA GAT GGG CAG CTG CTG CCC GAC TAC CCA GGC CAC    1426
 Q   H   M   V   D   V   D   D   Q   Q   D   G   Q   L   L   P   D   Y   P   G   H

TGT GGC GTC GAC CGA GTG CTG CTG GAT GAC CAG TCA GAG GAG CAG GGG GGG CTG ATT GGT        1537
 C   G   V   D   R   V   L   L   D   D   Q   S   E   E   Q   G   G   L   I   G

TTG GGG TTT GAA GAA GTC TCA TCA GAG GAG CTG CAG CAG CAG GAG CAG GAC TAC CCA CTC        1648
 L   G   F   E   E   V   S   S   E   E   L   Q   Q   Q   E   Q   D   Y   P   L

GTG GCT GTG GGG GCC CCT CTG GAG GAG CAG GCT GTG TAC ATC TTC AAT                        1759
 V   A   V   G   A   P   L   E   E   Q   A   V   Y   I   F   N
```

| Pos | Codons and amino acids |
|---|---|
| 531 | GGG AGG CAC GGG GGG CTT AGT CCC CAG CCA AGT CAG CGG ATA GAA GGG ACC CAA GTG CTC<br>G   R   H   G   G   L   S   P   Q   P   S   Q   R   I   E   G   T   Q   V   L |
| 568 | GGG GAT GGC CTG GAA GTG GAT GTG GCT GTG TAT TCA ACC GCT GAG ATC GTG AGC TCC<br>G   D   G   L   E   V   D   V   A   V   Y   S   T   A   E   I   V   S   S |
| 605 | CCA GTG CAT GAA AAT CTC TGC TCC TAC ACT GAG ATG ATG AAA GAA GGA AGA CGG GTT<br>P   V   H   E   N   L   C   S   Y   T   E   M   M   K   E   G   R   R   V |
| 642 | CTG GTT GCC AAT CTC TAC ACT CTG CAG TAT ACT CTG CAG ATG AAG CAC ACC CAA ATC TCC<br>L   V   A   N   L   Y   T   L   Q   Y   T   L   Q   M   K   H   T   Q   I   S |
| 679 | AGC ATG TCA TGC ACT GAC TTC TCA CAT TTT CAG GAT GGC CAC TGT GTT CCC CCG CAC TCG<br>S   M   S   C   T   D   F   S   H   F   Q   D   G   H   C   V   P   P   H   S |
| 716 | AGG AGG AGG GCG CAG GGC GGG AAG GAC ATA ATA TCA ACC CCG CCC AGA CCC CTG CTG<br>R   R   R   A   Q   G   G   K   D   I   I   S   T   P   P   R   P   L   L |
| 753 | GAG GCA AAC TTG AGA CTG TCC TTC TCT GCA CCG GCA AGA GCC TTC TCC ATC TTC AAA GCA<br>E   A   N   L   R   L   S   F   S   A   P   A   R   A   F   S   I   F   K   A |
| 790 | TAC TGG AGA CTC TCC TTC CAC TTA TCT AAT GTG GGA TCT CCC AAT TTC CCC ATC TTT AAA GCA G<br>Y   W   R   L   S   F   H   L   S   N   V   G   S   P   N   F   P   I   F   K   A |
| 827 | TCC AGG CTT CTG TCC AGG GCA TTA GCC AAT GTG ACC TGT TCA AAA TTC CCC AAA CTC CTG<br>S   R   L   L   S   R   A   L   A   N   V   T   C   S   K   F   P   K   L   L |
| 864 | GGG GAC GTT GAA TTG CAC GAC GCC TCC ACA GTC TAT GTC GAC GAG GAC CCC CCC GGA GCC CTC<br>G   D   V   E   L   H   D   A   S   T   V   Y   V   D   E   D   P   P   G   A   L |
| 901 | CTC ATC CAG GAC CAA CCC ACC GAA GAA CTG GAT GCT GAG GCC CGG CAG CTC TGC AGC TCC<br>L   I   Q   D   Q   P   T   E   E   L   D   A   E   A   R   Q   L   C   S   S |
| 938 | GAC CAC AAC ATA CCC ACC AGG AGG CTC GAT GAT TCC ATG CTC TGT CCC GGA GCC TAC TAC<br>D   H   N   I   P   T   R   R   L   D   D   S   M   L   C   P   G   A   Y   Y |
| 975 | TAT GAG GAT CTG CTG GAG TTG ATG AAG CAG CAG GGT GAT GAT GAG CAG GAG GGG TTC<br>Y   E   D   L   L   E   L   M   K   Q   Q   G   D   D   E   Q   E   G   F |
| 1012 | CTG GAG CTG GTG GTG GAG CTC CTG ATC GAC AGC AGC AGG AGG AGC CTG TCC CTC TCC<br>L   E   L   V   V   E   L   L   I   D   S   S   R   R   S   L   S   L   S |
| 1049 | CTG GCC CAG GTT GTC ATG AAG GTT GAC GTG CAG ATG CTC TAC CTC TAC<br>L   A   Q   V   V   M   K   V   D   V   Q   M   L   Y   L   Y |

| | | | | | | | | | | | | |
|---|---|---|---|---|---|---|---|---|---|---|---|---|
| TCA S | GGA G | ATT I | CAG Q | TGG W | TTT F | GGA G | CGC R | TCC S | ATC I | CAT H | GGG G | GTG V | AAG K | GAC D | CTT L | GAA E | 1870 |
| CGG R | CCC P | GTG V | GAT D | ATG M | TTC F | CAG Q | ACC T | AAG K | CTG L | ATG M | TCC S | TTC F | TCT S | CCA P | GCT A | GAG L | ATC I | 1981 |
| ATC I | ACA T | ATC I | TGT C | TTC F | CAG Q | AGA R | CAT H | AAT N | TTT F | GAG E | ATA I | ATG M | CTC L | TAC Y | CAG Q | TTC F | CAA Q | GGC G | CGC R | 2092 |
| TTG L | TTC F | CCA P | GGA G | GGG G | TCC S | CTG L | AAT N | TTT F | GAG E | GTG V | ATG M | ACC T | CTC L | AGA R | AGG R | ATA I | GCT A | ACC T | 2203 |
| CCC P | ATC I | AAT N | GTT V | TCC S | CTG L | CCT P | GAG E | ATA I | ATG M | ATC I | CTC L | TCT S | CTT L | AAG K | CAG Q | ACA T | CCG P | 2314 |
| GAA E | ACC T | TGG W | GAG E | GAG E | CCT P | GTG V | TCT S | AGC S | CTG L | ATA I | TAC Y | AAC N | TTT F | GAG E | GGG G | ACA T | 2425 |
| TTT F | GCC A | AGC S | CTC L | TCT S | GTG V | AGC S | CTG L | GTG V | TTT F | ATC I | CAG Q | TGT C | AGT S | AAC N | TTG L | AAG K | TGT C | 2536 |
| CTG L | AAG K | CCC P | CAT H | GCT A | CTG L | CTG L | CAG Q | ATG M | TAC Y | ATC I | AAT N | ACA T | TGC C | GAA E | GAT D | GCT A | 2647 |
| CAC H | TCG S | AGC S | GTT V | GCC A | AAG K | CAG Q | CTG L | ATG M | ATC I | TAC Y | ATC I | CCC P | ATC

```
1086  CTG TAC AAG GTT GGT TTC TTC AAA CGG AAC CTG AAG GAG AAG ATG GAG GCT GGC AGA GGT
       L   Y   K   V   G   F   F   K   R   N   L   K   E   K   M   E   A   G   R   G

1123  GAG GCT GGG GAT CCC GGC TGC CTG AAG CCC CTC CAT GAG AAG GAC TCT GAG AGT GGT GGT
       E   A   G   D   P   G   C   L   K   P   L   H   E   K   D   S   E   S   G   G

CCACTTCGCCTCTGCCTGCATTCTGCCGTGTGCCCTCGGGCGAGTCACTGCCTCTCCCTGGCCCTCAGTTTCCCTATC
      AAGAGGGCTGCAAAAGTGCCTCAAGTGAGGGCTTGTCATTACCAGACGGTTCACCAGCCTCTCTCTTGGTTCCTTCCTTGAAGAGAAT
      GATGTCCACAGATGCCTCCAGCAACTGTCCTTGCACTCCCCTGCACTGGAGTCCAGTCTCTTCTGCTGG
      TCCTTGGCATGCCTTCCAGCACCTGCAAATGAGAACCCTCGTGGCCTTCTTCTAGAGCCGTGATGCCT
      CAGACAGCTCCCTCTGCCTGAACCTTCGCCCACATCTCGCCTTCCTTGACCAGCAGATCCCAGCTCACGTCACA
      TTTCTTCATCCGGCAGCCTGACATAATTTCACTGAATTAATGACAGAGCTACTTAGCAGCTACTATCTCTCAGTGAACTGT
      CTAGTAGGTGCTTGACATAATTTCACTGAATTAATGACAGAGCCAGTGGGAAGATACAGAAAAAGAGGGCCGGGGCTG
      AGTTAGAGAGGCCAGCCTGGCGAAACCCATCTCTACTAAAATACAAAATCCAGGCGTGGTGGCACACACCTGTAGTCC
      TGCGCCATTGCACTCCAGCCTGGGCAACACAGCGAGACTCCGTCTCAAGGAAAAATAAAAATAAAAGCGGGCACGG
      AGGACCCATCACGCCCTGTGCAGTGCCCCCCACAGAAAGACTGAGCTCAAGGTGGGAACCACGTCTGCTAACTTGGAGC

FIG. 6E
```

```
GTC CCG AAT GGA ATC CCT GCA GAA GAC TCT GAG CAG CTG GCA TCT GGG CAA   3535
 V   P   N   G   I   P   A   E   D   S   E   Q   L   A   S   G   Q

GGC AAG GAC TGAGTCCAGCCTGTGAGGTGCAGAGTGCCCAGAACTGGACTCAGGATGCCCAGGG  3659
 G   K   D

TCGAACATGGAACTCATTCCTGAATGTCTCCTTTGCAGGCTCATAGGGAAGACCTGCTGAGGGACCAGCC   3807
GTCTGATCTAAATGTGGAGAAACTGTAGTCTCAGAGACCTAGGGATGTTCTGGCCCTCACCCCTGCCCTGG  3955
CAGAAAGCAAATGTGACCTGTCACTACGGTGTCACACGCCCTTGTTCTTGGCCACAGACCAAAT         4103
CCCTGTTGAAGCTCTGGTGACACCAGCCTTTCTCCCAGGCCACCCTGCCACTACTCCCTGTCTTCCTGCATTCACC  4251
CACTTGGTTGGGTCCTCACATCTTTCTGTTCACCTTGACACCTCCCTGACGCCGCATGACGCCGCATGAGATATGTCAGGGCGTGGGACAT  4399
GAGGGTAAAGGCTATACTTGTCTTGTTCACCTGGATGACGCCGATGATATGTCAGGGCGTGGGACAT       4547
GGCGCGGTGGTTCACGCCTGTAATCCCAGCACTTTGGGAGGCCAAGGAGGGTGGATCACCTGAGGTCAGG    4695
CAGCTACTCAGGAGGTTGAGGTAGGAGAATTGCTTGAACCTGGAGGTTGCAGTGAGCCAAGAT          4843
GCCCGGACATCCCCACCCTTGGAGGCTGTCTTCTCAGGCTCTGCCCTGCCCTAGCTCCACACCCTCTCCC    4991
CCCAGTGCCAAGCACAGTGCCTGCATGTATTTATCCAATAAATGTGAAATTCTGTCCAAAAAAAAAAAA     5138

(SEQ ID NO:39)
```

FIG. 6F

| FIG. 7A | FIG. 7B |

FIG. 7

```
GAATTCCTGCCACTCTTCCTGCAACGGCCCAGGAGCTCCAGAGCTTCTAGTCATGACCAGGAC
CTTCCGGTGTGACAGCGCTGGGTTTGGAGACAGCGTGGTCCAGTATGCCAACTCCTGGGTGGTTGGAGCCCC
CGGCCTGCAGGTGCCCCCGGAGGCCGTGAACATGTCCCCTGGGCCTGTCCCTGGCGTCTACCAGCCCTTCCA
GGGCCCCACCCAGTCACCCAGAGGCTCCCCAGTTCTGATGCAGTTCCTGATGCAGTTCTCCAACAGCAGGAGCAGGACATTGTGTT
CCAGTTCCAGAGACACCCAGACCCAGTTTCCTGCACCGATTGTTCCATGCCTCATATGGGCCCGTAGGGATGCCACCAAAATTCT
AGGCATCATCCGCTATGCCAATTGGGGTTGGATTAGCTTTCAAAACAGAAATTCTTGGAAAGAATTAAATGACAT
GAAGGAGAAGATCTTTGCCATTGAGGGTACGGAGACCACCAAGCAGTAGCTCCTTCGAATTGGAGATGGCACAGGA
CTTCCTGTACCCCCAAATATGAGCCCTACCTTCATCAACATGTCTCAGGAGAATGTGGACAATGAGGGACTCTTA
CACCGGAAGGCTGTCATCTTCACCCCAGTGTCCAGGATGAAGGCCAAGTCACGGGACTCAGAT
GGCCCCCATTACTACGAGCAGACCCGAGGGGCCAGGTGCCAGGTTCTGTGTCCCTTGCCCAGGGGTGGAGAAGGTG
GGATGTGAATGGGACAAGCTGACAGACGTGGTCATCGGGGCCCCAGGAGAGAACCGGGGTGCTGCTA
CAGGCTGCAGTATTTGGGCAGGCACTGAGCGGGGTCAAGACCTCACCCAGGATGGACTGGTGGACCTGCTGT
TGCCGAGATCCCCAGGTCTGCGTTTGAGTGTCGGGAGCAGGTGGTCTCTCAGGAAACAAGAACCGGAGTCTGAGCCGAGTCCG
GGCCCCTGACCCTGGCCGTCAGTCCCCGTGAGTCCCTGGCAAGCCCTATCCAAAACCTGCAGAAACCTGCCCTATGCTGGC
CATTACCTTGCGTCTGAACTTCACGCTTCCCAGGCTTGAAGTCCCTGTGGGAGTAACCTGGAGCTGAACGCAGA
CAATCTCGGCATCTCCTTCAGCTTCCAGGGGCCAGAAACAAGGCAGCTGCCTCCCTGCACCGGAGACCGGCCCCAGTTGG
CCGCTACGTGGCAGAGGGCCAGAAACAAGGCCAGCTGTCCTGGGAGACCGGCTGTCCTGACATGTGACAGTGAGAA
GGCTACCTTTGACGTCTCCCCCAAGCGTCTCCCCCAAATACCTCAACTTCTCACCCCCAGAGGAGCCATGTGGCCATGCACAG
CAGCACGAACAATTCACCACCAAATCACCAACTTCTCACCCCAGAGGAGCCATCCCTTCGGTGCTCCTCAGAGAAATGC
GGAGGCTGTGTGACGTGTCCCCTCCTTCAGCGTCCAGGAGTCTGAGCCTGAGCTGATTTCACCCTGAAAGGGCAACCTCAGCTTTGG
GTTCCGCTGTGACGTCCCCTCCTTCAGCGTCCAGGAGAGCTGATTTCACCCTGAAGGGCAACCTCAGCTTTGG
CTCCCAGCTTCCAGGACAGGAGCATTATGACAAGAGGAACCTCAGACGACAACGGTGCTGGAGAAGTACAAGTCCACAA
AGTTGGCTTCTTCAAGCCTCAGTACAAGGTCAGTGGCTCAGGCTGACTTGCAATTGCAATGGACAAATTGCCCCAGAAACGGAC
ACTTACCCTCACCTGTCAGGCTGTGTTCCCCAAAAGGACTTGACTTGCAATTTCTACCTAGAAATACATGGACAATACCCCAGGC
GGGTCCCTGCTGTGTTCCCCAAAAGGACTTGACTTGCAATTTCTACCTAGAAATACATGGACAATACCCCAGGC
TTTTTTTTGAGACGGAGTCTCGCTCTGTCACCCAGGCTGGAGTGCAATGGCGTGATCTCGGCTGATCTCGGCTCTGCAACCT
CCGGCCCGATCTTTCTAAATACAGTTCTGAAATATGCTGCTCATCCCCACCTGTCTTCAACACGTCTCCCATTACC
ACAGCATGAGAGCCTCTGTGCCCCATCACCCTCGTTTCCAGTGAATTAGTGTCATGTCAGCATCAGCTCAGGGC
GCTGGCTCCCGGTTGGTCAACATTGCCTGGCCTGGAAGGAGGAGCGCCCTCTAGGAGGAGGACATGCCCCG
TACCTGAAAAATGCCAAGCACTAGATTATTTTTAAAAGCGTACTTTAAATGTTTGTGTTAATACACATTAA
GTGGAAAAAAAAAAAAAAAAAAAAAAAAAAAAAAAAA
```

FIG. 7A

```
CAGGGCCAGCAGCACTCCTCCTCTGTTCACAGCCTTAGCAACTTCTCTAGTTTCAACTTGGACACAGAGAGCTGACAGC    150
CCAAAGATAACAGCTGCCAACCAAACGGGTGGCCTCTACCAGTGTGGCTACAGCACTGTGCCTGTGCCTGAGCCCAT    300
GCTGCTGGCCTGCGGCCCCACCGTGCACAAGCGTGCGGGAGGAACATGTACCTCACCGGACTCTGCTTCCTCCT    450
CCTGATCGATGGCCTCAGGGCTCAGGCGCACGTCAAACCCCCTCAGCCTGTTGCCTTCGTGCCACGATGATGAACTTCGTGAGAGCTGTGATAAG    600
GGAATTCAGGCGCACGTCAAACCCCCTCAGCCTGTTGCCTTCGTGCCACGATGATGAACTTCGTGAGAGCTGTGATAAG    750
CATTGTCATCAGCACTGATGGGAAGAAGAAGGCGACAGCCTGATTATAAGGATGTCATCCCCATGGCTGATGCAGC    900
TGCATCGAAGCCCTCCAGGAACACATATTTAAAGTGGAGGACTTTGATGCTCTGAAAGATATTCAAAACCAACT    1050
GGGCTTCAGCGCTGTGTTCACACCTGGCCCCCTGATGGCCCCCTTGGGGCTGGTCTTCGGGGAGCTTCACCTGGTCTGGAGGTGC    1200
CCTGGGTTACTCCACCGAGCTGCCTCCTCTGCTCCGTGGACGTAGACACCGGCAGACACCGACCTGTCCTCATCGG    1350
CGGCTCCTACTTCGGGGCTGTTCTCTACGGGGAGCAGGGCCACCCCTGGGGTCGCTTTGGGCGGCTCTGACAGTGCTGGG    1500
GTGGTGTGATGCTGTTCACGGAGTCTTGGGACCTCAGCCCAGCATCAGCCCTGCTCCTGAGACCTGTGCTCTGGGTGGGGTGAGCAGTTCATACC    1650
CCTGTTTCACGGGGGCCCAGGTGCTCCTGCTCAGGACCCTGCAGAACCTGCTTGGGACCGTGCTCCCCGAGCTGCGTGGAGGACTCTGTGACCCT    1800
GGGGGGCCCAGGTGCTCCTGCTCAGGACCCTGCAGAACCTGCTTGGGACCGTGCTCCCCGAGCTGCGTGGAGGACTCTGTGACCCT    1950
CTGCCTTTACATTGACAAAGTTCTAAGAACCTGTGAAAACTTCAACCTGCCTCCCTACCCTTGAGAAGAACTGTGGAGCCGACCATATCGCCAGGA    2100
AGTCCTCGGGCTGAAGGCACACTGTCACGGGCTTCACGGCCCCTACCCTTGAGAAGAACTGTGGAGCCGACCATATCGCCAGGA    2250
CGCACTGGCTCAGAGATACTTCACGGGCTGAAGGCACACTGTCACGGGCTTCACGGCCCCTACCCTTGAGAAGAACTGTGGAGCCGACCATATCGCCAGGA    2400
AGTGATGGTGTGAATGACGGGAAGACTGAGAGCCAGCTGCTGAGGACCAAGAGACCAGCAGAGGACTGGGACAGAGGACAGAGGACTGGGACAGAGGACTGGGTGCCTGTGCCTGTGCCTGT    2550
GAGCCAGGCACCTGAGAATGACGGGAAGACTGAGAGCCAGCTGCTGAGGACCAAGAGACCAGCAGAGGACTGGGACAGAGGACTGGGTGCCTGTGCCTGT    2700
CAACACTCCCAGACTCCCAGGACCAAGACGTTCTGACAACTGGAGACAGAGGACCTGGGACAGAGGACTGGGTGCCTGTGCCTGT    2850
ATACCAGTCAATAACTGGACTTCCTGGCGCACATTCAGAAGAATCCGTGCTGGACTCAGAATTACGTTCGACACATCCGTGTA    3000
ACCCCAGCATCTGACTTCCTGGCGCACATTCAGAAGAATCCGTGCTGGACTCAGAATTACGTTCGACACATCCGTGTA    3150
CTGGGTCCGCCAGATATTGCAGAAGAAGAGTGTCGGTCGTGAGTGTGCTGCTGGACTCAGAATTACGTTCGACACATCCGTGTA    3300
CCCCACCCCTCATGGTAGGCAGCTCCATTGGGGGTCGTGTTGCTGCTGGACTTCTTCCCGCGATTTCCCCACTT    3450
ACAGACCCCCAGCCCCAGTGAGAAATGATCCCTTCTTCTTCTTCCCCGCGATTTCCCCACTT    3600
GTCTTTGGGAGAAAACGTCTTGCTTGGGAAGGGGCCTTGTCTGTCTTCCTTTTCTTTTTCTTTTTTCTTTTTTTT    3750
CTCAGTCTCCCTTCTCCCATGAGGCACGAATGATCTTTCTCAGCCTCTGCGTGAAGTTCCCCTCGAGAAGTTCCATCCAGAGGTGGGCTTCAGGGCGC    3900
CGGCCTCCCGGGTTCAAGTAATTCTGTCTTCGCGTGAAGTTCCCCTCGAGAAGTTCCATCCAGAGGTGGGCTTCAGGGCGC    4050
CTCAGGACAATGTCTGAACTCTCCAGTTCCGATTCCCAGGGCAGAAGACCAACCACTTCCTATTTTTGAGGCTATGAATATAG    4200
TTCATCGTGGGCTCAGCTCCAGTTCCAGTTCCGATTCCCAGGGCAGAAGACCAACCACTTCCTATTTTTGAGGCTATGAATATAG    4350
GTGCGGCTGCAGCTCACCAGCCCCAGGGCAGAAGACCAACCACTTCCTATTTTTGAGGCTATGAATATAG    4500
AACATCGCACAAAAACGATGCATCTACCGCTCCTCCTTGGGAAATAATCTGAAAGGTCTAAAATAAAAAGCCTTCT    4650
                                                                                4704

(SEQ ID NO:52)
```

FIG. 7B

```
CTCGCCCTGG TGGGGCTGCT CTCCCTCGGG TGCGTCCTCT CTCAGGAGTG CACGAAGTTC   60
AAGGTCAGCA GCTGCCGGGA ATGCATCGAG TCGGGCCCG  GCTGCACCTG GTGCCAGAAG  120
CTGAACTTCA CAGGGCCGGG GGATCCTGAC TCCATTCGCT GCGACACCCG GCCACAGCTG  180
CTCATGAGGG GCTGTGCGGC TGACGACATC ATGGACCCCA CAAGCCTCGC TGAAACCCAG  240
GAAGACCACA ATGGGGGCCA GAAGCAGCTG TCCCCACAAA AAGTGACGCT TTACCTGCGA  300
CCAGGCCAGG CAGCAGCGTT CAACGTGACC TTCCGGCGGG CCAAGGGCTA CCCCATCGAC  360
CTGTACTATC TGATGGACCT CTCCTACTCC ATGCTTGATG ACCTCAGGAA TGTCAAGAAG  420
CTAGGTGGCG ACCTGCTCCG GGCCCTCAAC GAGATCACCG AGTCCGGCCG CATTGGCTTC  480
GGGTCCTTCG TGGACAAGAC CGTGCTGCCG TTCGTGAACA CGCACCCTGA TAAGCTGCGA  540
AACCCATGCC CCAACAAGGA GAAAGAGTGC CAGCCCCCGT TTGCCTTCAG GCACGTGCTG  600
AAGCTGACCA ACAACTCCAA CCAGTTTCAG ACCGAGGTCG GGAAGCAGCT GATTTCCGGA  660
AACCTGGATG CACCCGAGGG TGGGCTGGAC GCCATGATGC AGGTCGCCGC CTGCCCGGAG  720
GAAATCGGCT GGCGCAACGT CACGCGGCTG CTGGTGTTTG CCACTGATGA CGGCTTCCAT  780
TTCGCGGGCG ACGGAAAGCT GGGCGCCATC CTGACCCCCA ACGACGGCCG CTGTCACCTG  840
GAGGACAACT TGTACAAGAG GAGCAACGAA TTCGACTACC CATCGGTGGG CCAGCTGGCG  900
CACAAGCTGG CTGAAAACAA CATCCAGCCC ATCTTCGCGG TGACCAGTAG GATGGTGAAG  960
ACCTACGAGA AACTCACCGA GATCATCCCC AAGTCAGCCG TGGGGGAGCT GTCTGAGGAC 1020
TCCAGCAATG TGGTCCATCT CATTAAGAAT GCTTACAATA AACTCTCCTC AGGGTCTTC  1080
CTGGATCACA ACGCCCTCCC CGACACCCTG AAAGTCACCT ACGACTCCTT CTGCAGCAAT 1140
GGAGTGACGC ACAGGAACCA GCCCAGAGGT GACTGTGATG GCGTGCAGAT CAATGTCCCG 1200
ATCACCTTCC AGGTGAAGGT CACGGCCACA GAGTGCATCC AGGAGCAGTC GTTTGTCATC 1260
CGGGCGCTGG GCTTCACGGA CATAGTGACC GTGCAGGTCC TTCCCCAGTG TGAGTGCCGG 1320
TGCCGGGACC AGAGCAGAGA CCGCAGCCTC TGCCATGGCA AGGGCTTCTT GGAGTGCGGC 1380
ATCTGCAGGT GTGACACTGG CTACATTGGG AAAAACTGTG AGTGCCAGAC ACAGGGCCGG 1440
AGCAGCCAGG AGCTGGAAGG AAGCTGCCGG AAGGACAACA ACTCCATCAT CTGCTCAGGG 1500
CTGGGGGACT GTGTCTGCGG GCAGTGCCTG TGCCACACCA GCGACGTCCC CGGCAAGCTG 1560
ATATACGGGC AGTACTGCGA GTGTGACACC ATCAACTGTG AGCGCTACAA CGGCCAGGTC 1620
TGCGGCGGCC CGGGGAGGGG GCTCTGCTTC TGCGGGAAGT GCCGCTGCCA CCCGGGCTTT 1680
GAGGGCTCAG CGTGCCAGTG CGAGAGGACC ACTGAGGGCT GCCTGAACCC GCGGCGTGTT 1740
GAGTGTAGTG GTCGTGGCCG GTGCCGCTGC AACGTATGCG AGTGCCATTC AGGCTACCAG 1800
CTGCCTCTGT GCCAGGAGTG CCCCGGCTGC CCCTCACCCT GTGGCAAGTA CATCTCCTGC 1860
GCCGAGTGCC TGAAGTTCGA AAAGGGCCCC TTTGGGAAGA ACTGCAGCGC GGCGTGTCCG 1920
GGCCTGCAGC TGTCAACAA  CCCCGTGAAG GGCAGGACCT GCAAGGAGAG GGACTCAGAG 1980
GGCTGCTGGG TGGCCTACAC GCTGGAGCAG CAGGACGGGA TGGACCGCTA CCTCATCTAT 2040
GTGGATGAGA GCCGAGAGTG TGTGGCAGGC CCCAACATCG CCGCCATCGT CGGGGGCACC 2100
GTGGCAGGCA TCGTGCTGAT CGGCATTCTC CTGCTGGTCA TCTGGAAGGC TCTGATCCAC 2160
CTGAGCGACC TCCGGGAGTA CAGGCGCTTT GAGAAGGAGA AGCTCAAGTC CCAGTGGAAC 2220
AATGATAATC CCCTTTTCAA GAGCGCCACC ACGACGGTCA TGAACCCCAA GTTTGCTGAG 2280
AGTTAGGAGC A                                                      2291
```

(SEQ ID NO:53)

FIG. 8

CONTROLLING CELLULAR IMMUNE/ INFLAMMATORY RESPONSES WITH β2 INTEGRINS

This is a continuation of application Ser. No. 08/216,081 filed Mar. 21, 1994, now abandoned; which is a continuation of application Ser. No. 07/637,830, filed Jan. 4, 1991, now abandoned; which is a continuation-in-part of application Ser. No. 07/539,842, filed Jun. 18, 1990, now abandoned; which is a continuation-in-part of application Ser. No. 07/212,573, filed Jun. 28, 1988, now abandoned.

This invention, at least in part, was funded by a grant from the United States Government and the Government has certain rights in the invention.

BACKGROUND OF THE INVENTION

This invention relates to controlling cellular immune/ inflammatory responses, particularly phagocyte-mediated tissue injury and inflammation.

Circulating phagocytic white blood cells are an important component of the cellular acute inflammatory response. It is believed that a number of important biological functions such as chemotaxis, immune adherence (homotypic cell adhesion or aggregation), adhesion to endothelium, phagocytosis, antibody-dependent cellular cytotoxicity, superoxide, and lysosomal enzyme release are mediated by a family of leukocyte surface glycoprotein adhesion receptors known as $\beta_2$ integrins or the CD11/CD18 complex. Arnaout et al., *Blood* 75:1037 (1990). Inherited deficiency of CD11/CD18 impairs leukocyte adhesion-dependent inflammatory functions and predisposes to life-threatening bacterial infections. Dana et al., *J. Clin. Invest.* 73:153 (1983); Arnaout et al., *J. Clin. Invest.* 74:1291 (1984).

The CD11/CD18 family consists of three heterodimeric surface glycoproteins, each with a distinct α subunit (CD11a, CD11b or CD11c) non-covalently associated with a common β subunit (CD18). The divalent cations $Ca^{+2}$ and $Mg^{2+}$ are essential in the stabilization and function of the αβ (CD11/CD18) complex.

The β2 integrins are expressed only on leukocytes. While CD11a/CD18 (also known as LFA-1, TA-1) is expressed on all leukocytes, CD11b/CD18 and CD11c/CD18 (also known as LeuM5 or p150,95) are expressed primarily on monocytes, polymorphonuclear leukocytes, macrophages and natural killer cells CD11c/CD18 is also expressed on certain lymphocytes. Arnaout, *Blood* 75:1037 (1990).

CD11a/CD18, and not CD11b/CD18 or CD11c/CD18, is expressed on B- and T-lymphocytes; accordingly CD11a/ CD18 plays a role in mitogen-, antigen-, and alloantigen- induced proliferation, T-cell-mediated cytotoxicity, lymphocyte aggregation, and Ig production. In contrast, all three CD11/CD18 molecules are important for monocyte/ macrophage and granulocyte adhesion-dependent functions.

It is believed that CD11b/CD18 and CD11c/CD18 mediate enhanced adhesiveness of activated phagocytes through quantitative and qualitative changes in these proteins on the surface of activated cells. For example, in granulocytes, these proteins are translocated from intracellular storage pools present in secondary and tertiary granules. Arnaout et al., *J. Clin. Invest.* 74:1291 (1984); Arnaout et al., *New Eng. J. Med.* 312:457 (1985); Todd et al., *J. Clin. Invest.* 74:1280 (1984).

CD11b/CD18 is also known as complement receptor type 3 (CR3), Mol, Mac-1 or MAM. See, Arnaout et al., *J. Clin. Invest.* 72:171 (1983), and references cited therein; Dana et al., *J. Immunol.* 137:3259 (1986); Wallis et al., *J. Immunol.* 135:2323 (1985); Arnaout et al., *New Eng. J. Med.* 312:457 (1985); Dana et al., *J. Clin. Invest.* 73:153 (1984); and Beatty et al., *J. Immunol.* 131:2913 (1983). Like all β2 integrins, CD11b/CD18 consists of two non-covalently associated subunits. Kishimoto et al., *Cell* 48:681 (1987); Law et al., *EMBO J.* 6:915 (1987); Arnaout et al. *J. Clin. Invest.* 72:171 (1983). The α subunit of CD11b/CD18 has an apparent molecular mass of 155–165 kD and associates non-covalently with a β subunit, CD18, of apparent molecular mass 95 kD. Todd et al., *Hybridoma* 1:329 (1982).

Monoclonal antibodies have been used to identify at least two distinct functional domains of CD11b/CD18, one mediating homotypic and heterotypic adhesion and the other mediating binding to the complement C3 fragment (iC3b), the major C3 opsonin in vivo. Dana et al., *J. Immunol.* 137:3259 (1986).

Law et al., *EMBO J.* 6:915 (1987) and Kishimoto et al., *Cell* 48:681 (1987) disclose the nucleotide sequence of human CD18. Arnaout et al., *J. Cell Biol.* 106:2153 (1988); Corbi et al., *J. Biol. Chem.* 263:12403 (1988); and Hickstein et al., *Proc. Nat'l. Acad. Sci. USA* 86:275 (1989) disclose the nucleotide sequence of human CD11b. Larson et al., *J. Cell. Biol.* 108:703 (1989) disclose the nucleotide sequence of CD11a. Corbi et al., *EMBO J.* 6:4023 (1987) disclose the nucleotide sequence of CD11c.

Cosgrove et al. (*Proc. Nat'l. Acad. Sci. USA* 83:752, 1986) report a human genomic clone which produces "a molecule(s)" reactive with monoclonal antibodies to CD11b.

Sastre et al. (*Proc. Nat'l. Acad. Sci. USA* 83:5644, 1986) report a mouse genomic clone coding for an amino-terminal partial exon of murine CD11b. Pytela et al., *EMBO J.* 7:1371 (1988) report a cDNA sequence of murine CD11b.

Simpson et al., *J. Clin. Invest.* 81:624 (1988) disclose that a monoclonal antibody (904) directed to an adhesion-promoting domain of CD11b (Dana et al., *J. Immunol.* 137:3259, 1986) reduces the extent of cardiac damage in dogs associated with myocardial infarction, presumably by limiting reperfusion injury. Vedder et al. (*J. Clin. Invest.* 81:939, 1988) similarly found that a monoclonal antibody directed against CD18 subunit of CD11b/CD18 reduced organ injury and improved survival from hemorrhagic shock in rabbits. In animal models, anti-CD11/CD18 antibodies have been shown to have protective effects in shock, frostbite, burns, cerebral edema, onset of diabetes mellitus (Hutchings et al., *Nature* 348:639, 1990) and transplant rejection. Reviewed in Carlos et al., *Immunol. Rev.* 114:5 (1990).

SUMMARY OF THE INVENTION

The peptides and heterodimeric proteins of the invention are capable of antagonizing CD11/CD18 (β2 integrin) mediated immune response. CD11/CD18 mediated immune responses which it may be desirable to block include acute inflammatory functions mediated by neutrophils. The molecules of the invention are useful for treatment of ischemia reperfusion injury (e.g., in the heart, brain, skin, liver or gastrointestinal tract), burns, frostbite, acute arthritis, asthema, and adult respiratory distress syndrome. Peptides and heterodimeric proteins of the invention may also be useful for blocking intra-islet infiltration of macrophages associated with insulin-dependent diabetes mellitus.

The invention features a purified peptide which includes at least one extracellular region of a β2 integrin subunit capable of inhibiting a CD11/CD18 mediated immune response, the peptide lacks the transmembrane and cytoplasmic portions of the β2 integrin subunit. In a preferred embodiment the β2 integrin subunit is a human β2 integrin subunit; more preferably the β2 integrin subunit is CD11a, CD11b, CD11c or CD18; most preferably the β2 integrin subunit is CD11b. Preferably, the peptide includes all or part of the A domain of CD11b. More preferably the peptide includes one of the following sequences: DIAFLIDGS (SEQ ID NO: 32); FRRMKEFVS (SEQ ID NO: 33); FKILVVITDGE (SEQ ID NO: 34); VIRYVIGVGDA (SEQ ID NO: 35); DGEKFGDPLG (SEQ ID NO: 36); YEDVIPEADR (SEQ ID NO: 37); DGEKFGDPLGYEDVIPEADR (SEQ ID NO: 17); NAFKILVVITDGEKFGDPLGYEDVIPEADREGV (SEQ ID NO: 50); DGEKF (SEQ ID NO: 51). In preferred embodiments, the peptide includes the amino acid sequence YYEQTRGGQVSVCPLPRGRARWQCDAV (SEQ ID NO: 38); the peptide includes the amino acid sequence KSTRDRLR (SEQ ID NO: 15). Preferably, the peptide includes one of the following amino acid sequences: AYFGASLCSVDVDSNGSTDLVLIGAP (SEQ ID NO: 1); GRFGAALTVLGDVNGDKLTDVAIGAP (SEQ ID NO: 2); QYFGQSLSGGQDLTMDGLVDLTVGAQ (SEQ ID NO: 3); YEQTRGGQVSVCPLPRGRARWQCDAV (SEQ ID NO: 4); DIAFLIDGSGSIIPHDFRRMK (SEQ ID NO: 5); RRMKEFVSTVMEQLKKSKTLF (SEQ ID NO: 6); SLMQYSEEFRIHFTFKEFQNN (SEQ ID NO: 7); PNPRSLVKPITQLLGRTHTATGIRK (SEQ ID NO: 8); RKVVRELFNITNGARKNAFK (SEQ ID NO: 9); FKILVVITDGEKFGDPLGYEDVIPEADR (SEQ ID NO: 10); REGVIRYVIGVGDAFRSEKSR (SEQ ID NO: 11); QELNTIASKPPRDHVFQVNNFE (SEQ ID NO: 12); ALKTIQNQLREKIFAIEGT (SEQ ID NO: 13); QTGSSSSFEHEMSQE (SEQ ID NO: 14); FRSEKSRQELNTIASKPPRDHV (SEQ ID NO: 16); KEFQNNPNPRSL (SEQ ID NO: 18); GTQTGSSSSFEHEMSQEG (SEQ ID NO: 19); SNLRQQPQKFPEALRGCPQEDSD (SEQ ID NO: 20); RQNTGMWESNANVKGT (SEQ ID NO: 21); TSGSGISPSHSQRIA (SEQ ID NO: 22); NQRGSLYQCDYSTGSCEPIR (SEQ ID NO: 23); PRGRARWQC (SEQ ID NO: 24); KLSPRLQYFGQSLSGGQDLT (SEQ ID NO: 25); QKSTRDRLREGQ (SEQ ID NO: 26); SGRPHSRAVFNETKNSTRRQTQ (SEQ ID NO: 27); CETLKLQLPNCIEDPV (SEQ ID NO: 28); FEKNCGNDNICQDDL (SEQ ID NO: 29); VRNDGEDSYRTQ (SEQ ID NO: 30); SYRKVSTLQNQRSQRS (SEQ ID NO: 31).

Preferably, the peptide includes one or more metal binding domains of CD11b. More preferably, the metal binding domains encompass amino acids 358–412, 426–483, 487–553, and 554–614 of CD11b. Most preferably, the peptide includes one of the following sequences: DVDSNGSTD (SEQ ID NO: 46); DVNGDKLTD (SEQ ID NO: 47); DLTMDGLVD (SEQ ID NO: 48); DSDMNDAYL (SEQ ID NO: 49).

In a preferred embodiment, the peptides are soluble under physiological conditions.

In a related aspect, the invention features a heterodimer which includes a first peptide and a second peptide; the first peptide includes at least one extracellular region of a CD11 subunit and lacks the transmembrane and cytoplasmic portions of the CD11 subunit; the second peptide comprising at least one extracellular region of a CD18 subunit and lacks the transmembrane and cytoplasmic portions of the CD18 subunit; the first and second peptides are associated to form the heterodimer; and the heterodimer is capable of inhibiting a CD11/CD18 mediated immune response. In preferred embodiments, the CD11 subunit is: CD11a; CD11b; CD11c. In a more preferred embodiment, the heterodimer is $CD11b^{1089}/CD18^{699}$.

In another aspect, the invention features a method of controlling phagocyte-mediated tissue damage to a human patient. The method includes administering a therapeutic composition to a patient; the therapeutic composition includes a physiologically acceptable carrier and a peptide or a heterodimer of the invention. More preferably, the method is used to control phagocyte-mediated tissue damage due to ischemia-reperfussion. Most preferably, the method is used to control phagocyte-mediated tissue damage to the heart muscle associated with reduced perfusion of heart tissue during acute cardiac insufficiency.

In another aspect, the invention features a method of producing a recombinant β2 integrin heterodimer. The method includes the steps of: (a) providing a recombinant cell encoding a CD11 peptide lacking both the transmembrane domain and the cytoplasmic domain and a CD18 peptide lacking both the transmembrane domain and the cytoplasmic domain; (b) culturing the recombinant cell; and (c) isolating the heterodimer from the culture supernatant. More preferably, the method is used to produce a soluble recombinant β2 integrin heterodimer. In preferred embodiments, the CD11 peptide of the heterodimer is a CD11a peptide; is a CD11b peptide; is a CD11c peptide.

In another aspect, the invention features a monoclonal antibody which is raised to a peptide or a heterodimer of the invention and which is capable of inhibiting a CD11/CD18 mediated immune response.

In another aspect, the features a human CD11b recombinant peptide.

"β2 integrins" include all leukocyte adhesion molecules which include a CD18 subunit. By the "A domain of CD11b" is meant the amino acid sequence corresponding to the sequence of CD11b from $Cys^{128}$ to $Gly^{321}$ or an amino acid sequence produced by introducing one or more conservative amino acid substitutions in an amino acid sequence corresponding to the sequence of CD11b from $Cys^{128}$ to $Gly^{321}$ "CD11/CD18-mediated immune response" includes those CD11/CD18-related functions mentioned above: chemotaxis, immune adherence (homotypic cell adhesion or aggregation), adhesion to endothelium, phagocytosis, antibody-dependent or -independent cellular cytotoxicity, and superoxide and lysosomal enzyme release. Inhibition of these immune functions can be determined by one or more of the following inhibition assays as described in greater detail below: iC3b binding, cell—cell aggregation, phagocytosis, adhesion to endothelium, and chemotaxis. As used herein, a human CD11b recombinant peptide is a chain of amino acids derived from recombinant CD11b-encoding cDNA, or the corresponding synthetic DNA. "$CD11^{1089}/CD18^{699}$" is a heterodimer which comprises amino acids 1–1089 of human CD11 and amino acids 1–699 of CD18.

Other features and advantages of the invention will be apparent from the following description of the preferred embodiments thereof, and from the claims.

DESCRIPTION OF THE PREFERRED EMBODIMENTS

The drawings will first briefly be described.
Drawings

FIG. 1 is the CDNA sequence and deduced amino acid sequence of the open reading frame of human CD11b from Arnaout et al., *J. Cell. Biol.* 106:2153 (1988) (SEQ ID NO: 40; SEQ ID NO: 43).

Figure 6:
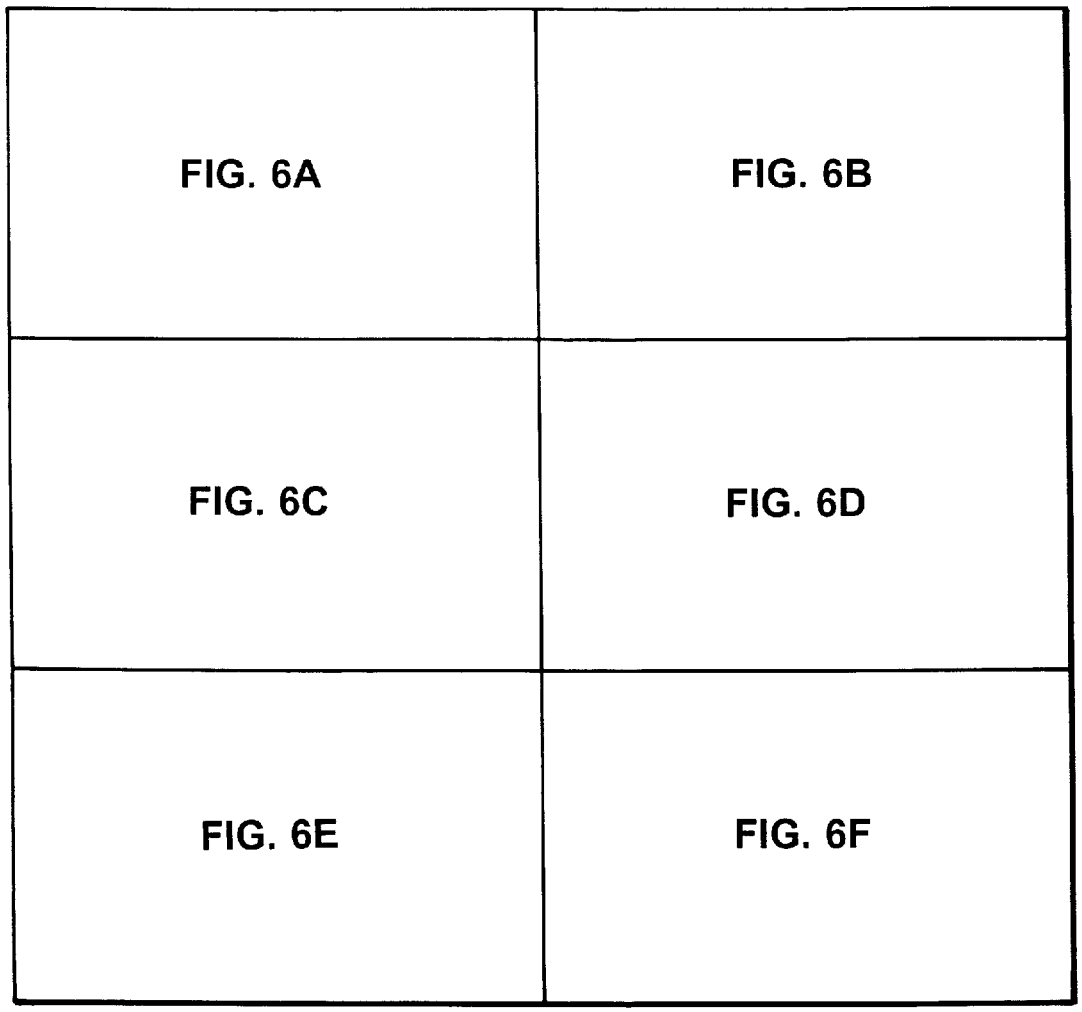

FIG. 6 is the cDNA sequence and deduced amino acid sequence of human CD11a from Larson et al., *J. Cell. Biol.* 108:703 (1989) SEQ ID NO: 39; SEQ ID NO: 42.

Figures 7, 7A:
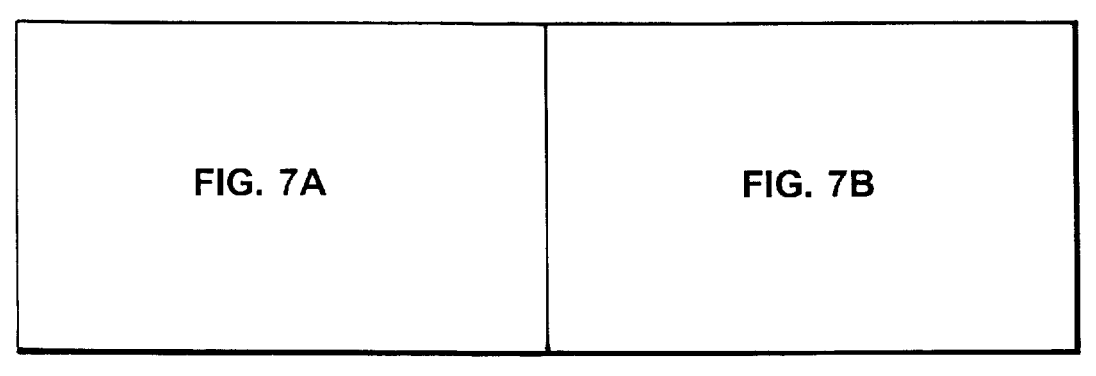

FIG. 7 is the cDNA sequence and deduced amino acid sequence of human CD11c from Corbi et al., *EMBO J.* 6:4023 (1987) SEQ ID NO: 44.

FIG. 8 is the cDNA sequence of human CD18 from Law et al., *EMBO J.* 6:915 (1987) SEQ ID NO: 41.

PEPTIDES

As described in greater detail elsewhere, each member of the β2 integrin family is a heterodimer consisting of two subunits: a CD11 subunit (with at least three variants designated CD11a, CD11b, and CD11c) and a CD18 subunit. Each subunit includes a transmembrane anchor which connects a cytoplasmic segment to an extracellular segment. The two subunits interact to form a functional heterodimer. As described in greater detail below, the extracellular segments of the β2 integrin subunits contain various functional domains which are the focus of the invention.

Without wishing to bind myself to a particular theory, it appears that the peptides of the invention antagonize CD11/CD18-mediated immune responses by competitively inhibiting binding of leukocytes bearing a member of the β$_2$ integrin family to the respective binding partners of that family. Specifically, the peptides of the invention include an immune-response inhibiting extracellular segment of any one of the β2 integrin subunits—CD11a, CD11b, CD11c, CD18—or a heterodimer composed of a portion of an α (CD11a, CD11b, or CD11c) subunit together with a portion of a β subunit (CD18). Candidate β2 integrin subunits can be evaluated for their ability to antagonize CD11/CD18-mediated immune responses by any of several techniques. For example, subunits may be tested for their ability to interfere with neutrophil adhesion to endothelial cells using an assay described in detail below. Specific regions of the β2 integrin subunits can be evaluated in a similar manner. Any extracellular region of a β2 integrin subunit may be screened for its ability to interfere with CD11/CD18 mediated immune response. Regions of CD11 whose sequences are conserved between two or more subunits are preferred candidates for antagonizing CD11/CD18—mediated immune response. For example, the A domain (corresponding to Cys$^{128}$ to Gly$^{321}$ of CD11b) is conserved between CD11a, CD11b, and CD11c. The A domain is 64% identical in CD11b and CD11c and 36% homologous between these two subunits and CD11a. This domain is also homologous to a conserved domain in other proteins involved in adhesive interactions including von Willebrand's factor, cartilage matrix protein, VLA2, and the complement C3b/C4b—binding proteins C2 and factor B. The extracellular portions of CD11a, CD11b and CD11c include seven homologous tandem repeats of approximately 60 amino acids. These repeats are also conserved in the α subunits of other integrin subfamilies (e.g., fibronectin receptor). Arnaout et al., *Blood* 75:1037 (1990).

Regions of CD18 which are conserved among β intergrin subunits (i.e., the β subunits of β1, β2 and β3 integrins) are also good candidates for regions capable of interfering with CD11/CD18—mediated immune response. For example, CD18 has four tandem repeats of an eight-cysteine motif. This cysteine-rich region is conserved among β subunits. Just amino terminal to this cysteine rich region is another conserved region, 247 amino acids long, which is conserved in several integrin β subunits.

Described in detail below are techniques for generating CD11b peptides and heterodimers. The same techniques may be used to generate CD11a, CD11c, and CD18 peptides as well as CD11a/CD18 and CD11c/CD18 heterodimers. FIG. 6 depicts the cDNA sequence of human CD11a (SEQ ID NO: 39); FIG. 7 depicts the cDNA sequence of human CD11c (SEQ ID NO: ); FIG. 8 depicts the cDNA sequence of CD18 (SEQ ID NO: 41).

DNA molecules encoding all or part of CD11a, CD11b, CD11c or CD18 can be obtained by means of polymerase chain reaction amplification. In this technique two short DNA primers are used to generate multiple copies of a DNA fragment of interest from cells known to harbor the mRNA of produced by the gene of interest. This technique is described in detail by Frohman et al., *Proc. Nat'l Acad Sci. USA* 85:8998 (1988). Polymerase chain reaction methods are generally described by Mullis et al. (U.S. Pat. Nos. 4,683,195 and 4,683,202).

For example, to clone a portion of CD11a, the known sequence of CD11a is used to design two DNA primers which will hybridize to opposite strands outside (or just within) the region of interest. The primers must be oriented so that when they are extended by DNA polymerase, extension proceeds into the region of interest. To generate the CD11a DNA, polyA RNA is isolated from cells expressing CD11a. A first primer and reverse transcriptase are used to generate a cDNA form the mRNA. A second primer is added; and Taq DNA polymerase is used to amplify the cDNA generated in the previous step. Alternatively, the known sequences of CD11a, CD11b, CD11c and CD18 can be used to design highly specific probes for identifying cDNA clones harboring the DNA of interest. A CDNA library suitable for isolation of CD11a, CD11b, and CD11c DNA can be generated using phorbol ester-induced HL-60 cells (ATCC Accession No. CCL 240) as described by Corbi et al. (*EMBO J.* 6:4023, 1987) and Arnaout et al., *Proc. Nat'l Acad Sci. USA* 85:2776, 1988); CD18 DNA can be isolated from a library generated using U937 cells (ATCC Accession No. CRL 1593) as described by Law et al. (*EMBO J.* 6:915, 1987). These cell lines are also suitable for generating cDNA by polymerase chain reaction amplification of mRNA as described above.

Heterodimers comprised of part of CD11c and CD18 can be produced as described below for CD11b/CD18 by changing a codon amino terminal to the transmembrane region (e.g. Pro$^{1086}$) to a stop codon. Heterodimers comprised of part of CD11a can be produced by changing a codon amino terminal to the transmembrane region (e.g., Lys$^{1087}$) to a stop codon. DNA encoding the truncated CD11 subunit is then introduced into cells along with DNA encoding a similarly truncated CD18 molecule (described below). These cells are then used as a source of heterodimer.

Isolation of a Human CD11b cDNA Clone.

A 378 base pair (bp) cDNA clone encoding guinea pig CD11b was used as a probe to isolate three additional cDNA clones from a human monocyte/lymphocyte cDNA library as described in Arnaout et al., *Proc. Nat'l. Acad. Sci. USA* 85:2776 (1988); together these three clones contain the 3,048 nucleotide sequence encoding the CD11b gene shown in FIG. 1 (SEQ ID NO: 40). Arnaout et al., *J. Cell. Biol.* 106:2153 (1988).

In order to express CD11b, a mammalian expression vector was constructed by assembling the above-described three cDNA clones. Appropriate restriction enzyme sites within the CD11b gene can be chosen to assemble the cDNA inserts so that they are in the same translation reading frame. Arnaout et al., *J. Clin. Invest.* 85:977 (1990). A suitable basic expression vector can be used as a vehicle for the 3,048 bp complete cDNA fragment encoding the human CD11b peptide; the recombinant cDNA can be expressed by transfection into, e.g., COS-1 cells, according to conventional techniques, e.g., the techniques generally described by Aruffo et al., *Proc. Nat'l. Acad. Sci. USA* 84:8573 (1987) or expressed in *E. coli* using standard techniques. Smith et al., *Gene* 67:31 (1988).

Isolation of CD11b Peptide from Mammalian Cells

The CD11b protein can be purified from the lysate of transfected COS-1 cells, using affinity chromatography and lentil-lectin Sepharose and available anti-CD11b monoclonal antibody as described by Pierce et al. (1986) supra and Arnaout et al., *Meth. Enzymol.* 150:602 (1987).

If the desired CD11b peptide is shorter than the entire protein, DNA encoding the desired peptide can be expressed in the same mammalian expression vector described above using the selected DNA fragment and the appropriate restriction enzyme site, as outlined above. The selected DNA fragment may be isolated according to conventional techniques from one of the CD11b cDNA clones or may be synthesized by standard polymerase chain reaction amplification, as described above. See also Saiki et al., (*Science* 239:487, 1988).

Characterization of the CD11b Polypeptide

The coding sequence of the complete CD11b protein is preceded by a single translation initiation methionine. The translation product of the single open reading frame begins with a 16-amino acid hydrophobic peptide representing a leader sequence, followed by the $NH_2$-terminal phenylalanine residue. The translation product also contained all eight tryptic peptides isolated from the purified antigen, the amino-terminal peptide, and an amino acid hydrophobic domain representing a potential transmembrane region, and a short 19-amino acid carboxy-terminal cytoplasmic domain (FIG. 1 illustrates the amino acid sequence of CD11b; SEQ ID NO: 43). The coding region of the 155–165 kD CD11b (1,136 amino acids) is eight amino acids shorter than the 130–150 kD alpha subunit of CD11c/CD18 (1,144 amino acids). The cytoplasmic region of CD11b contains one serine residue that could serve as a potential phosphorylation site. The cytoplasmic region is also relatively rich in acidic residues and in proline (FIG. 1). Since CD11b/CD18 is involved in the process of phagocytosis and is also targeted to intracellular storage pools, these residues are candidates for mediating these functions. The long extracytoplasmic amino-terminal region contains three or four metal-binding domains (outlined by broken lines in FIG. 1) that are similar to $Ca^{2+}$-binding sites found in other integrins. Each metal binding site may be composed of two noncontiguous peptide segments and may be found in the four internal tandem repeats formed by amino acid residues 358–412, 426–483, 487–553, and 554–614. The portion of the extracytoplasmic domain between $Tyr^{465}$ and $Val^{492}$ is homologous to the fibronectin-like collagen binding domain and IL-2-receptor. The extracytoplasmic region also contains an additional unique 187–200 amino acid domain, the A domain, between $Cys^{128}$ to $Glu^{321}$, which is not present in the homologous (α) subunits of fibronectin, vitronectin, or platelet IIb/IIIa receptors. This sequence is present in the highly homologous CD11c protein (α of p150,95) with 64% of the amino acids identical and 34% representing conserved substitutions. Arnaout et al., *J. Cell Biol.* 106:2153, 1988; Arnaout et al. *Blood* 75:1037 (1990). It is known that both CD11b/CD18 and CD11c/CD18 have a binding site for complement fragment C3 and this unique region may be involved in C3 binding. This region of CD11b also has significant homology (17.1% identity and 52.9% conserved substitutions) to the collagen/heparin/platelet GpI binding regions of the mature von Willebrand factor (domains A1–A3). The A domain is also homologous to a region in CD11a. Larson et al., *J. Cell Biol.* 108:703 (1989). The A domain is also referred to as the L domain or the I domain. Larson et al., supra (1988); Corbi et al., *J. Biol. Chem.* 263:12,403 (1988).

CD11b Petides

The following peptides can be used to inhibit CD11b/CD18 activity: a) peptides identical to the above-described A domain of CD11b, or a portion thereof, e.g., DIAFLIDGS (SEQ ID NO:32), FRRMKEFVS (SEQ ID NO:33), FKILWITDGE (SEQ ID NO:34), DGEKFGDPLGYEDVIPEADR (SEQ ID NO:17), or VIRYVIGVGDA SEQ ID NO:35); b) peptides identical to the above-described fibronectin-like collagen binding domain, or a portion thereof, e.g., YYEQTRGGQVSVCPLPRGRARWQCDAV (SEQ ID NO:38); c) peptides identical to one or more of the four metal binding regions of CD11b, or a portion thereof, e.g., DVDSNGSTD (SEQ ID NO:46), DVNGDKLTD (SEQ ID NO:47), DLTMDGLVD (SEQ ID NO:48), DSDMNDAYL (SEQ ID NO:49); d) peptides substantially identical to the complete CD11b; or e) other CD11b domains, e.g. KSTRDRLR (SEQ ID NO:15).

Also of interest is a recombinant peptide which includes part of the A domain, e.g, Asn Ala Phe Lys Ile Leu Val Val Ile Thr Asp Gly Clu Lys Phe Gly Asp Pro Leu Gly Tyr Glue Asp Val Ile Pro Glu Ala Asp Arg Glu Gly Val (SEQ ID NO: 50). The A domain binds iC3b, gelatin, and fibrinogen and binding is disrupted by EDTA. The A domain also binds both $Ca^{2+}$ and $Mg^{2+}$. This result unexpected since the A domain lies outside of the region of CD11b previously predicted (Arnaout et al., *J. Cell Biol.* 106:2153, 1988; Corbi et al., *J. Biol. Chem.* 25:12403, 1988) to contain metal binding sites.

Heterodimers

It is advantageous to administer the heterodimer formed by the CD11b and CD18 proteins. Expression of CD11b is described elsewhere in this application. Expression of CD18 has been reported by others. Law et al. *Embo, J.* 6:915 (1987); Kishimoto et al. *Cell* 48:681 (1987). The strategies described above or in those reports can be used to obtain CD18 to make such a heterodimer. Preferred heterodimers are soluble under physiological conditions. The heterodimer described below is generated by changing the codon for $Leu^{1090}$ in CD11b (SEQ ID NO: 40) to a stop codon and the codon for $Asn^{700}$ of CD18 (SEQ ID NO: 41) to a stop codon. Other potentially soluble heterodimers can be generated by introducing a stop codon at positions amino terminal to those described below.

Generation of Soluble Heterodimers

A soluble form of a CD11b/CD18 heterodimer was produced in COS cells. To produce this molecule the codons for $Leu^{1090}$ and $Asn^{700}$ located at the predicted extracellular boundaries of CD11b and CD18 respectively, were replaced with in-frame translational stop codons using oligonucleotide-directed gapped-duplex mutagenesis of the wild-type cDNAs (described below).

To determine if COS cells can express a soluble form of CD11b/CD18, COS cells were co-transfected with cDNA encoding the truncated forms of CD11b ($CD11b^{1089}$) and CD18 ($CD11^{699}$). Secreted proteins were analyzed by immunoprecipitation and SDS-PAGE. The results of this analysis are presented in FIG. 2.

Briefly, COS cells were transfected as previously described (Arnaout et al., *J. Clin. Invest.* 85:977, 1990).

$7 \times 10^6$ transfected cells were labeled overnight with 0.1 mCi of $^{35}$S methionine, and the harvested supernatants were used for immunoprecipitation with NS1, a non-reactive monoclonal antibody (mAb) (lane 1); 44a, an anti-CD11b mAb (lane 2); or TS18, an anti-CD18 mAb (lane 3). Immunoprecipitation and antibodies as described by Arnaout et al., *J. Cell. Physiol.* 137:305 (1988); Trowbridge et al., *J. Exp. Med.* 154:1517 (1981); and Sanchez-Madrid et al., *J. Exp. Med.* 158:1785 (1983).

Figure 2:
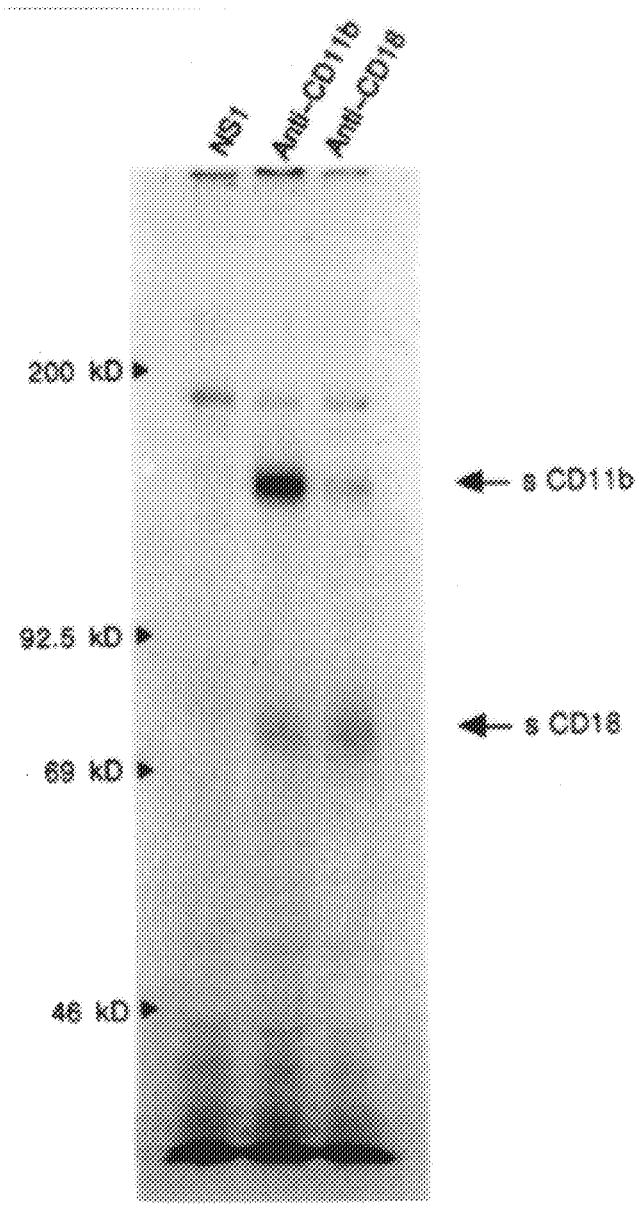
FIG. 2 is a representation of the results of an immunoprecipitation assay.

As shown in FIG. 2, both $CD11b^{1089}$ and $CD18^{699}$ were immunoprecipitated from supernatants of cells transfected with DNA encoding the truncated subunits. The secreted $CD11b^{1089}$ had an apparent molecular weight of 149 kD; the secreted $CD18^{699}$ had an apparent molecular weight of 84 kD (compared to 155 kD and 94 kD respectively for the wild-type subunits). Arnaout et al., *New Engl. J. Med.* 312:457 (1985); Dierner et al., *J. Immunol.* 135:537 (1985); Arnaout et al., *J. Clin. Invest.* 72:171 (1983); Klebanoff et al., *J. Immunol.* 134:1153 (1985). That mAbs directed against either the CD11b or CD18 immunoprecipitated both truncated forms, indicates that the secreted subunits are expressed as an $CD11b^{1089}/CD18^{699}$ complex and that neither the cytoplasmic nor the transmembrane region of the subunits are necessary for heterodimer formation. These mAbs did not precipitate receptor subunits from the supernatants of mock-transfected cells. Arrowheads at left indicate the positions of molecular weight size markers: myosin (200 kD), phosphorylase b (92.5 kD), bovine serum albumin (69 kD), and ovalbumin (46 kD). Arrows at right indicate the expected positions of $CD11b^{1089}$ and $CD18^{699}$.

$CD11b^{1089}/CD18^{699}$ was next tested for its ability to bind iC3b (the receptor bound by wild-type CD11b/CD18). Briefly, COS cells were transfected $CD11b^{1089}$ and $CD18^{699}$ cDNA as described above. Cells were labeled with $^{35}$S-methionine as described by Dana et al., *J. Clin. Invest.* 79:1010 (1987). Supernatants from both co-transfected COS cells ($7 \times 10^6$ cells) and mock-transfected COS cells ($7 \times 10^6$ cells) were concentrated to one ml using collodion bags (10,000 MW cut off). 100 μl of the concentrated supernatant were used for immunoprecipitation, and the rest of the supernatant was incubated with C3b-sepharose or iC3b-sepharose. C3b-sepharose and iC3b-sepharose was washed, eluted with 0.4 M NaCl and the eluted proteins were analyzed by SDS-PAGE and autoradiography. Binding of wild-type, membrane-bound CD11b/CD18 to iC3b-sepharose or C3b-sepharose was performed as described by Arnaout et al., (*In Methods in Enzymology*, DiSabato, Ed., Acad. Press Inc., Fla., 1987) using the detergent soluble fraction from $1 \times 10^8$ $^{125}$I-surface-labelled neutrophils.

Figure 3:
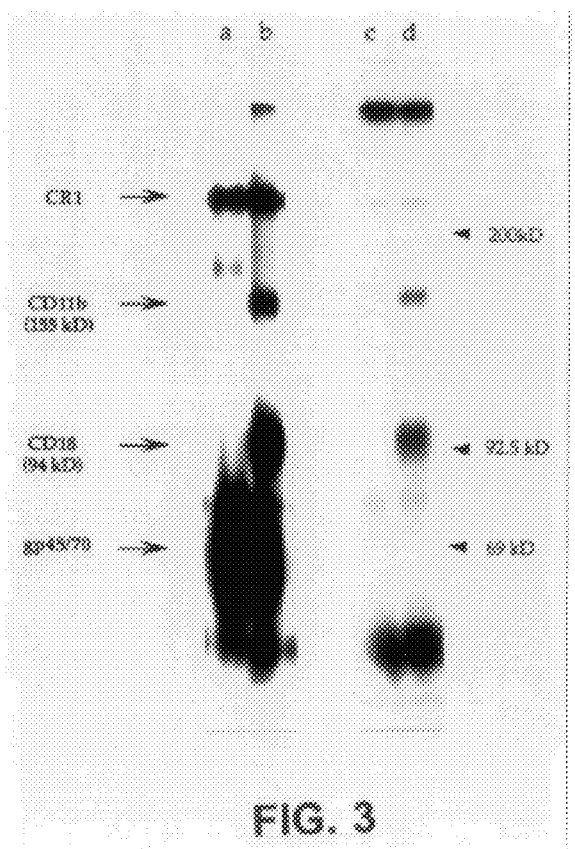
FIG. 3 is a representation of the results of an immunoprecipitation assay.

FIG. 3 illustrates the results of SDS-PAGE analysis of neutrophil-derived $^{125}$I-surface-labeled glycoproteins eluted from C3b-sepharose and iC3b-sepharose. Eluants from C3b-sepharose (lane a) contained complement receptor type 1 (250kD) and the C3-binding regulatory protein gp45/70 (45–70 kD). Eluants from iC3b-sepharose (lane b) contained two additional proteins at 155 kD, 94 kD, representing wild-type CD11b and CD18. CD11b/CD18 was immunoprecipitated with 44a mAb (an anti-CD11b mAb) from material eluted from iC3b-sepharose (lane d), but not from material eluted from C3b-sepharose (lane c), confirming previous results. Malhorta et al., *Eur. J. Immunol.* 16:177, (1986). The arrowheads at right indicate the positions of molecular weight standards: myosin (200 kD), phosphorylase b (92.5 kD), and bovine serum albumin (69 kD). The arrows at left indicate the expected position of CR1, CD11b, CD18 and gp45/70.

Figure 4:
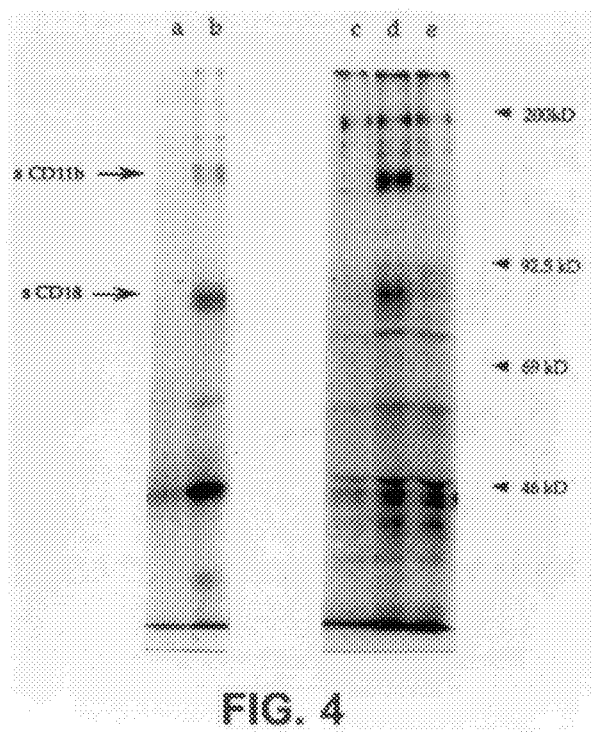
FIG. 4 is a representation of the results of an immunoprecipitation assay.

FIG. 4 shows the results of SDS-PAGE analysis of $CD11b^{1089}/CD18^{699}$ heterodimer binding to iC3b. An anti-CD11b mAb (44a) was used to immunoprecipitate proteins from culture supernatants of mock-transfected COS cells (lane a), and from COS cells co-transfected with $CD11b^{1089}$ and $CD18^{699}$ cDNAs (lane b). No specific radiolabeled material was present in eluant of iC3b-sepharose exposed to culture supernatant of mock-transfected COS cells (lane c). $CD11b^{1089}/CD18^{699}$ was eluted from iC3b-sepharose (lane d), but not from C3b-sepharose (lane e) exposed to culture supernatant of co-transfected cells. Arrowheads at right indicate the positions of molecular weight standard standards (as in FIG. 2). Arrows at left indicate the expected positions of $CD11b^{1089}$ and $CD18^{699}$. Similar results were seen with supernatants from two other transfections.

The ability of $CD11b^{1089}/CD18^{699}$ to inhibit binding of human neutrophils to inflamed endothelium was examined and compared to the inhibition induced by anti-CD11b mAb and anti-CD18 mAb. Adherence of purified human neutrophils to confluent monolayers of human umbilical vein endothelial cells (HUVE) pre-treated with recombinant IL-1 (10 units/ml for 4 hours at 37° C.) was measured as described by Arnaout et al., (*J. Cell. Physiol.* 137:305, 1988) with the following modifications. Neutrophils were labeled with carboxyfluorescein (CF, Molecular Probes, Eugene, Oreg.) by incubating $4 \times 10^6$ cells with 30 μg of CF in one ml of Tris-buffered saline for 10 minutes on ice, followed by three washes. HUVE were pre-incubated for 10 minutes at 37° C. with supernatants of COS cells co-transfected with $CD11b^{1089}$ and $CD18^{699}$ CDNA supernatants, or for 5 minutes at room temperature with the non-reactive monoclonal antibody NS1, 44a (anti-CD11b) or TS18 (anti-CD18) ascites (1:100 dilution). Labeled neutrophils were then added and incubation was continued for an additional 10 minutes. The plates HUVE were washed twice, and adherent neutrophils were harvested by washing with 0.1% SDS and 0.1N NaOH. Relative numbers of neutrophils were measured (at Exc., 490 nm; Em, 300 nm) using a Fluorometer (SLM 8000, SLM Aminco, Urbana, Ill.). All assays were done in triplicate. Labels along the horizontal axis indicate the molecule added to HUVE. 'Buffer' indicates that no antibodies were added. 'Sham' indicates that supernatant from mock transfected cells was added.

Figure 5A:
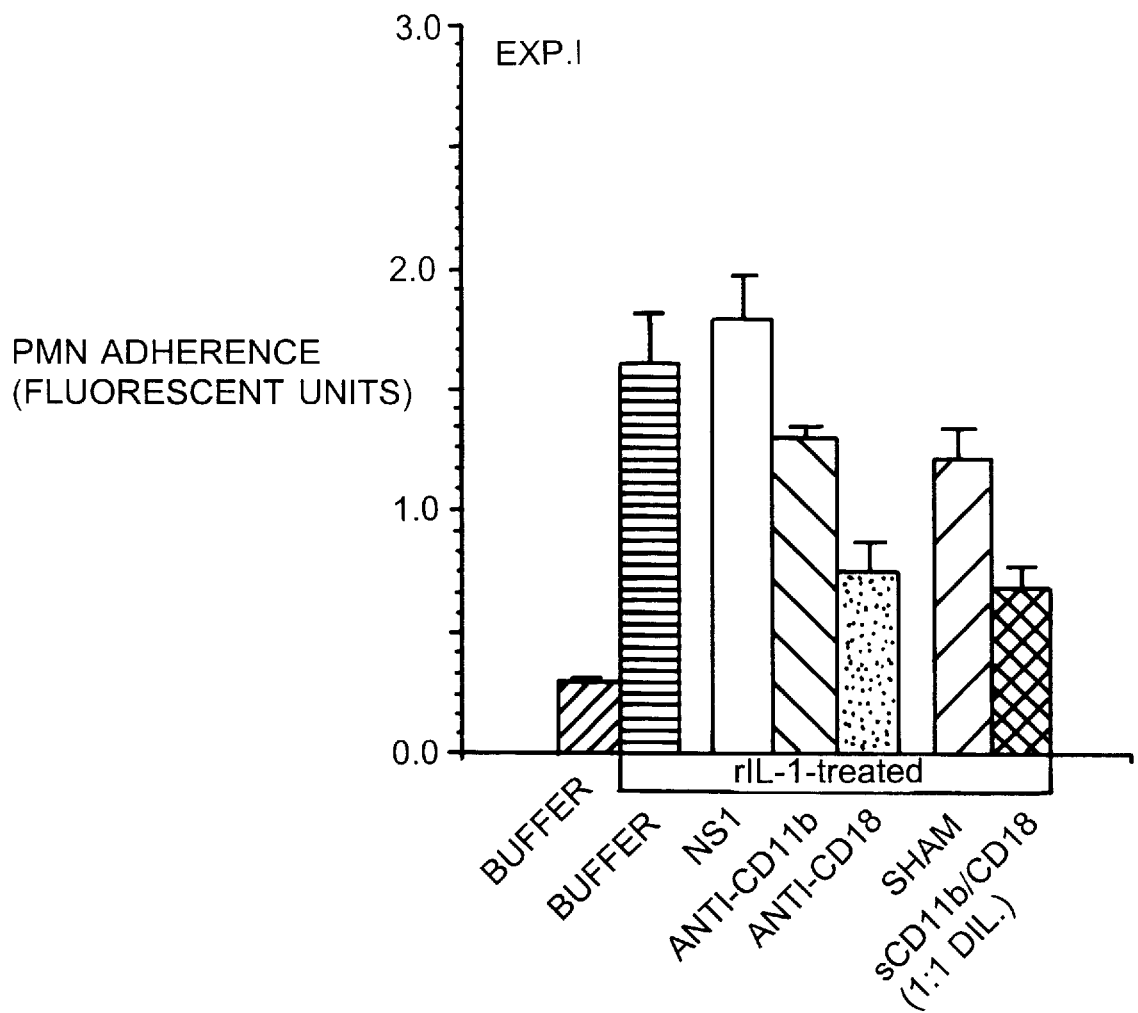
FIG. 5 is a graph of the effect of various proteins and antibodies on neutrophil adhesion to endothelium.
Figure 5B:
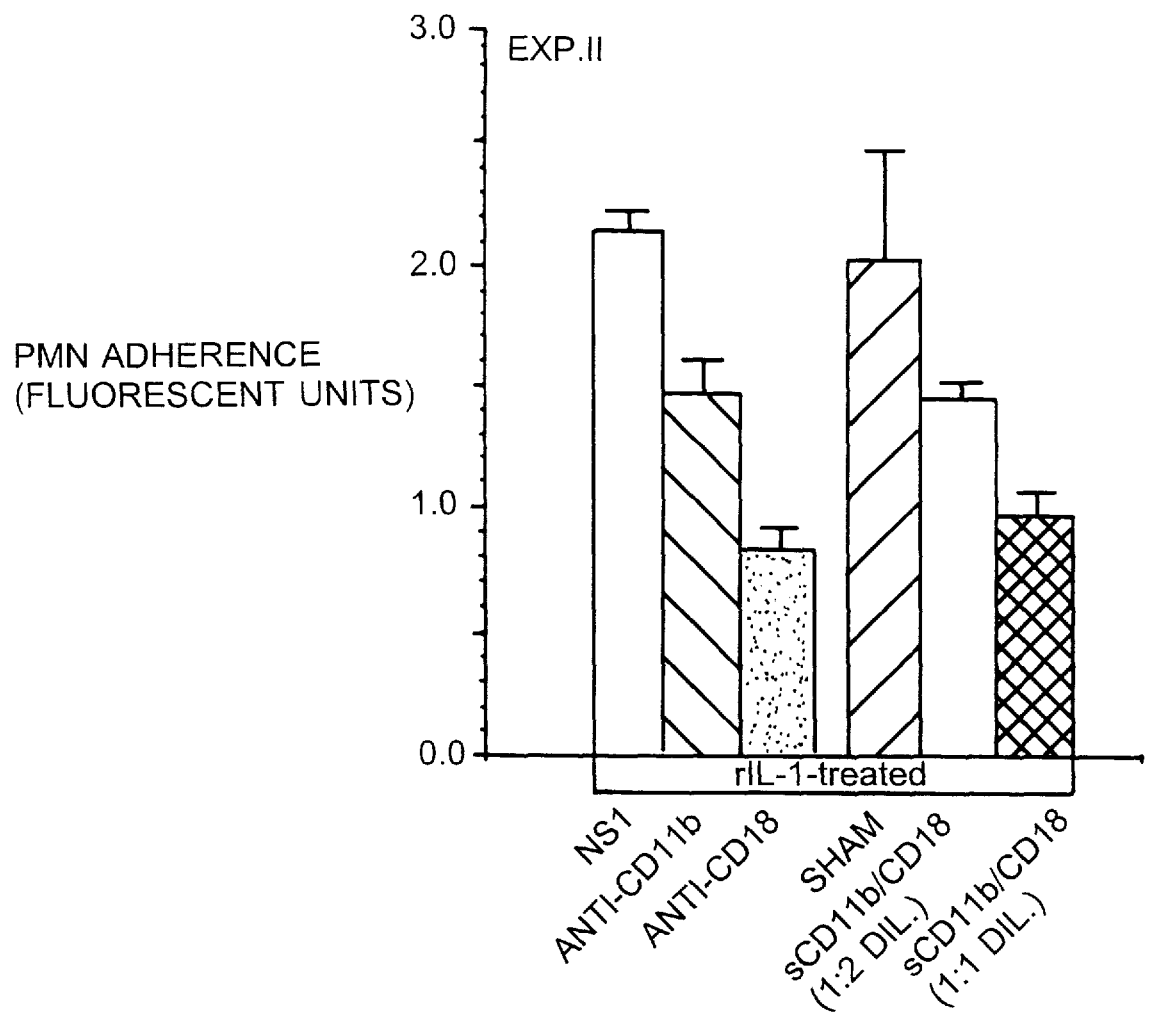

As shown in FIG. 5, culture supernatants containing $CD11b^{1089}/CD18^{699}$ (approximately 10–50 ng/ml) were found to be at least as effective in blocking neutrophil adhesion to rIL-1-induced endothelium as monoclonal antibodies directed against CD11b or CD18. $CD11b^{1089}/CD18^{699}$ was more effective than 44a mAb (an anti-CD11b mAb) in inhibiting adhesion to rIL-1-activated endothelium and comparable to inhibition seen using TS18 mAb (an anti-CD18 mAb), suggesting the presence of multiple functional sites on $CD11b^{1089}$ and/or the possibility that CD18 (like other β integrins) contains a recognition site(s) for interacting with ligand(s) expressed on endothelium.

Generation of Truncated CD11b and CD18

PAT-X plasmid containing the partial CD18 CDNA clone J19 (Law et al. supra, 1987) was linearized with HindIII or digested with NcoI (to generate a 1331 bp gap). These two plasmids were mixed with an excess of the synthetic and 5'-end phosphorylated 18-mer (5'-aggccccTaGatcgccgc) containing desired nucleotide mutations (caps). The mixture was denatured by boiling and renatured by stepwise cooling. Reannealed DNA (containing single-stranded region to which the mutant 18-mer is hybridized) was primer extended to fill the gap, and used to transform *E. coli* strain BMH 71-18 mutL. Arnaout et al., *J. Clin. Invest.* 85:977 (1990). Plasmids containing the mutation were identified by differential hybridization with $^{32}$P-labeled wild-type- or mutant 18-mers and DNA used to transform E. coli JM109. Positive colonies were identified following rehybridization, sequenced to verify the mutation, then used to replace the corresponding fragment in wild-type full length CD18 cDNA cloned in πH3M expression vector. Arnaout et al., *J. Clin. Invest.* 85:977 (1990). A stop codon was similarly introduced in CD11b. Blue Script®, a betagalactosidase complementation vector (stratagene, La Jolla, Calif.) containing the full coding region of membrane-bound CD11b was used. A mixture of KpnI-linearized and gapped (by removing a SmaI fragment, 1048 bp long) CD11b cDNAs were mixed with an excess of the synthetic mutant 18-mer (5'-caaccccTAgccgctcat). Mutant plasmid was produced and isolated as detailed above.

Monoclonal Antibodies

Monoclonal antibodies directed against CD11 or CD18 can be used to antagonize CD11/CD18-mediated immune response. Useful monoclonal antibodies can be generated by using a peptide of the invention as an immunogen. For example, monoclonal antibodies can be raised against the A domain of CD11b, CD11a or CD11c.

Anti-CD11b monoclonal antibodies which inhibit iC3b binding (mAb 903), neutrophil adhesive interactions, e.g., aggregation and chemotaxis, (mAb 904), or both activities (mAb44a) have been identified. Other monoclonal antibodies (OKM-1, which inhibits fibrinogen binding, and OKM9) have also been mapped to this region. Dana et al., *J. Immunol.* 137:3259 (1986). These monoclonal antibodies recognize epitopes in the A domain of CD11b. Dana et al., *JASON* 1:549 (1990).

Additional useful monoclonal antibodies can be generated by standard techniques. Preferably, human monoclonal antibodies can be produced. Human monoclonal antibodies can be isolated from a combinatorial library produced by the method of Huse et al. (*Science,* 246:1275, 1988). The library can be generated in vivo by immunizing nude or SCID mice whose immune system has been reconstituted with human peripheral blood lymphocytes or spleen cells or in vitro by immunizing human peripheral blood lymphocytes or spleen cells. The immunogen can be any CD11b or CD18 peptide. Similar techniques are described by Duchosal et al., J. Exp. Med. 92:985 (1990) and Mullinax et al., Proc. Nat'l. Acad. USA 87:8095 (1990).

Peptides derived from the A domain of CD11a, CD11b, or CD11c are preferred immunogens. These peptides can be produced in *E. coli* transformed by a plasmid encoding all or part of the A domain.

A CD18 peptide can also be used as an immunogen. Three anti-CD18 mAbs with anti-inflammatory properties (TS18, 10F12, 60.3) have been identified. Binding each of these antibodies to CD18 can be abrogated by a specific point mutation within a particular region of CD18 (Asp$^{128}$ to Asn$^{361}$ of FIG. 8) (SEQ ID No.: 45). Peptide corresponding to this region can be produced in *E. coli* using a plasmid encoding the A domain.

Assays for CD11b (or CD11c) Peptides, Heterodimers and Monoclonal Antibodies

CD11b (or CD11c) peptides, heterodimers, and monoclonal antibodies such as those described above, can be tested in vitro for inhibition in one of the following five assays: iC3b binding, inhibition of phagocytosis, inhibition of monocyte/granulocyte adhesion to enclothelium, inhibition of chemotaxis, or inhibition of cell—cell aggregation. Alternatively, they may be tested in vivo for controlling damage associated with reduced perfusion or immune injury of tissues, as a result of myocardial infarction, burns, frost bite, glomerulonephritis, asthma, adult respiratory distress syndrome, transplant rejection, onset of diabetes mellitus, ischemia, colitis, shock liver syndrome, and resuscitation from hemorrhagic shock.

Inhibition of Granulocyte or Phagocyte Adhesion to iC3b-Coated Erythrocytes or Bacteria The antimicrobial activity of the neutrophil depends to a significant degree on the ability of this cell to establish a firm attachment to its target. For this purpose, neutrophils possess a number of specific cell surface receptors that promote this interaction, such as a receptor which binds to complement C3 (iC3b), e.g. the CD11b/CD18 receptor. Human neutrophilic polymorphonuclear granulocytes can be isolated from EDTA-anticoagulated blood on Ficoll-Hypaque gradients. Boyum, *Scand. J. Clin. Invest. (Suppl.)* 21:77 (1968) modified as described by Dana et al., *J. Clin. Invest.* 73:153 (1984). Phagocytes can be prepared by incubating the mononuclear cell fraction (obtained from Ficoll-Hypaque centrifugation) on plastic petri dishes. Todd et al., *J. Immunol.* 126:1435 (1981). Peptides of the invention can be tested for their ability to inhibit iC3b mediated binding of granulocytes to sheep erythrocytes as described in Dana et al. supra, 1984; and Arnaout et al., supra, 1985.

Inhibition of Phagocytosis

Phagocytosis is an important biological function resulting in clearing of damaged tissue from the body, and in elimination of foreign particles (bacteria, fungi). An in vitro test for inhibition of phagocytosis is described in Arnaout et al., *New Eng. J. Med.* 306:693 (1982).

Inhibition Adhesion to Endothelium

Granulocytes/monocytes must cross vascular endothelium during their egress from blood to extravascular tissues. Studies of leukocyte kinetics in animals indicate that acute inflammatory reactions may be marked by a massive increase in transendothelial monocyte/granulocyte traffic. In many chronic inflammatory lesions, perivascular monocytes accumulate in skin windows more slowly than neutrophils, but later become the predominant cell type. In addition, monocytes leaving the circulation can rapidly acquire the morphology of resident tissue macrophages—in some cases within a few hours of their departure from plasma. Thus, vascular endothelium may be considered an important substrate with which monocytes/granulocytes must interact during adherence, diapedesis, and differentiation. An in vitro assay for monocyte/granulocyte interaction with the vessel wall consists of binding radiolabeled or fluorescein monocyte/granulocyte preparations to cultured vascular endothelium, as described in Arnaout et al., *J. Cell Physiol.* 137:305 (1988). Mentzer et al., *J. Cell Physiol.* 125:285 (1986) describes a lymphocyte adhesion assay. These endothelial adhesion assays are appropriate for CD11a, CD11b or CD11c peptides, heterodimers and monoclonal antibodies when the endothelial cells are pre-activated. When the granulocytes/monocytes (or leukocytes) are pre-activated, these assays are suitable for CD11b peptides, heterodimers or monoclonal antibodies.

Inhibition of Chemotaxis.

The ability of cells of the immune system to migrate is essential to the cellular immune response that results in tissue inflammation. Therefore, a peptide of the invention can be tested for its ability to inhibit chemotaxis, as described in Dana et al., (1986), supra.

Cell—Cell Aggregation

A granulocyte aggregation assay can be performed as described by. Arnaout et al., *New Engl. J. Med.* 306:693 (1982). Aggregation can be induced by zymosan-activated autologous serum or with chemotactic peptides, e.g. FMLP. Aggregation can then be recorded as incremental change in light transmission [ΔT] using a platelet aggregometer. The results can be confirmed by phase microscopy.

Assays for CD11a Peptides, Heterodimers and Monoclonal Antibodies

CD11a peptides, heterodimers and monoclonal antibodies can be tested using the inhibition of endothelial adhesion assay (described above) or a lymphocyte proliferation assay. Arnaout et al., *J. Clin. Invest.* 74:1291 (1984) describes an assay for inhibition of antigen/mitogen induced lymphocyte proliferation.

In Vivo Model for Testing Peptide

Damage to tissues injured by ischemia-reperfussion (e.g., heart tissue during myocardial infarction) can be minimized by administering to an animal an inhibitor of CD11/CD18 mediated immune response. A peptide of the invention may be tested for in vivo effectiveness using animals, e.g., dogs, which have been induced to undergo myocardial infarction. See, e.g. Simpson et al. supra.

Use

The peptide or monoclonal antibody can be administered intravenously in saline solution generally on the order of mg quantities per 10 kilograms of body weight. The peptide can be administered in combination with other drugs, for example, in combination with, or within six hours to three days after a clot dissolving agent, e.g., tissue plasminogen activator (TPA), Activase, or Streptokinase.

I claim:

1. An isolated peptide comprising all or a portion of the A domain of CD11b, said peptide comprising the amino acid sequence of SEQ ID NO: 50, said peptide not comprising the entirety of CD11b.

2. The peptide of claim 1, said peptide comprising all of the A domain of CD11b.

3. An isolated peptide having the sequence of the A domain of CD11b, said peptide comprising the amino acid sequence of SEQ ID NO: 50.

4. An isolated peptide having the amino acid sequence of SEQ ID NO: 50.

* * * * *

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Ala  Tyr  Phe  Gly  Ala  Ser  Leu  Cys  Ser  Val  Asp  Val  Asp  Ser  Asn  Gly
 1                    5                         10                        15
Ser  Thr  Asp  Leu  Val  Leu  Ile  Gly  Ala  Pro
                20                        25
```

( 2 ) INFORMATION FOR SEQ ID NO:2:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Gly  Arg  Phe  Gly  Ala  Ala  Leu  Thr  Val  Leu  Gly  Asp  Val  Asn  Gly  Asp
 1                    5                         10                        15
Lys  Leu  Thr  Asp  Val  Ala  Ile  Gly  Ala  Pro
                20                        25
```

( 2 ) INFORMATION FOR SEQ ID NO:3:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Gln  Tyr  Phe  Gly  Gln  Ser  Leu  Ser  Gly  Gly  Gln  Asp  Leu  Thr  Met  Asp
 1                    5                         10                        15
Gly  Leu  Val  Asp  Leu  Thr  Val  Gly  Ala  Gln
                20                        25
```

( 2 ) INFORMATION FOR SEQ ID NO:4:

(i) SEQUENCE CHARACTERISTICS:
  (A) LENGTH: 26 amino acids
  (B) TYPE: amino acid
  (D) TOPOLOGY: linear (ii) MOLECULE TYPE: peptide (xi) SEQUENCE DESCRIPTION: SEQ ID NO:4:

Tyr Glu Gln Thr Arg Gly Gly Gln Val Ser Val Cys Pro Leu Pro Arg
 1               5                  10                  15
Gly Arg Ala Arg Trp Gln Cys Asp Ala Val
             20                  25

(2) INFORMATION FOR SEQ ID NO:5:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (xi) SEQUENCE DESCRIPTION: SEQ ID NO:5:

Asp Ile Ala Phe Leu Ile Asp Gly Ser Gly Ser Ile Ile Pro His Asp
 1               5                  10                  15
Phe Arg Arg Met Lys
             20

(2) INFORMATION FOR SEQ ID NO:6:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (xi) SEQUENCE DESCRIPTION: SEQ ID NO:6:

Arg Arg Met Lys Glu Phe Val Ser Thr Val Met Glu Gln Leu Lys Lys
 1               5                  10                  15
Ser Lys Thr Leu Phe
             20

(2) INFORMATION FOR SEQ ID NO:7:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (xi) SEQUENCE DESCRIPTION: SEQ ID NO:7:

Ser Leu Met Gln Tyr Ser Glu Glu Phe Arg Ile His Phe Thr Phe Lys
 1               5                  10                  15
Glu Phe Gln Asn Asn
             20

(2) INFORMATION FOR SEQ ID NO:8:

(i) SEQUENCE CHARACTERISTICS:
    (A) LENGTH: 25 amino acids
    (B) TYPE: amino acid
    (D) TOPOLOGY: linear (ii) MOLECULE TYPE: peptide ( x i ) SEQUENCE DESCRIPTION: SEQ ID NO:8:

Pro Asn Pro Arg Ser Leu Val Lys Pro Ile Thr Gln Leu Leu Gly Arg
1               5                   10                  15

Thr His Thr Ala Thr Gly Ile Arg Lys
        20                  25

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Arg Lys Val Val Arg Glu Leu Phe Asn Ile Thr Asn Gly Ala Arg Lys
1               5                   10                  15

Asn Ala Phe Lys
        20

( 2 ) INFORMATION FOR SEQ ID NO:10:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Phe Lys Ile Leu Val Val Ile Thr Asp Gly Glu Lys Phe Gly Asp Pro
1               5                   10                  15

Leu Gly Tyr Glu Asp Val Ile Pro Glu Ala Asp Arg
        20                  25

( 2 ) INFORMATION FOR SEQ ID NO:11:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Arg Glu Gly Val Ile Arg Tyr Val Ile Gly Val Gly Asp Ala Phe Arg
1               5                   10                  15

Ser Glu Lys Ser Arg
        20

( 2 ) INFORMATION FOR SEQ ID NO:12:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Gln Glu Leu Asn Thr Ile Ala Ser Lys Pro Pro Arg Asp His Val Phe
1               5                   10                  15

Gln Val Asn Asn Phe Glu
        20

( 2 ) INFORMATION FOR SEQ ID NO:13:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Ala  Leu  Lys  Thr  Ile  Gln  Asn  Gln  Leu  Arg  Glu  Lys  Ile  Phe  Ala  Ile
 1              5                        10                       15
Glu  Gly  Thr
```

( 2 ) INFORMATION FOR SEQ ID NO:14:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Gln  Thr  Gly  Ser  Ser  Ser  Ser  Phe  Glu  His  Glu  Met  Ser  Gln  Glu
 1              5                        10                       15
```

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Lys  Ser  Thr  Arg  Asp  Arg  Leu  Arg
 1              5
```

( 2 ) INFORMATION FOR SEQ ID NO:16:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Phe  Arg  Ser  Glu  Lys  Ser  Arg  Gln  Glu  Leu  Asn  Thr  Ile  Ala  Ser  Lys
 1              5                        10                       15
Pro  Pro  Arg  Asp  His  Val
                20
```

( 2 ) INFORMATION FOR SEQ ID NO:17:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Asp  Gly  Glu  Lys  Phe  Gly  Asp  Pro  Leu  Gly  Tyr  Glu  Asp  Val  Ile  Pro
 1              5                        10                       15
```

Glu Ala Asp Arg
                20

( 2 ) INFORMATION FOR SEQ ID NO:18:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:18:

Lys Glu Phe Gln Asn Asn Pro Asn Pro Arg Ser Leu
 1           5                       10

( 2 ) INFORMATION FOR SEQ ID NO:19:

( i ) SEQUENCE CHARACTERISTICS:
  ( A ) LENGTH: 18 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:19:

Gly Thr Gln Thr Gly Ser Ser Ser Ser Phe Glu His Glu Met Ser Gln
 1           5                       10                      15

Glu Gly ( 2 ) INFORMATION FOR SEQ ID NO:20:

( i ) SEQUENCE CHARACTERISTICS:
  ( A ) LENGTH: 23 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:20:

Ser Asn Leu Arg Gln Gln Pro Gln Lys Phe Pro Glu Ala Leu Arg Gly
 1           5                       10                      15

Cys Pro Gln Glu Asp Ser Asp
                20

( 2 ) INFORMATION FOR SEQ ID NO:21:

( i ) SEQUENCE CHARACTERISTICS:
  ( A ) LENGTH: 16 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:21:

Arg Gln Asn Thr Gly Met Trp Glu Ser Asn Ala Asn Val Lys Gly Thr
 1           5                       10                      15

( 2 ) INFORMATION FOR SEQ ID NO:22:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:22:

```
Thr  Ser  Gly  Ser  Gly  Ile  Ser  Pro  Ser  His  Ser  Gln  Arg  Ile  Ala
 1              5                        10                        15
```

(2) INFORMATION FOR SEQ ID NO:23:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:23:

```
Asn  Gln  Arg  Gly  Ser  Leu  Tyr  Gln  Cys  Asp  Tyr  Ser  Thr  Gly  Ser  Cys
 1              5                        10                        15

Glu  Pro  Ile  Arg
              20
```

(2) INFORMATION FOR SEQ ID NO:24:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:24:

```
Pro  Arg  Gly  Arg  Ala  Arg  Trp  Gln  Cys
 1              5
```

(2) INFORMATION FOR SEQ ID NO:25:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:25:

```
Lys  Leu  Ser  Pro  Arg  Leu  Gln  Tyr  Phe  Gly  Gln  Ser  Leu  Ser  Gly  Gly
 1              5                        10                        15

Gln  Asp  Leu  Thr
              20
```

(2) INFORMATION FOR SEQ ID NO:26:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:26:

```
Gln  Lys  Ser  Thr  Arg  Asp  Arg  Leu  Arg  Glu  Gly  Gln
 1              5                        10
```

(2) INFORMATION FOR SEQ ID NO:27:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:27:

```
Ser  Gly  Arg  Pro  His  Ser  Arg  Ala  Val  Phe  Asn  Glu  Thr  Lys  Asn  Ser
 1              5                         10                        15

Thr  Arg  Arg  Gln  Thr  Gln
                20
```

(2) INFORMATION FOR SEQ ID NO:28:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:28:

```
Cys  Glu  Thr  Leu  Lys  Leu  Gln  Leu  Pro  Asn  Cys  Ile  Glu  Asp  Pro  Val
 1              5                         10                        15
```

(2) INFORMATION FOR SEQ ID NO:29:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:29:

```
Phe  Glu  Lys  Asn  Cys  Gly  Asn  Asp  Asn  Ile  Cys  Gln  Asp  Asp  Leu
 1              5                         10                        15
```

(2) INFORMATION FOR SEQ ID NO:30:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:30:

```
Val  Arg  Asn  Asp  Gly  Glu  Asp  Ser  Tyr  Arg  Thr  Gln
 1              5                         10
```

(2) INFORMATION FOR SEQ ID NO:31:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:31:

```
Ser  Tyr  Arg  Lys  Val  Ser  Thr  Leu  Gln  Asn  Gln  Arg  Ser  Gln  Arg  Ser
 1              5                         10                        15
```

(2) INFORMATION FOR SEQ ID NO:32:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:32:

```
Asp  Ile  Ala  Phe  Leu  Ile  Asp  Gly  Ser
```

(2) INFORMATION FOR SEQ ID NO:33:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:33:

```
Phe  Arg  Arg  Met  Lys  Glu  Phe  Val  Ser
 1                   5
```

(2) INFORMATION FOR SEQ ID NO:34:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:34:

```
Phe  Lys  Ile  Leu  Val  Val  Ile  Thr  Asp  Gly  Glu
 1                   5                        10
```

(2) INFORMATION FOR SEQ ID NO:35:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:35:

```
Val  Ile  Arg  Tyr  Val  Ile  Gly  Val  Gly  Asp  Ala
 1                   5                        10
```

(2) INFORMATION FOR SEQ ID NO:36:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:36:

```
Asp  Gly  Glu  Lys  Phe  Gly  Asp  Pro  Leu  Gly
 1                   5                        10
```

(2) INFORMATION FOR SEQ ID NO:37:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:37:

```
Tyr  Glu  Asp  Val  Ile  Pro  Glu  Ala  Asp  Arg
 1                   5                        10
```

(2) INFORMATION FOR SEQ ID NO:38:

```
           ( i ) SEQUENCE CHARACTERISTICS:
                   ( A ) LENGTH: 27 amino acids
                   ( B ) TYPE: amino acid
                   ( D ) TOPOLOGY: linear ( i i ) MOLECULE TYPE: peptide ( x i ) SEQUENCE DESCRIPTION: SEQ ID NO:38:

Tyr   Tyr   Glu   Gln   Thr   Arg   Gly   Gly   Gln   Val   Ser   Val   Ser   Val   Cys   Pro
 1                       5                           10                            15

Arg   Gly   Arg   Ala   Arg   Trp   Gln   Cys   Asp   Ala   Tyr
                  20                         25

( 2 ) INFORMATION FOR SEQ ID NO:39:

( i ) SEQUENCE CHARACTERISTICS:
                   ( A ) LENGTH: 5138 base pairs
                   ( B ) TYPE: nucleic acid
                   ( C ) STRANDEDNESS: single
                   ( D ) TOPOLOGY: linear ( i i ) MOLECULE TYPE: cDNA ( i x ) FEATURE:
                   ( A ) NAME/KEY: Coding Sequence
                   ( B ) LOCATION: 95...3604

( x i ) SEQUENCE DESCRIPTION: SEQ ID NO:39:
```

| | | | | | |
|---|---|---|---|---|---|
| GAATTCCCTC | TTTCACCCTG | TCTAGGTTGC | CAGCAAATCC | CACGGGCCTC | CTGACGCTGC    60 |
| CCCTGGGGCC | ACAGGTCCCT | CGAGTGCTGG | AAGG ATG AAG GAT TCC TGC ATC ACT | | 115 |
| | | | Met Lys Asp Ser Cys Ile Thr | | |
| | | | 1 5 | | |

```
GTG  ATG  GCC  ATG  GCG  CTG  CTG  TCT  GGG  TTC  TTT  TTC  TTC  GCG  CCG  GCC              163
Val  Met  Ala  Met  Ala  Leu  Leu  Ser  Gly  Phe  Phe  Phe  Phe  Ala  Pro  Ala
               10                       15                            20

TCG  AGC  TAC  AAC  CTG  GAC  GTG  CGG  GGC  GCG  CGG  AGC  TTC  TCC  CCA  CCG              211
Ser  Ser  Tyr  Asn  Leu  Asp  Val  Arg  Gly  Ala  Arg  Ser  Phe  Ser  Pro  Pro
          25                       30                        35

CGC  GCC  GGG  AGG  CAC  TTT  GGA  TAC  CGC  GTC  CTG  CAG  GTC  GGA  AAC  GGG              259
Arg  Ala  Gly  Arg  His  Phe  Gly  Tyr  Arg  Val  Leu  Gln  Val  Gly  Asn  Gly
 40                        45                        50                        55

GTC  ATC  GTG  GGA  GCT  CCA  GGG  GAG  GGG  AAC  AGC  ACA  GGA  AGC  CTC  TAT              307
Val  Ile  Val  Gly  Ala  Pro  Gly  Glu  Gly  Asn  Ser  Thr  Gly  Ser  Leu  Tyr
                    60                        65                        70

CAG  TGC  CAG  TCG  GGC  ACA  GGA  CAC  TGC  CTG  CCA  GTC  ACC  CTG  AGA  GGT              355
Gln  Cys  Gln  Ser  Gly  Thr  Gly  His  Cys  Leu  Pro  Val  Thr  Leu  Arg  Gly
               75                        80                       85

TCC  AAC  TAT  ACC  TCC  AAG  TAC  TTG  GGA  ATG  ACC  TTG  GCA  ACA  GAC  CCC              403
Ser  Asn  Tyr  Thr  Ser  Lys  Tyr  Leu  Gly  Met  Thr  Leu  Ala  Thr  Asp  Pro
          90                        95                       100

ACA  GAT  GGA  AGC  ATT  TTG  GCC  TGT  GAC  CCT  GGG  CTG  TCT  CGA  ACG  TGT              451
Thr  Asp  Gly  Ser  Ile  Leu  Ala  Cys  Asp  Pro  Gly  Leu  Ser  Arg  Thr  Cys
     105                       110                       115

GAC  CAG  AAC  ACC  TAT  CTG  AGT  GGC  CTG  TGT  TAC  CTC  TTC  CGC  CAG  AAT              499
Asp  Gln  Asn  Thr  Tyr  Leu  Ser  Gly  Leu  Cys  Tyr  Leu  Phe  Arg  Gln  Asn
120                       125                       130                       135

CTG  CAG  GGT  CCC  ATG  CTG  CAG  GGG  CGC  CCT  GGT  TTT  CAG  GAA  TGT  ATC              547
Leu  Gln  Gly  Pro  Met  Leu  Gln  Gly  Arg  Pro  Gly  Phe  Gln  Glu  Cys  Ile
                    140                      145                      150

AAG  GGC  AAC  GTA  GAC  CTG  GTA  TTT  CTG  TTT  GAT  GGT  TCG  ATG  AGC  TTG              595
Lys  Gly  Asn  Val  Asp  Leu  Val  Phe  Leu  Phe  Asp  Gly  Ser  Met  Ser  Leu
                    155                      160                      165

CAG  CCA  GAT  GAA  TTT  CAG  AAA  ATT  CTG  GAC  TTC  ATG  AAG  GAT  GTG  ATG              643
Gln  Pro  Asp  Glu  Phe  Gln  Lys  Ile  Leu  Asp  Phe  Met  Lys  Asp  Val  Met
```

|  |  |  |  |  |  |  |  |  |  |  |  |  |  |  |  |  |
|---|---|---|---|---|---|---|---|---|---|---|---|---|---|---|---|---|
|  |  |  | 170 |  |  |  | 175 |  |  |  |  | 180 |  |  |  |  |
| AAG | AAA | CTC | AGC | AAC | ACT | TCG | TAC | CAG | TTT | GCT | GCT | GTT | CAG | TTT | TCC | 691 |
| Lys | Lys | Leu | Ser | Asn | Thr | Ser | Tyr | Gln | Phe | Ala | Ala | Val | Gln | Phe | Ser |  |
|  | 185 |  |  |  |  | 190 |  |  |  |  | 195 |  |  |  |  |  |
| ACA | AGC | TAC | AAA | ACA | GAA | TTT | GAT | TTC | TCA | GAT | TAT | GTT | AAA | TGG | AAG | 739 |
| Thr | Ser | Tyr | Lys | Thr | Glu | Phe | Asp | Phe | Ser | Asp | Tyr | Val | Lys | Trp | Lys |  |
| 200 |  |  |  |  | 205 |  |  |  |  | 210 |  |  |  |  | 215 |  |
| GAC | CCT | GAT | GCT | CTG | CTG | AAG | CAT | GTA | AAG | CAC | ATG | TTG | CTG | TTG | ACC | 787 |
| Asp | Pro | Asp | Ala | Leu | Leu | Lys | His | Val | Lys | His | Met | Leu | Leu | Leu | Thr |  |
|  |  |  |  | 220 |  |  |  |  | 225 |  |  |  |  |  | 230 |  |
| AAT | ACC | TTT | GGT | GCC | ATC | AAT | TAT | GTC | GCG | ACA | GAG | GTG | TTC | CGG | GAG | 835 |
| Asn | Thr | Phe | Gly | Ala | Ile | Asn | Tyr | Val | Ala | Thr | Glu | Val | Phe | Arg | Glu |  |
|  |  |  | 235 |  |  |  |  | 240 |  |  |  |  | 245 |  |  |  |
| GAG | CTG | GGG | GCC | CGG | CCA | GAT | GCC | ACC | AAA | GTG | CTT | ATC | ATC | ATC | ACG | 883 |
| Glu | Leu | Gly | Ala | Arg | Pro | Asp | Ala | Thr | Lys | Val | Leu | Ile | Ile | Ile | Thr |  |
|  |  | 250 |  |  |  |  | 255 |  |  |  |  |  | 260 |  |  |  |
| GAT | GGG | GAG | GCC | ACT | GAC | AGT | GGC | AAC | ATC | GAT | GCG | GCC | AAA | GAC | ATC | 931 |
| Asp | Gly | Glu | Ala | Thr | Asp | Ser | Gly | Asn | Ile | Asp | Ala | Ala | Lys | Asp | Ile |  |
|  | 265 |  |  |  |  | 270 |  |  |  |  | 275 |  |  |  |  |  |
| ATC | CGC | TAC | ATC | ATC | GGG | ATT | GGA | AAG | CAT | TTT | CAG | ACC | AAG | GAG | AGT | 979 |
| Ile | Arg | Tyr | Ile | Ile | Gly | Ile | Gly | Lys | His | Phe | Gln | Thr | Lys | Glu | Ser |  |
| 280 |  |  |  |  | 285 |  |  |  |  | 290 |  |  |  |  | 295 |  |
| CAG | GAG | ACC | CTC | CAC | AAA | TTT | GCA | TCA | AAA | CCC | GCG | AGC | GAG | TTT | GTG | 1027 |
| Gln | Glu | Thr | Leu | His | Lys | Phe | Ala | Ser | Lys | Pro | Ala | Ser | Glu | Phe | Val |  |
|  |  |  |  | 300 |  |  |  |  | 305 |  |  |  |  | 310 |  |  |
| AAA | ATT | CTG | GAC | ACA | TTT | GAG | AAG | CTG | AAA | GAT | CTA | TTC | ACT | GAG | CTG | 1075 |
| Lys | Ile | Leu | Asp | Thr | Phe | Glu | Lys | Leu | Lys | Asp | Leu | Phe | Thr | Glu | Leu |  |
|  |  |  | 315 |  |  |  |  | 320 |  |  |  |  | 325 |  |  |  |
| CAG | AAG | AAG | ATC | TAT | GTC | ATT | GAG | GGC | ACA | AGC | AAA | CAG | GAC | CTG | ACT | 1123 |
| Gln | Lys | Lys | Ile | Tyr | Val | Ile | Glu | Gly | Thr | Ser | Lys | Gln | Asp | Leu | Thr |  |
|  |  | 330 |  |  |  |  | 335 |  |  |  |  | 340 |  |  |  |  |
| TCC | TTC | AAC | ATG | GAG | CTG | TCC | TCC | AGC | GGC | ATC | AGT | GCT | GAC | CTC | AGC | 1171 |
| Ser | Phe | Asn | Met | Glu | Leu | Ser | Ser | Ser | Gly | Ile | Ser | Ala | Asp | Leu | Ser |  |
|  | 345 |  |  |  |  | 350 |  |  |  |  | 355 |  |  |  |  |  |
| AGG | GGC | CAT | GCA | GTC | GTG | GGG | GCA | GTA | GGA | GCC | AAG | GAC | TGG | GCT | GGG | 1219 |
| Arg | Gly | His | Ala | Val | Val | Gly | Ala | Val | Gly | Ala | Lys | Asp | Trp | Ala | Gly |  |
| 360 |  |  |  |  | 365 |  |  |  |  | 370 |  |  |  |  | 375 |  |
| GGC | TTT | CTT | GAC | CTG | AAG | GCA | GAC | CTG | CAG | GAT | GAC | ACA | TTT | ATT | GGG | 1267 |
| Gly | Phe | Leu | Asp | Leu | Lys | Ala | Asp | Leu | Gln | Asp | Asp | Thr | Phe | Ile | Gly |  |
|  |  |  |  | 380 |  |  |  |  | 385 |  |  |  |  |  | 390 |  |
| AAT | GAA | CCA | TTG | ACA | CCA | GAA | GTG | AGA | GCA | GGC | TAT | TTG | GGT | TAC | ACC | 1315 |
| Asn | Glu | Pro | Leu | Thr | Pro | Glu | Val | Arg | Ala | Gly | Tyr | Leu | Gly | Tyr | Thr |  |
|  |  |  | 395 |  |  |  |  | 400 |  |  |  |  | 405 |  |  |  |
| GTG | ACC | TGG | CTG | CCC | TCC | CGG | CAA | AAG | ACT | TCG | TTG | CTG | GCC | TCG | GGA | 1363 |
| Val | Thr | Trp | Leu | Pro | Ser | Arg | Gln | Lys | Thr | Ser | Leu | Leu | Ala | Ser | Gly |  |
|  |  | 410 |  |  |  |  | 415 |  |  |  |  | 420 |  |  |  |  |
| GCC | CCT | CGA | TAC | CAG | CAC | ATG | GGC | CGA | GTG | CTG | CTG | TTC | CAA | GAG | CCA | 1411 |
| Ala | Pro | Arg | Tyr | Gln | His | Met | Gly | Arg | Val | Leu | Leu | Phe | Gln | Glu | Pro |  |
|  | 425 |  |  |  |  | 430 |  |  |  |  | 435 |  |  |  |  |  |
| CAG | GGC | GGA | GGA | CAC | TGG | AGC | CAG | GTC | CAG | ACA | ATC | CAT | GGG | ACC | CAG | 1459 |
| Gln | Gly | Gly | Gly | His | Trp | Ser | Gln | Val | Gln | Thr | Ile | His | Gly | Thr | Gln |  |
| 440 |  |  |  |  | 445 |  |  |  |  | 450 |  |  |  |  | 455 |  |
| ATT | GGC | TCT | TAT | TTC | GGT | GGG | GAG | CTG | TGT | GGC | GTC | GAC | GTG | GAC | CAA | 1507 |
| Ile | Gly | Ser | Tyr | Phe | Gly | Gly | Glu | Leu | Cys | Gly | Val | Asp | Val | Asp | Gln |  |
|  |  |  |  | 460 |  |  |  |  | 465 |  |  |  |  | 470 |  |  |
| GAT | GGG | GAG | ACA | GAG | CTG | CTG | CTG | ATT | GGT | GCC | CCA | CTG | TTC | TAT | GGG | 1555 |
| Asp | Gly | Glu | Thr | Glu | Leu | Leu | Leu | Ile | Gly | Ala | Pro | Leu | Phe | Tyr | Gly |  |
|  |  |  | 475 |  |  |  |  | 480 |  |  |  |  | 485 |  |  |  |
| GAG | CAG | AGA | GGA | GGC | CGG | GTG | TTT | ATC | TAC | CAG | AGA | AGA | CAG | TTG | GGG | 1603 |
| Glu | Gln | Arg | Gly | Gly | Arg | Val | Phe | Ile | Tyr | Gln | Arg | Arg | Gln | Leu | Gly |  |

```
                    490                          495                          500
TTT GAA GAA GTC TCA GAG CTG CAG GGG GAC CCC GGC TAC CCA CTC GGG        1651
Phe Glu Glu Val Ser Glu Leu Gln Gly Asp Pro Gly Tyr Pro Leu Gly
    505                 510                 515

CGG TTT GGA GAA GCC ATC ACT GCT CTG ACA GAC ATC AAC GGC GAT GGG        1699
Arg Phe Gly Glu Ala Ile Thr Ala Leu Thr Asp Ile Asn Gly Asp Gly
520                 525                 530                 535

CTG GTA GAC GTG GCT GTG GGG GCC CCT CTG GAG GAG CAG GGG GCT GTG        1747
Leu Val Asp Val Ala Val Gly Ala Pro Leu Glu Glu Gln Gly Ala Val
                540                 545                 550

TAC ATC TTC AAT GGG AGG CAC GGG GGC TTA AGT CCC CAG CCA AGT CAG        1795
Tyr Ile Phe Asn Gly Arg His Gly Leu Ser Pro Gln Pro Ser Gln
        555                 560                 565

CGG ATA GAA GGG ACC CAA GTG CTC TCA GGA ATT CAG TGG TTT GGA CGC        1843
Arg Ile Glu Gly Thr Gln Val Leu Ser Gly Ile Gln Trp Phe Gly Arg
            570                 575                 580

TCC ATC CAT GGG GTG AAG GAC CTT GAA GGG GAT GGC CTG GCA GAT GTG        1891
Ser Ile His Gly Val Lys Asp Leu Glu Gly Asp Gly Leu Ala Asp Val
    585                 590                 595

GCT GTG GGG GCT GAG AGC CAG ATG ATC GTG CTG AGC TCC CGG CCC GTG        1939
Ala Val Gly Ala Glu Ser Gln Met Ile Val Leu Ser Ser Arg Pro Val
600                 605                 610                 615

GTG GAT ATG GTC ACC CTG ATG TCC TTC TCT CCA GCT GAG ATC CCA GTG        1987
Val Asp Met Val Thr Leu Met Ser Phe Ser Pro Ala Glu Ile Pro Val
                620                 625                 630

CAT GAA GTG GAG TCG TCC TAT TCA ACC AGT AAC AAG ATG AAA GAA GGA        2035
His Glu Val Glu Ser Ser Tyr Ser Thr Ser Asn Lys Met Lys Glu Gly
        635                 640                 645

GTT AAT ATC ACA ATC TGT TTC CAG ATC AAG TCT CTC TAC CCC CAG TTC        2083
Val Asn Ile Thr Ile Cys Phe Gln Ile Lys Ser Leu Tyr Pro Gln Phe
            650                 655                 660

CAA GGC CGC CTG GTT GCC AAT CTC ACT TAC ACT CTG CAG CTG GAT GGC        2131
Gln Gly Arg Leu Val Ala Asn Leu Thr Tyr Thr Leu Gln Leu Asp Gly
    665                 670                 675

CAC CGG ACC AGA AGA CGG GGG TTG TTC CCA GGA GGG AGA CAT GAA CTC        2179
His Arg Thr Arg Arg Arg Gly Leu Phe Pro Gly Gly Arg His Glu Leu
680                 685                 690                 695

AGA AGG AAT ATA GCT GTC ACC ACC AGC ATG TCA TGC ACT GAC TTC TCA        2227
Arg Arg Asn Ile Ala Val Thr Thr Ser Met Ser Cys Thr Asp Phe Ser
                700                 705                 710

TTT CAT TTC CCG GTA TGT GTT CAA GAC CTC ATC TCC CCC ATC AAT GTT        2275
Phe His Phe Pro Val Cys Val Gln Asp Leu Ile Ser Pro Ile Asn Val
        715                 720                 725

TCC CTG AAT TTC TCT CTT TGG GAG GAG GAA GGG ACA CCG AGG GAC CAA        2323
Ser Leu Asn Phe Ser Leu Trp Glu Glu Glu Gly Thr Pro Arg Asp Gln
            730                 735                 740

AGG GCG CAG GGC AAG GAC ATA CCG CCC ATC CTG AGA CCC TCC CTG CAC        2371
Arg Ala Gln Gly Lys Asp Ile Pro Pro Ile Leu Arg Pro Ser Leu His
    745                 750                 755

TCG GAA ACC TGG GAG ATC CCT TTT GAG AAG AAC TGT GGG GAG GAC AAG        2419
Ser Glu Thr Trp Glu Ile Pro Phe Glu Lys Asn Cys Gly Glu Asp Lys
760                 765                 770                 775

AAG TGT GAG GCA AAC TTG AGA GTG TCC TTC TCT CCT GCA AGA TCC AGA        2467
Lys Cys Glu Ala Asn Leu Arg Val Ser Phe Ser Pro Ala Arg Ser Arg
                780                 785                 790

GCC CTG CGT CTA ACT GCT TTT GCC AGC CTC TCT GTG GAG CTG AGC CTG        2515
Ala Leu Arg Leu Thr Ala Phe Ala Ser Leu Ser Val Glu Leu Ser Leu
        795                 800                 805

AGT AAC TTG GAA GAA GAT GCT TAC TGG GTC CAG CTG GAC CTG CAC TTC        2563
Ser Asn Leu Glu Glu Asp Ala Tyr Trp Val Gln Leu Asp Leu His Phe
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 810 |     |     |     |     | 815 |     |     |     |     |     | 820 |     |     |      |
| CCC | CCG | GGA | CTC | TCC | TTC | CGC | AAG | GTG | GAG | ATG | CTG | AAG | CCC | CAT | AGC | 2611 |
| Pro | Pro | Gly | Leu | Ser | Phe | Arg | Lys | Val | Glu | Met | Leu | Lys | Pro | His | Ser |      |
|     | 825 |     |     |     |     | 830 |     |     |     |     | 835 |     |     |     |     |      |
| CAG | ATA | CCT | GTG | AGC | TGC | GAG | GAG | CTT | CCT | GAA | GAG | TCC | AGG | CTT | CTG | 2659 |
| Gln | Ile | Pro | Val | Ser | Cys | Glu | Glu | Leu | Pro | Glu | Glu | Ser | Arg | Leu | Leu |      |
| 840 |     |     |     |     | 845 |     |     |     |     | 850 |     |     |     |     | 855 |      |
| TCC | AGG | GCA | TTA | TCT | TGC | AAT | GTG | AGC | TCT | CCC | ATC | TTC | AAA | GCA | GGC | 2707 |
| Ser | Arg | Ala | Leu | Ser | Cys | Asn | Val | Ser | Ser | Pro | Ile | Phe | Lys | Ala | Gly |      |
|     |     |     |     | 860 |     |     |     |     | 865 |     |     |     |     |     | 870 |      |
| CAC | TCG | GTT | GCT | CTG | CAG | ATG | ATG | TTT | AAT | ACA | CTG | GTA | AAC | AGC | TCC | 2755 |
| His | Ser | Val | Ala | Leu | Gln | Met | Met | Phe | Asn | Thr | Leu | Val | Asn | Ser | Ser |      |
|     |     |     | 875 |     |     |     |     | 880 |     |     |     |     |     | 885 |     |      |
| TGG | GGG | GAC | TCG | GTT | GAA | TTG | CAC | GCC | AAT | GTG | ACC | TGT | AAC | AAT | GAG | 2803 |
| Trp | Gly | Asp | Ser | Val | Glu | Leu | His | Ala | Asn | Val | Thr | Cys | Asn | Asn | Glu |      |
|     |     | 890 |     |     |     |     | 895 |     |     |     |     | 900 |     |     |     |      |
| GAC | TCA | GAC | CTC | CTG | GAG | GAC | AAC | TCA | GCC | ACT | ACC | ATC | ATC | CCC | ATC | 2851 |
| Asp | Ser | Asp | Leu | Leu | Glu | Asp | Asn | Ser | Ala | Thr | Thr | Ile | Ile | Pro | Ile |      |
|     | 905 |     |     |     |     | 910 |     |     |     |     | 915 |     |     |     |     |      |
| CTG | TAC | CCC | ATC | AAC | ATC | CTC | ATC | CAG | GAC | CAA | GAA | GAC | TCC | ACA | CTC | 2899 |
| Leu | Tyr | Pro | Ile | Asn | Ile | Leu | Ile | Gln | Asp | Gln | Glu | Asp | Ser | Thr | Leu |      |
| 920 |     |     |     |     | 925 |     |     |     |     | 930 |     |     |     |     | 935 |      |
| TAT | GTC | AGT | TTC | ACC | CCC | AAA | GGC | CCC | AAG | ATC | CAC | CAA | GTC | AAG | CAC | 2947 |
| Tyr | Val | Ser | Phe | Thr | Pro | Lys | Gly | Pro | Lys | Ile | His | Gln | Val | Lys | His |      |
|     |     |     |     | 940 |     |     |     |     | 945 |     |     |     |     | 950 |     |      |
| ATG | TAC | CAG | GTG | AGG | ATC | CAG | CCT | TCC | ATC | CAC | GAC | CAC | AAC | ATA | CCC | 2995 |
| Met | Tyr | Gln | Val | Arg | Ile | Gln | Pro | Ser | Ile | His | Asp | His | Asn | Ile | Pro |      |
|     |     |     | 955 |     |     |     |     | 960 |     |     |     |     | 965 |     |     |      |
| ACC | CTG | GAG | GCT | GTG | GTT | GGG | GTG | CCA | CAG | CCT | CCC | AGC | GAG | GGG | CCC | 3043 |
| Thr | Leu | Glu | Ala | Val | Val | Gly | Val | Pro | Gln | Pro | Pro | Ser | Glu | Gly | Pro |      |
|     |     | 970 |     |     |     |     | 975 |     |     |     |     | 980 |     |     |     |      |
| ATC | ACA | CAC | CAG | TGG | AGC | GTG | CAG | ATG | GAG | CCT | CCC | GTG | CCC | TGC | CAC | 3091 |
| Ile | Thr | His | Gln | Trp | Ser | Val | Gln | Met | Glu | Pro | Pro | Val | Pro | Cys | His |      |
| 985 |     |     |     |     | 990 |     |     |     |     | 995 |     |     |     |     |     |      |
| TAT | GAG | GAT | CTG | GAG | AGG | CTC | CCG | GAT | GCA | GCT | GAG | CCT | TGT | CTC | CCC | 3139 |
| Tyr | Glu | Asp | Leu | Glu | Arg | Leu | Pro | Asp | Ala | Ala | Glu | Pro | Cys | Leu | Pro |      |
| 1000 |    |     |     |     | 1005 |   |     |     |     | 1010 |   |     |     |     | 1015 |    |
| GGA | GCC | CTG | TTC | CGC | TGC | CCT | GTT | GTC | TTC | AGG | CAG | GAG | ATC | CTC | GTC | 3187 |
| Gly | Ala | Leu | Phe | Arg | Cys | Pro | Val | Val | Phe | Arg | Gln | Glu | Ile | Leu | Val |      |
|     |     |     |     | 1020 |   |     |     |     | 1025 |   |     |     |     | 1030 |   |      |
| CAA | GTG | ATC | GGG | ACT | CTG | GAG | CTG | GTG | GGA | GAG | ATC | GAG | GCC | TCT | TCC | 3235 |
| Gln | Val | Ile | Gly | Thr | Leu | Glu | Leu | Val | Gly | Glu | Ile | Glu | Ala | Ser | Ser |      |
|     |     |     | 1035 |   |     |     |     | 1040 |   |     |     |     | 1045 |   |     |      |
| ATG | TTC | AGC | CTC | TGC | AGC | TCC | CTC | TCC | ATC | TCC | TTC | AAC | AGC | AGC | AAG | 3283 |
| Met | Phe | Ser | Leu | Cys | Ser | Ser | Leu | Ser | Ile | Ser | Phe | Asn | Ser | Ser | Lys |      |
|     |     | 1050 |   |     |     |     | 1055 |   |     |     |     | 1060 |   |     |     |      |
| CAT | TTC | CAC | CTC | TAT | GGC | AGC | AAC | GCC | TCC | CTG | GCC | CAG | GTT | GTC | ATG | 3331 |
| His | Phe | His | Leu | Tyr | Gly | Ser | Asn | Ala | Ser | Leu | Ala | Gln | Val | Val | Met |      |
|     | 1065 |   |     |     |     | 1070 |   |     |     |     | 1075 |   |     |     |     |      |
| AAG | GTT | GAC | GTG | GTG | TAT | GAG | AAG | CAG | ATG | CTC | TAC | CTC | TAC | GTG | CTG | 3379 |
| Lys | Val | Asp | Val | Val | Tyr | Glu | Lys | Gln | Met | Leu | Tyr | Leu | Tyr | Val | Leu |      |
| 1080 |   |     |     |     | 1085 |   |     |     |     | 1090 |   |     |     |     | 1095 |      |
| AGC | GGC | ATC | GGG | GGG | CTG | CTG | CTG | CTG | CTG | CTC | ATT | TNC | ATA | GTG | CTG | 3427 |
| Ser | Gly | Ile | Gly | Gly | Leu | Leu | Leu | Leu | Leu | Leu | Ile | Xaa | Ile | Val | Leu |      |
|     |     |     |     | 1100 |   |     |     |     | 1105 |   |     |     |     | 1110 |   |      |
| TAC | AAG | GTT | GGT | TTC | TTC | AAA | CGG | AAC | CTG | AAG | GAG | AAG | ATG | GAG | GCT | 3475 |
| Tyr | Lys | Val | Gly | Phe | Phe | Lys | Arg | Asn | Leu | Lys | Glu | Lys | Met | Glu | Ala |      |
|     |     |     | 1115 |   |     |     |     | 1120 |   |     |     |     | 1125 |   |     |      |
| GGC | AGA | GGT | GTC | CCG | AAT | GGA | ATC | CCT | GCA | GAA | GAC | TCT | GAG | CAG | CTG | 3523 |
| Gly | Arg | Gly | Val | Pro | Asn | Gly | Ile | Pro | Ala | Glu | Asp | Ser | Glu | Gln | Leu |      |

-continued

```
                   1 1 3 0                          1 1 3 5                          1 1 4 0
GCA  TCT  GGG  CAA  GAG  GCT  GGG  GAT  CCC  GGC  TGC  CTG  AAG  CCC  CTC  CAT      3 5 7 1
Ala  Ser  Gly  Gln  Glu  Ala  Gly  Asp  Pro  Gly  Cys  Leu  Lys  Pro  Leu  His
          1 1 4 5                         1 1 5 0                       1 1 5 5

GAG  AAG  GAC  TCT  GAG  AGT  GGT  GGT  GGC  AAG  GAC  TGAGTCCAGC  CTGTGAGGTG        3 6 2 4
Glu  Lys  Asp  Ser  Glu  Ser  Gly  Gly  Gly  Lys  Asp
1 1 6 0                      1 1 6 5                       1 1 7 0

CAGAGTGCCC  AGAACTGGAC  TCAGGATGCC  CAGGGCCACT  TCGCCTCTGC  CTGCATTCTG               3 6 8 4

CCGTGTGCCC  TCGGGCGAGT  CACTGCCTCT  CCCTGGCCCT  CAGTTTCCCT  ATCTCGAACA               3 7 4 4

TGGAACTCAT  TCCTGAATGT  CTCCTTTGCA  GGCTCATAGG  GAAGACCTGC  TGAGGGACCA               3 8 0 4

GCCAAGAGGG  CTGCAAAAGT  GAGGGCTTGT  CATTACCAGA  CGGTTCACCA  GCCTCTCTTG               3 8 6 4

GTTCCTTCCT  TGGAAGAGAA  TGTCTGATCT  AAATGTGGAG  AAACTGTAGT  CTCAGGACCT               3 9 2 4

AGGGATGTTC  TGGCCCTCAC  CCCTGCCCTG  GATGTCCAC   AGATGCCTCC  ACCCCCAGA                3 9 8 4

ACCTGTCCTT  GCACACTCCC  CTGCACTGGA  GTCCAGTCTC  TTCTGCTGGC  AGAAAGCAAA               4 0 4 4

TGTGACCTGT  GTCACTACGT  GACTGTGGCA  CACGCCTTGT  TCTTGGCCAA  AGACCAAATT               4 1 0 4

CCTTGGCATG  CCTTCCAGCA  CCCTGCAAAA  TGAGACCCTC  GTGGCTTCC   CCAGCCTCTT               4 1 6 4

CTAGAGCCGT  GATGCCTCCC  TGTTGAAGCT  CTGGTGACAC  CAGCCTTTCT  CCCAGGCCAG               4 2 2 4

GCTCCTTCCT  GTCTTCCTGC  ATTCACCCAG  ACAGCTCCCT  CTGCCTGAAC  CTTCCATCTC               4 2 8 4

GCCCACCCCT  CCTTCCTTGA  CCAGCAGATC  CCAGCTCACG  TCACACACTT  GGTTGGGTCC               4 3 4 4

TCACATCTTT  CACACTTCCA  CCACCCTGCA  CTACTCCCTC  AAAGCACACG  TCATGTTTCT               4 4 0 4

TCATCCGGCA  GCCTGGATGT  TTTTTCCCTG  TTTAATGATT  GACGTACTTA  GCAGCTATCT               4 4 6 4

CTCAGTGAAC  TGTGAGGGTA  AAGGCTATAC  TTGTCTTGTT  CACCTTGGGA  TGACGCCGCA               4 5 2 4

TGATATGTCA  GGGCGTGGGA  CATCTAGTAG  GTGCTTGACA  TAATTTCACT  GAATTAATGA               4 5 8 4

CAGAGCCAGT  GGGAAGATAC  AGAAAAAGAG  GGCCGGGGCT  GGGCGCGGTG  GTTCACGCCT               4 6 4 4

GTAATCCCAG  CACTTTGGGA  GGCCAAGGAG  GGTGGATCAC  CTGAGGTCAG  GAGTTAGAGG               4 7 0 4

CCAGCCTGGC  GAAACCCCAT  CTCTACTAAA  AATACAAAAT  CCAGGCGTGG  TGGCACACAC               4 7 6 4

CTGTAGTCCC  AGCTACTCAG  GAGGTTGAGG  TAGGAGAATT  GCTTGAACCT  GGGAGGTGGA               4 8 2 4

GGTTGCAGTG  AGCCAAGATT  GCGCCATTGC  ACTCCAGCCT  GGGCAACACA  GCGAGACTCC               4 8 8 4

GTCTCAAGGA  AAAAATAAAA  ATAAAAGCG   GGCACGGGCC  CGGACATCCC  CACCCTTGGA               4 9 4 4

GGCTGTCTTC  TCAGGCTCTG  CCCTGCCCTA  GCTCCACACC  CTCTCCCAGG  ACCCATCACG               5 0 0 4

CCTGTGCAGT  GGCCCCCACA  GAAAGACTGA  GCTCAAGGTG  GGAACCACGT  CTGCTAACTT               5 0 6 4

GGAGCCCCAG  TGCCAAGCAC  AGTGCCTGCA  TGTATTTATC  CAATAAATGT  GAAATTCTGT               5 1 2 4

CCAAAAAAAA  AAAA                                                                    5 1 3 8
```

( 2 ) INFORMATION FOR SEQ ID NO:40:

( i ) SEQUENCE CHARACTERISTICS:
        ( A ) LENGTH: 3533 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 75...3530

( x i ) SEQUENCE DESCRIPTION: SEQ ID NO:40:

```
TGGCTTCCTT  GTGGTTCCTC  AGTGGTGCCT  GCAACCCCTG  GTTCACCTCC  TTCCAGGTTC            6 0
```

```
TGGCCCTTCC AGCC ATG GCT CTC AGA GTC CTT CTG TTA ACA GCC TTG ACC            110
               Met Ala Leu Arg Val Leu Leu Leu Thr Ala Leu Thr
                 1           5                      10

TTA TGT CAT GGG TTC AAC TTG GAC ACT GAA AAC GCA ATG ACC TTC CAA            158
Leu Cys His Gly Phe Asn Leu Asp Thr Glu Asn Ala Met Thr Phe Gln
            15                  20                  25

GAG AAC GCA AGG GGC TTC GGG CAG AGC GTG GTC CAG CTT CAG GGA TCC            206
Glu Asn Ala Arg Gly Phe Gly Gln Ser Val Val Gln Leu Gln Gly Ser
            30                  35                  40

AGG GTG GTG GTT GGA GCC CCC CAG GAG ATA GTG GCT GCC AAC CAA AGG            254
Arg Val Val Val Gly Ala Pro Gln Glu Ile Val Ala Ala Asn Gln Arg
 45                  50                  55                  60

GGC AGC CTC TAC CAG TGC GAC TAC AGC ACA GGC TCA TGC GAG CCC ATC            302
Gly Ser Leu Tyr Gln Cys Asp Tyr Ser Thr Gly Ser Cys Glu Pro Ile
                 65                  70                  75

CGC CTG CAG GTC CCC GTG GAG GCC GTG AAC ATG TCC CTG GGC CTG TCC            350
Arg Leu Gln Val Pro Val Glu Ala Val Asn Met Ser Leu Gly Leu Ser
             80                  85                  90

CTG GCA GCC ACC ACC AGC CCC CCT CAG CTG CTG GCC TGT GGT CCC ACC            398
Leu Ala Ala Thr Thr Ser Pro Pro Gln Leu Leu Ala Cys Gly Pro Thr
         95                 100                 105

GTG CAC CAG ACT TGC AGT GAG AAC ACG TAT GTG AAA GGG CTC TGC TTC            446
Val His Gln Thr Cys Ser Glu Asn Thr Tyr Val Lys Gly Leu Cys Phe
    110                 115                 120

CTG TTT GGA TCC AAC CTA CGG CAG CAG CCC CAG AAG TTC CCA GAG GCC            494
Leu Phe Gly Ser Asn Leu Arg Gln Gln Pro Gln Lys Phe Pro Glu Ala
125                 130                 135                 140

CTC CGA GGG TGT CCT CAA GAG GAT AGT GAC ATT GCC TTC TTG ATT GAT            542
Leu Arg Gly Cys Pro Gln Glu Asp Ser Asp Ile Ala Phe Leu Ile Asp
                145                 150                 155

GGC TCT GGT AGC ATC ATC CCA CAT GAC TTT CGG CGG ATG AAG GAG TTT            590
Gly Ser Gly Ser Ile Ile Pro His Asp Phe Arg Arg Met Lys Glu Phe
            160                 165                 170

GTC TCA ACT GTG ATG GAG CAA TTA AAA AAG TCC AAA ACC TTG TTC TCT            638
Val Ser Thr Val Met Glu Gln Leu Lys Lys Ser Lys Thr Leu Phe Ser
        175                 180                 185

TTG ATG CAG TAC TCT GAA GAA TTC CGG ATT CAC TTT ACC TTC AAA GAG            686
Leu Met Gln Tyr Ser Glu Glu Phe Arg Ile His Phe Thr Phe Lys Glu
    190                 195                 200

TTC CAG AAC AAC CCT AAC CCA AGA TCA CTG GTG AAG CCA ATA ACG CAG            734
Phe Gln Asn Asn Pro Asn Pro Arg Ser Leu Val Lys Pro Ile Thr Gln
205                 210                 215                 220

CTG CTT GGG CGG ACA CAC ACG GCC ACG GGC ATC CGC AAA GTG GTA CGA            782
Leu Leu Gly Arg Thr His Thr Ala Thr Gly Ile Arg Lys Val Val Arg
                225                 230                 235

GAG CTG TTT AAC ATC ACC AAC GGA GCC CGA AAG AAT GCC TTT AAG ATC            830
Glu Leu Phe Asn Ile Thr Asn Gly Ala Arg Lys Asn Ala Phe Lys Ile
            240                 245                 250

CTA GTT GTC ATC ACG GAT GGA GAA AAG TTT GGC GAT CCC TTG GGA TAT            878
Leu Val Val Ile Thr Asp Gly Glu Lys Phe Gly Asp Pro Leu Gly Tyr
        255                 260                 265

GAG GAT GTC ATC CCT GAG GCA GAC AGA GAG GGA GTC ATT CGC TAC GTC            926
Glu Asp Val Ile Pro Glu Ala Asp Arg Glu Gly Val Ile Arg Tyr Val
    270                 275                 280

ATT GGG GTG GGA GAT GCC TTC CGC AGT GAG AAA TCC CGC CAA GAG CTT            974
Ile Gly Val Gly Asp Ala Phe Arg Ser Glu Lys Ser Arg Gln Glu Leu
285                 290                 295                 300

AAT ACC ATC GCA TCC AAG CCG CCT CGT GAT CAC GTG TTC CAG GTG AAT           1022
Asn Thr Ile Ala Ser Lys Pro Pro Arg Asp His Val Phe Gln Val Asn
                305                 310                 315
```

| | | | | | | | | | | | | | | | | |
|---|---|---|---|---|---|---|---|---|---|---|---|---|---|---|---|---|
| AAC | TTT | GAG | GCT | CTG | AAG | ACC | ATT | CAG | AAC | CAG | CTT | CGG | GAG | AAG | ATC | 1070 |
| Asn | Phe | Glu | Ala | Leu | Lys | Thr | Ile | Gln | Asn | Gln | Leu | Arg | Glu | Lys | Ile | |
| | | | 320 | | | | | 325 | | | | | 330 | | | |
| TTT | GCG | ATC | GAG | GGT | ACT | CAG | ACA | GGA | AGT | AGC | AGC | TCC | TTT | GAG | CAT | 1118 |
| Phe | Ala | Ile | Glu | Gly | Thr | Gln | Thr | Gly | Ser | Ser | Ser | Ser | Phe | Glu | His | |
| | | 335 | | | | | 340 | | | | | 345 | | | | |
| GAG | ATG | TCT | CAG | GAA | GGC | TTC | AGC | GCT | GCC | ATC | ACC | TCT | AAT | GGC | CCC | 1166 |
| Glu | Met | Ser | Gln | Glu | Gly | Phe | Ser | Ala | Ala | Ile | Thr | Ser | Asn | Gly | Pro | |
| | 350 | | | | | 355 | | | | | 360 | | | | | |
| TTG | CTG | AGC | ACT | GTG | GGG | AGC | TAT | GAC | TGG | GCT | GGT | GGA | GTC | TTT | CTA | 1214 |
| Leu | Leu | Ser | Thr | Val | Gly | Ser | Tyr | Asp | Trp | Ala | Gly | Gly | Val | Phe | Leu | |
| 365 | | | | | 370 | | | | | 375 | | | | | 380 | |
| TAT | ACA | TCA | AAG | GAG | AAA | AGC | ACC | TTC | ATC | AAC | ATG | ACC | AGA | GTG | GAT | 1262 |
| Tyr | Thr | Ser | Lys | Glu | Lys | Ser | Thr | Phe | Ile | Asn | Met | Thr | Arg | Val | Asp | |
| | | | | 385 | | | | | 390 | | | | | 395 | | |
| TCA | GAC | ATG | AAT | GAT | GCT | TAC | TTG | GGT | TAT | GCT | GCC | GCC | ATC | ATC | TTA | 1310 |
| Ser | Asp | Met | Asn | Asp | Ala | Tyr | Leu | Gly | Tyr | Ala | Ala | Ala | Ile | Ile | Leu | |
| | | | 400 | | | | | 405 | | | | | 410 | | | |
| CGG | AAC | CGG | GTG | CAA | AGC | CTG | GTT | CTG | GGG | GCA | CCT | CGA | TAT | CAG | CAC | 1358 |
| Arg | Asn | Arg | Val | Gln | Ser | Leu | Val | Leu | Gly | Ala | Pro | Arg | Tyr | Gln | His | |
| | | 415 | | | | | 420 | | | | | 425 | | | | |
| ATC | GGC | CTG | GTA | GCG | ATG | TTC | AGG | CAG | AAC | ACT | GGC | ATG | TGG | GAG | TCC | 1406 |
| Ile | Gly | Leu | Val | Ala | Met | Phe | Arg | Gln | Asn | Thr | Gly | Met | Trp | Glu | Ser | |
| | 430 | | | | | 435 | | | | | 440 | | | | | |
| AAC | GCT | AAT | GTC | AAG | GGC | ACC | CAG | ATC | GGC | GCC | TAC | TTC | GGG | GCC | TCC | 1454 |
| Asn | Ala | Asn | Val | Lys | Gly | Thr | Gln | Ile | Gly | Ala | Tyr | Phe | Gly | Ala | Ser | |
| 445 | | | | | 450 | | | | | 455 | | | | | 460 | |
| CTC | TGC | TCC | GTG | GAC | GTG | GAC | AGC | AAC | GGC | AGC | ACC | GAC | CTG | GTC | CTC | 1502 |
| Leu | Cys | Ser | Val | Asp | Val | Asp | Ser | Asn | Gly | Ser | Thr | Asp | Leu | Val | Leu | |
| | | | 465 | | | | | 470 | | | | | 475 | | | |
| ATC | GGG | GCC | CCC | CAT | TAC | TAC | GAG | CAG | ACC | CGA | GGG | GGC | CAG | GTG | TCC | 1550 |
| Ile | Gly | Ala | Pro | His | Tyr | Tyr | Glu | Gln | Thr | Arg | Gly | Gly | Gln | Val | Ser | |
| | | | 480 | | | | | 485 | | | | | 490 | | | |
| GTG | TGC | CCC | TTG | CCC | AGG | GGG | AGG | GCT | CGG | TGG | CAG | TGT | GAT | GCT | GTT | 1598 |
| Val | Cys | Pro | Leu | Pro | Arg | Gly | Arg | Ala | Arg | Trp | Gln | Cys | Asp | Ala | Val | |
| | | 495 | | | | | 500 | | | | | 505 | | | | |
| CTC | TAC | GGG | GAG | CAG | GGC | CAA | CCC | TGG | GGC | CGC | TTT | GGG | GCA | GCC | CTA | 1646 |
| Leu | Tyr | Gly | Glu | Gln | Gly | Gln | Pro | Trp | Gly | Arg | Phe | Gly | Ala | Ala | Leu | |
| | 510 | | | | | 515 | | | | | 520 | | | | | |
| ACA | GTG | CTG | GGG | GAC | GTA | AAT | GGG | GAC | AAG | CTG | ACG | GAC | GTG | GCC | ATT | 1694 |
| Thr | Val | Leu | Gly | Asp | Val | Asn | Gly | Asp | Lys | Leu | Thr | Asp | Val | Ala | Ile | |
| 525 | | | | | 530 | | | | | 535 | | | | | 540 | |
| GGG | GCC | CCA | GGA | GAG | GAG | GAC | AAC | CGG | GGT | GCT | GTT | TAC | CTG | TTT | CAC | 1742 |
| Gly | Ala | Pro | Gly | Glu | Glu | Asp | Asn | Arg | Gly | Ala | Val | Tyr | Leu | Phe | His | |
| | | | | 545 | | | | | 550 | | | | | 555 | | |
| GGA | ACC | TCA | GGA | TCT | GGC | ATC | AGC | CCC | TCC | CAT | AGC | CAG | CGG | ATA | GCA | 1790 |
| Gly | Thr | Ser | Gly | Ser | Gly | Ile | Ser | Pro | Ser | His | Ser | Gln | Arg | Ile | Ala | |
| | | | 560 | | | | | 565 | | | | | 570 | | | |
| GGC | TCC | AAG | CTC | TCT | CCC | AGG | CTC | CAG | TAT | TTT | GGT | CAG | TCA | CTG | AGT | 1838 |
| Gly | Ser | Lys | Leu | Ser | Pro | Arg | Leu | Gln | Tyr | Phe | Gly | Gln | Ser | Leu | Ser | |
| | | 575 | | | | | 580 | | | | | 585 | | | | |
| GGG | GGC | CAG | GAC | CTC | ACA | ATG | GAT | GGA | CTG | GTA | GAC | CTG | ACT | GTA | GGA | 1886 |
| Gly | Gly | Gln | Asp | Leu | Thr | Met | Asp | Gly | Leu | Val | Asp | Leu | Thr | Val | Gly | |
| | 590 | | | | | 595 | | | | | 600 | | | | | |
| GCC | CAG | GGG | CAC | GTG | CTG | CTG | CTC | AGG | TCC | CAG | CCA | GTA | CTG | AGA | GTC | 1934 |
| Ala | Gln | Gly | His | Val | Leu | Leu | Leu | Arg | Ser | Gln | Pro | Val | Leu | Arg | Val | |
| 605 | | | | | 610 | | | | | 615 | | | | | 620 | |
| AAG | GCA | ATC | ATG | GAG | TTC | AAT | CCC | AGG | GAA | GTG | GCA | AGG | AAT | GTA | TTT | 1982 |
| Lys | Ala | Ile | Met | Glu | Phe | Asn | Pro | Arg | Glu | Val | Ala | Arg | Asn | Val | Phe | |
| | | | | 625 | | | | | 630 | | | | | 635 | | |

```
GAG TGT AAT GAT CAA GTG GTG AAA GGC AAG GAA GCC GGA GAG GTC AGA         2030
Glu Cys Asn Asp Gln Val Val Lys Gly Lys Glu Ala Gly Glu Val Arg
            640                 645                 650

GTC TGC CTC CAT GTC CAG AAG AGC ACA CGG GAT CGG CTA AGA GAA GGA         2078
Val Cys Leu His Val Gln Lys Ser Thr Arg Asp Arg Leu Arg Glu Gly
                655                 660                 665

CAG ATC CAG AGT GTT GTG ACT TAT GAC CTG GCT CTG GAC TCC GGC CGC         2126
Gln Ile Gln Ser Val Val Thr Tyr Asp Leu Ala Leu Asp Ser Gly Arg
670                 675                 680

CCA CAT TCC CGC GCC GTC TTC AAT GAG ACA AAG AAC AGC ACA CGC AGA         2174
Pro His Ser Arg Ala Val Phe Asn Glu Thr Lys Asn Ser Thr Arg Arg
685                 690                 695                 700

CAG ACA CAG GTC TTG GGG CTG ACC CAG ACT TGT GAG ACC CTG AAA CTA         2222
Gln Thr Gln Val Leu Gly Leu Thr Gln Thr Cys Glu Thr Leu Lys Leu
                                705                 710                 715

CAG TTG CCG AAT TGC ATC GAG GAC CCA GTG AGC CCC ATT GTG CTG CGC         2270
Gln Leu Pro Asn Cys Ile Glu Asp Pro Val Ser Pro Ile Val Leu Arg
                720                 725                 730

CTG AAC TTC TCT CTG GTG GGA ACG CCA TTG TCT GCT TTC GGG AAC CTC         2318
Leu Asn Phe Ser Leu Val Gly Thr Pro Leu Ser Ala Phe Gly Asn Leu
            735                 740                 745

CGG CCA GTG CTG GCG GAG GAT GCT CAG AGA CTC TTC ACA GCC TTG TTT         2366
Arg Pro Val Leu Ala Glu Asp Ala Gln Arg Leu Phe Thr Ala Leu Phe
        750                 755                 760

CCC TTT GAG AAG AAT TGT GGC AAT GAC AAC ATC TGC CAG GAT GAC CTC         2414
Pro Phe Glu Lys Asn Cys Gly Asn Asp Asn Ile Cys Gln Asp Asp Leu
765                 770                 775                 780

AGC ATC ACC TTC AGT TTC ATG AGC CTG GAC TGC CTC GTG GTG GGT GGG         2462
Ser Ile Thr Phe Ser Phe Met Ser Leu Asp Cys Leu Val Val Gly Gly
                785                 790                 795

CCC CGG GAG TCT AAC GTG ACA GTG ACT GTG AGA AAT GAT GGT GAG GAC         2510
Pro Arg Glu Ser Asn Val Thr Val Thr Val Arg Asn Asp Gly Glu Asp
                800                 805                 810

TCC TAC AGG ACA CAG GTC ACC TTC TTC TTC CCG CTT GAC CTG TCC TAC         2558
Ser Tyr Arg Thr Gln Val Thr Phe Phe Phe Pro Leu Asp Leu Ser Tyr
            815                 820                 825

CGG AAG GTG TCC ACA CTC CAG AAC CAG CGC TCA CAG CGA TCC TGG CGC         2606
Arg Lys Val Ser Thr Leu Gln Asn Gln Arg Ser Gln Arg Ser Trp Arg
        830                 835                 840

CTG GCC TGT GAG TCT GCC TCC TCC ACC GAA GTG TCT GGG GCC TTG AAG         2654
Leu Ala Cys Glu Ser Ala Ser Ser Thr Glu Val Ser Gly Ala Leu Lys
845                 850                 855                 860

AGC ACC AGC TGC AGC ATA AAC CAC CCC ATC TTC CCG GAA AAC TCA GAG         2702
Ser Thr Ser Cys Ser Ile Asn His Pro Ile Phe Pro Glu Asn Ser Glu
                865                 870                 875

GTC ACC TTT AAT ATC ACG TTT GAT GTA GAC TCT AAG GCT TCC CTT GGA         2750
Val Thr Phe Asn Ile Thr Phe Asp Val Asp Ser Lys Ala Ser Leu Gly
                880                 885                 890

AAC AAA CTG CTC CTC AAG GCC AAT GTG ACC AGT GAG AAC AAC ATG CCC         2798
Asn Lys Leu Leu Leu Lys Ala Asn Val Thr Ser Glu Asn Asn Met Pro
            895                 900                 905

AGA ACC AAC AAA ACC GAA TTC CAA CTG GAG CTG CCG GTG AAA TAT GCT         2846
Arg Thr Asn Lys Thr Glu Phe Gln Leu Glu Leu Pro Val Lys Tyr Ala
        910                 915                 920

GTC TAC ATG GTG GTC ACC AGC CAT GGG GTC TCC ACT AAA TAT CTC AAC         2894
Val Tyr Met Val Val Thr Ser His Gly Val Ser Thr Lys Tyr Leu Asn
925                 930                 935                 940

TTC ACG GCC TCA GAG AAT ACC AGT CGG GTC ATG CAG CAT CAA TAT CAG         2942
Phe Thr Ala Ser Glu Asn Thr Ser Arg Val Met Gln His Gln Tyr Gln
                945                 950                 955
```

```
GTC  AGC  AAC  CTG  GGG  CAG  AGG  AGC  CCC  CCC  ATC  AGC  CTG  GTG  TTC  TTG        2990
Val  Ser  Asn  Leu  Gly  Gln  Arg  Ser  Pro  Pro  Ile  Ser  Leu  Val  Phe  Leu
              960                      965                      970

GTG  CCC  GTC  CGG  CTG  AAC  CAG  ACT  GTC  ATA  TGG  GAC  CGC  CCC  CAG  GTC        3038
Val  Pro  Val  Arg  Leu  Asn  Gln  Thr  Val  Ile  Trp  Asp  Arg  Pro  Gln  Val
         975                      980                      985

ACC  TTC  TCC  GAG  AAC  CTC  TCG  AGT  ACG  TGC  CAC  ACC  AAG  GAG  CGC  TTG        3086
Thr  Phe  Ser  Glu  Asn  Leu  Ser  Ser  Thr  Cys  His  Thr  Lys  Glu  Arg  Leu
              990                      995                      1000

CCC  TCT  CAC  TCC  GAC  TTT  CTG  GCT  GAG  CTT  CGG  AAG  GCC  CCC  GTG  GTG        3134
Pro  Ser  His  Ser  Asp  Phe  Leu  Ala  Glu  Leu  Arg  Lys  Ala  Pro  Val  Val
1005                      1010                     1015                     1020

AAC  TGC  TCC  ATC  GCT  GTC  TGC  CAG  AGA  ATC  CAG  TGT  GAC  ATC  CCG  TTC        3182
Asn  Cys  Ser  Ile  Ala  Val  Cys  Gln  Arg  Ile  Gln  Cys  Asp  Ile  Pro  Phe
                   1025                     1030                     1035

TTT  GGC  ATC  CAG  GAA  GAA  TTC  AAT  GCT  ACC  CTC  AAA  GGC  AAC  CTC  TCG        3230
Phe  Gly  Ile  Gln  Glu  Glu  Phe  Asn  Ala  Thr  Leu  Lys  Gly  Asn  Leu  Ser
                   1040                     1045                     1050

TTT  GAC  TGG  TAC  ATC  AAG  ACC  TCG  CAT  AAC  CAC  CTC  CTG  ATC  GTG  AGC        3278
Phe  Asp  Trp  Tyr  Ile  Lys  Thr  Ser  His  Asn  His  Leu  Leu  Ile  Val  Ser
                   1055                     1060                     1065

ACA  GCT  GAG  ATC  TTG  TTT  AAC  GAT  TCC  GTG  TTC  ACC  CTG  CTG  CCG  GGA        3326
Thr  Ala  Glu  Ile  Leu  Phe  Asn  Asp  Ser  Val  Phe  Thr  Leu  Leu  Pro  Gly
         1070                     1075                     1080

CAG  GGG  GCG  TTT  GTG  AGG  TCC  CAG  ACG  GAG  ACC  AAA  GTG  GAG  CCG  TTC        3374
Gln  Gly  Ala  Phe  Val  Arg  Ser  Gln  Thr  Glu  Thr  Lys  Val  Glu  Pro  Phe
1085                     1090                     1095                     1100

GAG  GTC  CCC  AAC  CCC  CTG  CCG  CTC  ATC  GTG  GGC  AGC  TCT  GTC  GGG  GGA        3422
Glu  Val  Pro  Asn  Pro  Leu  Pro  Leu  Ile  Val  Gly  Ser  Ser  Val  Gly  Gly
                   1105                     1110                     1115

CTG  CTG  CTC  CTG  GCC  CTC  ATC  ACC  GCC  GCG  CTG  TAC  AAG  CTC  GGC  TTC        3470
Leu  Leu  Leu  Leu  Ala  Leu  Ile  Thr  Ala  Ala  Leu  Tyr  Lys  Leu  Gly  Phe
                   1120                     1125                     1130

TTC  AAG  CGG  CAA  TAC  AAG  GAC  ATG  ATG  AGT  GAA  GGG  GGT  CCC  CCG  GGG        3518
Phe  Lys  Arg  Gln  Tyr  Lys  Asp  Met  Met  Ser  Glu  Gly  Gly  Pro  Pro  Gly
              1135                     1140                     1145

GCC  GAA  CCC  CAG  TAG                                                               3533
Ala  Glu  Pro  Gln
         1150
```

(2) INFORMATION FOR SEQ ID NO:41:

(i) SEQUENCE CHARACTERISTICS:
        (A) LENGTH: 2310 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...2307

(xi) SEQUENCE DESCRIPTION: SEQ ID NO:41:

```
ATG  CTG  GGC  CTG  CGC  CCC  CCA  CTT  CTC  GCC  CTG  GTG  GGG  CTG  CTC  TCC         48
Met  Leu  Gly  Leu  Arg  Pro  Pro  Leu  Leu  Ala  Leu  Val  Gly  Leu  Leu  Ser
 1                 5                      10                      15

CTC  GGG  TGC  GTC  CTC  TCT  CAG  GAG  TGC  ACG  AAG  TTC  AAG  GTC  AGC  AGC         96
Leu  Gly  Cys  Val  Leu  Ser  Gln  Glu  Cys  Thr  Lys  Phe  Lys  Val  Ser  Ser
              20                      25                      30

TGC  CGG  GAA  TGC  ATC  GAG  TCG  GGG  CCC  GGC  TGC  ACC  TGG  TGC  CAG  AAG        144
Cys  Arg  Glu  Cys  Ile  Glu  Ser  Gly  Pro  Gly  Cys  Thr  Trp  Cys  Gln  Lys
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| CTG | AAC | TTC | ACA | GGG | CCG | GGG | GAT | CCT | GAC | TCC | ATT | CGC | TGC | GAC | ACC | 192  |
| Leu | Asn | Phe | Thr | Gly | Pro | Gly | Asp | Pro | Asp | Ser | Ile | Arg | Cys | Asp | Thr |      |
|     | 50  |     |     |     | 55  |     |     |     |     | 60  |     |     |     |     |     |      |
| CGG | CCA | CAG | CTG | CTC | ATG | AGG | GGC | TGT | GCG | GCT | GAC | GAC | ATC | ATG | GAC | 240  |
| Arg | Pro | Gln | Leu | Leu | Met | Arg | Gly | Cys | Ala | Ala | Asp | Asp | Ile | Met | Asp |      |
| 65  |     |     |     |     | 70  |     |     |     |     | 75  |     |     |     |     | 80  |      |
| CCC | ACA | AGC | CTC | GCT | GAA | ACC | CAG | GAA | GAC | CAC | AAT | GGG | GGC | CAG | AAG | 288  |
| Pro | Thr | Ser | Leu | Ala | Glu | Thr | Gln | Glu | Asp | His | Asn | Gly | Gly | Gln | Lys |      |
|     |     |     |     | 85  |     |     |     |     | 90  |     |     |     |     | 95  |     |      |
| CAG | CTG | TCC | CCA | CAA | AAA | GTG | ACG | CTT | TAC | CTG | CGA | CCA | GGC | CAG | GCA | 336  |
| Gln | Leu | Ser | Pro | Gln | Lys | Val | Thr | Leu | Tyr | Leu | Arg | Pro | Gly | Gln | Ala |      |
|     |     |     | 100 |     |     |     |     | 105 |     |     |     |     | 110 |     |     |      |
| GCA | GCG | TTC | AAC | GTG | ACC | TTC | CGG | CGG | GCC | AAG | GGC | TAC | CCC | ATC | GAC | 384  |
| Ala | Ala | Phe | Asn | Val | Thr | Phe | Arg | Arg | Ala | Lys | Gly | Tyr | Pro | Ile | Asp |      |
|     |     |     | 115 |     |     |     |     | 120 |     |     |     |     | 125 |     |     |      |
| CTG | TAC | TAT | CTG | ATG | GAC | CTC | TCC | TAC | TCC | ATG | CTT | GAT | GAC | CTC | AGG | 432  |
| Leu | Tyr | Tyr | Leu | Met | Asp | Leu | Ser | Tyr | Ser | Met | Leu | Asp | Asp | Leu | Arg |      |
|     |     | 130 |     |     |     |     | 135 |     |     |     |     | 140 |     |     |     |      |
| AAT | GTC | AAG | AAG | CTA | GGT | GGC | GAC | CTG | CTC | CGG | GCC | CTC | AAC | GAG | ATC | 480  |
| Asn | Val | Lys | Lys | Leu | Gly | Gly | Asp | Leu | Leu | Arg | Ala | Leu | Asn | Glu | Ile |      |
| 145 |     |     |     |     | 150 |     |     |     |     | 155 |     |     |     |     | 160 |      |
| ACC | GAG | TCC | GGC | CGC | ATT | GGC | TTC | GGG | TCC | TTC | GTG | GAC | AAG | ACC | GTG | 528  |
| Thr | Glu | Ser | Gly | Arg | Ile | Gly | Phe | Gly | Ser | Phe | Val | Asp | Lys | Thr | Val |      |
|     |     |     |     | 165 |     |     |     |     | 170 |     |     |     |     | 175 |     |      |
| CTG | CCG | TTC | GTG | AAC | ACG | CAC | CCT | GAT | AAG | CTG | CGA | AAC | CCA | TGC | CCC | 576  |
| Leu | Pro | Phe | Val | Asn | Thr | His | Pro | Asp | Lys | Leu | Arg | Asn | Pro | Cys | Pro |      |
|     |     |     | 180 |     |     |     |     | 185 |     |     |     |     | 190 |     |     |      |
| AAC | AAG | GAG | AAA | GAG | TGC | CAG | CCC | CCG | TTT | GCC | TTC | AGG | CAC | GTG | CTG | 624  |
| Asn | Lys | Glu | Lys | Glu | Cys | Gln | Pro | Pro | Phe | Ala | Phe | Arg | His | Val | Leu |      |
|     |     | 195 |     |     |     |     | 200 |     |     |     |     | 205 |     |     |     |      |
| AAG | CTG | ACC | AAC | AAC | TCC | AAC | CAG | TTT | CAG | ACC | GAG | GTC | GGG | AAG | CAG | 672  |
| Lys | Leu | Thr | Asn | Asn | Ser | Asn | Gln | Phe | Gln | Thr | Glu | Val | Gly | Lys | Gln |      |
|     | 210 |     |     |     |     | 215 |     |     |     |     | 220 |     |     |     |     |      |
| CTG | ATT | TCC | GGA | AAC | CTG | GAT | GCA | CCC | GAG | GGT | GGG | CTG | GAC | GCC | ATG | 720  |
| Leu | Ile | Ser | Gly | Asn | Leu | Asp | Ala | Pro | Glu | Gly | Gly | Leu | Asp | Ala | Met |      |
| 225 |     |     |     |     | 230 |     |     |     |     | 235 |     |     |     |     | 240 |      |
| ATG | CAG | GTC | GCC | GCC | TGC | CCG | GAG | GAA | ATC | GGC | TGG | CGC | AAC | GTC | ACG | 768  |
| Met | Gln | Val | Ala | Ala | Cys | Pro | Glu | Glu | Ile | Gly | Trp | Arg | Asn | Val | Thr |      |
|     |     |     |     | 245 |     |     |     |     | 250 |     |     |     |     | 255 |     |      |
| CGG | CTG | CTG | GTG | TTT | GCC | ACT | GAT | GAC | GGC | TTC | CAT | TTC | GCG | GGC | GAC | 816  |
| Arg | Leu | Leu | Val | Phe | Ala | Thr | Asp | Asp | Gly | Phe | His | Phe | Ala | Gly | Asp |      |
|     |     |     | 260 |     |     |     |     | 265 |     |     |     |     | 270 |     |     |      |
| GGA | AAG | CTG | GGC | GCC | ATC | CTG | ACC | CCC | AAC | GAC | GGC | CGC | TGT | CAC | CTG | 864  |
| Gly | Lys | Leu | Gly | Ala | Ile | Leu | Thr | Pro | Asn | Asp | Gly | Arg | Cys | His | Leu |      |
|     |     | 275 |     |     |     |     | 280 |     |     |     |     | 285 |     |     |     |      |
| GAG | GAC | AAC | TTG | TAC | AAG | AGG | AGC | AAC | GAA | TTC | GAC | TAC | CCA | TCG | GTG | 912  |
| Glu | Asp | Asn | Leu | Tyr | Lys | Arg | Ser | Asn | Glu | Phe | Asp | Tyr | Pro | Ser | Val |      |
|     | 290 |     |     |     |     | 295 |     |     |     |     | 300 |     |     |     |     |      |
| GGC | CAG | CTG | GCG | CAC | AAG | CTG | GCT | GAA | AAC | AAC | ATC | CAG | CCC | ATC | TTC | 960  |
| Gly | Gln | Leu | Ala | His | Lys | Leu | Ala | Glu | Asn | Asn | Ile | Gln | Pro | Ile | Phe |      |
| 305 |     |     |     |     | 310 |     |     |     |     | 315 |     |     |     |     | 320 |      |
| GCG | GTG | ACC | AGT | AGG | ATG | GTG | AAG | ACC | TAC | GAG | AAA | CTC | ACC | GAG | ATC | 1008 |
| Ala | Val | Thr | Ser | Arg | Met | Val | Lys | Thr | Tyr | Glu | Lys | Leu | Thr | Glu | Ile |      |
|     |     |     |     | 325 |     |     |     |     | 330 |     |     |     |     | 335 |     |      |
| ATC | CCC | AAG | TCA | GCC | GTG | GGG | GAG | CTG | TCT | GAG | GAC | TCC | AGC | AAT | GTG | 1056 |
| Ile | Pro | Lys | Ser | Ala | Val | Gly | Glu | Leu | Ser | Glu | Asp | Ser | Ser | Asn | Val |      |
|     |     |     | 340 |     |     |     |     | 345 |     |     |     |     | 350 |     |     |      |
| GTC | CAT | CTC | ATT | AAG | AAT | GCT | TAC | AAT | AAA | CTC | TCC | TCC | AGG | GTC | TTC | 1104 |
| Val | His | Leu | Ile | Lys | Asn | Ala | Tyr | Asn | Lys | Leu | Ser | Ser | Arg | Val | Phe |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 355 |     |     |     |     | 360 |     |     |     |     |     | 365 |     |     |      |
| CTG | GAT | CAC | AAC | GCC | CTC | CCC | GAC | ACC | CTG | AAA | GTC | ACC | TAC | GAC | TCC | 1152 |
| Leu | Asp | His | Asn | Ala | Leu | Pro | Asp | Thr | Leu | Lys | Val | Thr | Tyr | Asp | Ser |      |
|     | 370 |     |     |     | 375 |     |     |     |     | 380 |     |     |     |     |     |      |
| TTC | TGC | AGC | AAT | GGA | GTG | ACG | CAC | AGG | AAC | CAG | CCC | AGA | GGT | GAC | TGT | 1200 |
| Phe | Cys | Ser | Asn | Gly | Val | Thr | His | Arg | Asn | Gln | Pro | Arg | Gly | Asp | Cys |      |
| 385 |     |     |     |     | 390 |     |     |     | 395 |     |     |     |     |     | 400 |      |
| GAT | GGC | GTG | CAG | ATC | AAT | GTC | CCG | ATC | ACC | TTC | CAG | GTG | AAG | GTC | ACG | 1248 |
| Asp | Gly | Val | Gln | Ile | Asn | Val | Pro | Ile | Thr | Phe | Gln | Val | Lys | Val | Thr |      |
|     |     |     |     | 405 |     |     |     |     | 410 |     |     |     |     | 415 |     |      |
| GCC | ACA | GAG | TGC | ATC | CAG | GAG | CAG | TCG | TTT | GTC | ATC | CGG | GCG | CTG | GGC | 1296 |
| Ala | Thr | Glu | Cys | Ile | Gln | Glu | Gln | Ser | Phe | Val | Ile | Arg | Ala | Leu | Gly |      |
|     |     |     | 420 |     |     |     |     | 425 |     |     |     |     |     | 430 |     |      |
| TTC | ACG | GAC | ATA | GTG | ACC | GTG | CAG | GTT | CTT | CCC | CAG | TGT | GAG | TGC | CGG | 1344 |
| Phe | Thr | Asp | Ile | Val | Thr | Val | Gln | Val | Leu | Pro | Gln | Cys | Glu | Cys | Arg |      |
|     |     |     | 435 |     |     |     |     | 440 |     |     |     |     | 445 |     |     |      |
| TGC | CGG | GAC | CAG | AGC | AGA | GAC | CGC | AGC | CTC | TGC | CAT | GGC | AAG | GGC | TTC | 1392 |
| Cys | Arg | Asp | Gln | Ser | Arg | Asp | Arg | Ser | Leu | Cys | His | Gly | Lys | Gly | Phe |      |
|     | 450 |     |     |     |     | 455 |     |     |     |     |     | 460 |     |     |     |      |
| TTG | GAG | TGC | GGC | ATC | TGC | AGG | TGT | GAC | ACT | GGC | TAC | ATT | GGG | AAA | AAC | 1440 |
| Leu | Glu | Cys | Gly | Ile | Cys | Arg | Cys | Asp | Thr | Gly | Tyr | Ile | Gly | Lys | Asn |      |
| 465 |     |     |     |     | 470 |     |     |     |     | 475 |     |     |     |     | 480 |      |
| TGT | GAG | TGC | CAG | ACA | CAG | GGC | CGG | AGC | AGC | CAG | GAG | CTG | GAA | GGA | AGC | 1488 |
| Cys | Glu | Cys | Gln | Thr | Gln | Gly | Arg | Ser | Ser | Gln | Glu | Leu | Glu | Gly | Ser |      |
|     |     |     |     | 485 |     |     |     |     | 490 |     |     |     |     | 495 |     |      |
| TGC | CGG | AAG | GAC | AAC | AAC | TCC | ATC | ATC | TGC | TCA | GGG | CTG | GGG | GAC | TGT | 1536 |
| Cys | Arg | Lys | Asp | Asn | Asn | Ser | Ile | Ile | Cys | Ser | Gly | Leu | Gly | Asp | Cys |      |
|     |     |     | 500 |     |     |     |     | 505 |     |     |     |     | 510 |     |     |      |
| GTC | TGC | GGG | CAG | TGC | CTG | TGC | CAC | ACC | AGC | GAC | GTC | CCC | GGC | AAG | CTG | 1584 |
| Val | Cys | Gly | Gln | Cys | Leu | Cys | His | Thr | Ser | Asp | Val | Pro | Gly | Lys | Leu |      |
|     |     | 515 |     |     |     |     | 520 |     |     |     |     | 525 |     |     |     |      |
| ATA | TAC | GGG | CAG | TAC | TGC | GAG | TGT | GAC | ACC | ATC | AAC | TGT | GAG | CGC | TAC | 1632 |
| Ile | Tyr | Gly | Gln | Tyr | Cys | Glu | Cys | Asp | Thr | Ile | Asn | Cys | Glu | Arg | Tyr |      |
|     | 530 |     |     |     |     | 535 |     |     |     |     | 540 |     |     |     |     |      |
| AAC | GGC | CAG | GTC | TGC | GGC | GGC | CCG | GGG | AGG | GGG | CTC | TGC | TTC | TGC | GGG | 1680 |
| Asn | Gly | Gln | Val | Cys | Gly | Gly | Pro | Gly | Arg | Gly | Leu | Cys | Phe | Cys | Gly |      |
| 545 |     |     |     |     | 550 |     |     |     |     | 555 |     |     |     |     | 560 |      |
| AAG | TGC | CGC | TGC | CAC | CCG | GGC | TTT | GAG | GGC | TCA | GCG | TGC | CAG | TGC | GAG | 1728 |
| Lys | Cys | Arg | Cys | His | Pro | Gly | Phe | Glu | Gly | Ser | Ala | Cys | Gln | Cys | Glu |      |
|     |     |     |     | 565 |     |     |     |     | 570 |     |     |     |     | 575 |     |      |
| AGG | ACC | ACT | GAG | GGC | TGC | CTG | AAC | CCG | CGG | CGT | GTT | GAG | TGT | AGT | GGT | 1776 |
| Arg | Thr | Thr | Glu | Gly | Cys | Leu | Asn | Pro | Arg | Arg | Val | Glu | Cys | Ser | Gly |      |
|     |     |     | 580 |     |     |     |     | 585 |     |     |     |     | 590 |     |     |      |
| CGT | GGC | CGG | TGC | CGC | TGC | AAC | GTA | TGC | GAG | TGC | CAT | TCA | GGC | TAC | CAG | 1824 |
| Arg | Gly | Arg | Cys | Arg | Cys | Asn | Val | Cys | Glu | Cys | His | Ser | Gly | Tyr | Gln |      |
|     |     | 595 |     |     |     |     | 600 |     |     |     |     | 605 |     |     |     |      |
| CTG | CCT | CTG | TGC | CAG | GAG | TGC | CCC | GGC | TGC | CCC | TCA | CCC | TGT | GGC | AAG | 1872 |
| Leu | Pro | Leu | Cys | Gln | Glu | Cys | Pro | Gly | Cys | Pro | Ser | Pro | Cys | Gly | Lys |      |
|     | 610 |     |     |     |     | 615 |     |     |     |     | 620 |     |     |     |     |      |
| TAC | ATC | TCC | TGC | GCC | GAG | TGC | CTG | AAG | TTC | GAA | AAG | GGC | CCC | TTT | GGG | 1920 |
| Tyr | Ile | Ser | Cys | Ala | Glu | Cys | Leu | Lys | Phe | Glu | Lys | Gly | Pro | Phe | Gly |      |
| 625 |     |     |     |     | 630 |     |     |     |     | 635 |     |     |     |     | 640 |      |
| AAG | AAC | TGC | AGC | GCG | GCG | TGT | CCG | GGC | CTG | CAG | CTG | TCG | AAC | AAC | CCC | 1968 |
| Lys | Asn | Cys | Ser | Ala | Ala | Cys | Pro | Gly | Leu | Gln | Leu | Ser | Asn | Asn | Pro |      |
|     |     |     |     | 645 |     |     |     |     | 650 |     |     |     |     | 655 |     |      |
| GTG | AAG | GGC | AGG | ACC | TGC | AAG | GAG | AGG | GAC | TCA | GAG | GGC | TGC | TGG | GTG | 2016 |
| Val | Lys | Gly | Arg | Thr | Cys | Lys | Glu | Arg | Asp | Ser | Glu | Gly | Cys | Trp | Val |      |
|     |     |     | 660 |     |     |     |     | 665 |     |     |     |     | 670 |     |     |      |
| GCC | TAC | ACG | CTG | GAG | CAG | CAG | GAC | GGG | ATG | GAC | CGC | TAC | CTC | ATC | TAT | 2064 |
| Ala | Tyr | Thr | Leu | Glu | Gln | Gln | Asp | Gly | Met | Asp | Arg | Tyr | Leu | Ile | Tyr |      |

|   |   |   |   |   | 675 |   |   |   |   | 680 |   |   |   |   | 685 |   |   |
|---|---|---|---|---|---|---|---|---|---|---|---|---|---|---|---|---|---|

```
        GTG  GAT  GAG  AGC  CGA  GAG  TGT  GTG  GCA  GGC  CCC  AAC  ATC  GCC  GCC  ATC               2112
        Val  Asp  Glu  Ser  Arg  Glu  Cys  Val  Ala  Gly  Pro  Asn  Ile  Ala  Ala  Ile
             690                      695                      700

GTC  GGG  GGC  ACC  GTG  GCA  GGC  ATC  GTG  CTG  ATC  GGC  ATT  CTC  CTG  CTG               2160
        Val  Gly  Gly  Thr  Val  Ala  Gly  Ile  Val  Leu  Ile  Gly  Ile  Leu  Leu  Leu
        705                      710                      715                      720

GTC  ATC  TGG  AAG  GCT  CTG  ATC  CAC  CTG  AGC  GAC  CTC  CGG  GAG  TAC  AGG               2208
        Val  Ile  Trp  Lys  Ala  Leu  Ile  His  Leu  Ser  Asp  Leu  Arg  Glu  Tyr  Arg
                            725                      730                      735

CGC  TTT  GAG  AAG  GAG  AAG  CTC  AAG  TCC  CAG  TGG  AAC  AAT  GAT  AAT  CCC               2256
        Arg  Phe  Glu  Lys  Glu  Lys  Leu  Lys  Ser  Gln  Trp  Asn  Asn  Asp  Asn  Pro
                       740                      745                      750

CTT  TTC  AAG  AGC  GCC  ACC  ACG  ACG  GTC  ATG  AAC  CCC  AAG  TTT  GCT  GAG               2304
        Leu  Phe  Lys  Ser  Ala  Thr  Thr  Thr  Val  Met  Asn  Pro  Lys  Phe  Ala  Glu
                  755                      760                      765

AGT  TAG                                                                                      2310
        Ser
```

( 2 ) INFORMATION FOR SEQ ID NO:42:

( i ) SEQUENCE CHARACTERISTICS:
( A ) LENGTH: 1170 amino acids
( B ) TYPE: amino acid
( D ) TOPOLOGY: linear ( i i ) MOLECULE TYPE: protein ( v ) FRAGMENT TYPE: internal ( x i ) SEQUENCE DESCRIPTION: SEQ ID NO:42:

```
Met  Lys  Asp  Ser  Cys  Ile  Thr  Val  Met  Ala  Met  Ala  Leu  Leu  Ser  Gly
  1             5                        10                        15

Phe  Phe  Phe  Phe  Ala  Pro  Ala  Ser  Ser  Tyr  Asn  Leu  Asp  Val  Arg  Gly
                20                       25                        30

Ala  Arg  Ser  Phe  Ser  Pro  Pro  Arg  Ala  Gly  Arg  His  Phe  Gly  Tyr  Arg
           35                       40                        45

Val  Leu  Gln  Val  Gly  Asn  Gly  Val  Ile  Val  Gly  Ala  Pro  Gly  Glu  Gly
      50                       55                        60

Asn  Ser  Thr  Gly  Ser  Leu  Tyr  Gln  Cys  Gln  Ser  Gly  Thr  Gly  His  Cys
 65                       70                        75                        80

Leu  Pro  Val  Thr  Leu  Arg  Gly  Ser  Asn  Tyr  Thr  Ser  Lys  Tyr  Leu  Gly
                85                       90                        95

Met  Thr  Leu  Ala  Thr  Asp  Pro  Thr  Asp  Gly  Ser  Ile  Leu  Ala  Cys  Asp
               100                      105                       110

Pro  Gly  Leu  Ser  Arg  Thr  Cys  Asp  Gln  Asn  Thr  Tyr  Leu  Ser  Gly  Leu
              115                      120                       125

Cys  Tyr  Leu  Phe  Arg  Gln  Asn  Leu  Gln  Gly  Pro  Met  Leu  Gln  Gly  Arg
     130                      135                      140

Pro  Gly  Phe  Gln  Glu  Cys  Ile  Lys  Gly  Asn  Val  Asp  Leu  Val  Phe  Leu
145                      150                      155                      160

Phe  Asp  Gly  Ser  Met  Ser  Leu  Gln  Pro  Asp  Glu  Phe  Gln  Lys  Ile  Leu
                    165                      170                      175

Asp  Phe  Met  Lys  Asp  Val  Met  Lys  Lys  Leu  Ser  Asn  Thr  Ser  Tyr  Gln
               180                      185                      190

Phe  Ala  Ala  Val  Gln  Phe  Ser  Thr  Ser  Tyr  Lys  Thr  Glu  Phe  Asp  Phe
          195                      200                      205

Ser  Asp  Tyr  Val  Lys  Trp  Lys  Asp  Pro  Asp  Ala  Leu  Leu  Lys  His  Val
     210                      215                      220
```

```
Lys His Met Leu Leu Leu Thr Asn Thr Phe Gly Ala Ile Asn Tyr Val
225             230                 235                         240

Ala Thr Glu Val Phe Arg Glu Glu Leu Gly Ala Arg Pro Asp Ala Thr
                245                 250                         255

Lys Val Leu Ile Ile Ile Thr Asp Gly Glu Ala Thr Asp Ser Gly Asn
                    260                 265                 270

Ile Asp Ala Ala Lys Asp Ile Ile Arg Tyr Ile Ile Gly Ile Gly Lys
            275                 280                 285

His Phe Gln Thr Lys Glu Ser Gln Glu Thr Leu His Lys Phe Ala Ser
        290                 295                 300

Lys Pro Ala Ser Glu Phe Val Lys Ile Leu Asp Thr Phe Glu Lys Leu
305                 310                 315                     320

Lys Asp Leu Phe Ile Glu Arg Gln Lys Lys Ile Tyr Val Ile Glu Gly
                    325                 330                 335

Thr Ser Lys Gln Asp Leu Thr Ser Phe Asn Met Glu Leu Ser Ser Ser
            340                 345                 350

Gly Ile Ser Ala Asp Leu Ser Arg Gly His Ala Val Val Gly Ala Val
            355                 360                 365

Gly Ala Lys Asp Trp Ala Gly Phe Leu Asp Leu Lys Ala Asp Leu
370                 375                 380

Gln Asp Asp Thr Phe Ile Gly Asn Glu Pro Leu Thr Pro Glu Val Arg
385                 390                 395                     400

Ala Gly Tyr Leu Gly Tyr Thr Val Thr Trp Leu Pro Ser Arg Gln Lys
                405                 410                 415

Thr Ser Leu Leu Ala Ser Gly Ala Pro Arg Tyr Gln His Met Gly Arg
            420                 425                 430

Val Leu Leu Phe Gln Glu Pro Gln Gly Gly His Trp Ser Gln Val
        435                 440                 445

Gln Thr Ile His Gly Thr Gln Ile Gly Ser Tyr Phe Gly Gly Glu Leu
    450                 455                 460

Cys Gly Val Asp Val Asp Gln Asp Gly Glu Thr Glu Leu Leu Leu Ile
465                 470                 475                     480

Gly Ala Pro Leu Phe Tyr Gly Glu Gln Arg Gly Gly Arg Val Phe Ile
                485                 490                 495

Tyr Gln Arg Arg Gln Leu Gly Phe Glu Val Ser Glu Leu Gln Gly
            500                 505                 510

Asp Pro Gly Tyr Pro Leu Gly Arg Phe Gly Glu Ala Ile Thr Ala Leu
        515                 520                 525

Thr Asp Ile Asn Gly Asp Gly Leu Val Asp Val Ala Val Gly Ala Pro
    530                 535                 540

Leu Glu Glu Gln Gly Ala Val Tyr Ile Phe Asn Gly Arg His Gly Gly
545                 550                 555                 560

Leu Ser Pro Gln Pro Ser Gln Arg Ile Glu Gly Thr Gln Val Leu Ser
            565                 570                 575

Gly Ile Gln Trp Phe Gly Arg Ser Ile His Gly Val Lys Asp Leu Glu
            580                 585                 590

Gly Asp Gly Leu Ala Asp Val Ala Val Gly Ala Glu Ser Gln Met Ile
        595                 600                 605

Val Leu Ser Ser Arg Pro Val Asp Met Val Thr Leu Met Ser Phe
        610                 615                 620

Ser Pro Ala Glu Ile Pro Val His Glu Val Glu Ser Ser Tyr Ser Thr
625                 630                 635                     640

Ser Asn Lys Met Lys Glu Gly Val Asn Ile Thr Ile Cys Phe Gln Ile
```

-continued

```
                         645                      650                       655
    Lys  Ser  Leu  Tyr  Pro  Gln  Phe  Gln  Gly  Arg  Leu  Val  Ala  Asn  Leu  Thr
                    660                      665                      670
    Tyr  Thr  Leu  Gln  Leu  Asp  Gly  His  Arg  Thr  Arg  Arg  Gly  Leu  Phe
              675                      680                      685
    Pro  Gly  Gly  Arg  His  Glu  Leu  Arg  Arg  Asn  Ile  Ala  Val  Thr  Thr  Ser
         690                      695                      700
    Met  Ser  Cys  Thr  Asp  Phe  Ser  Phe  His  Phe  Pro  Val  Cys  Val  Gln  Asp
    705                     710                      715                      720
    Leu  Ile  Ser  Pro  Ile  Asn  Val  Ser  Leu  Asn  Phe  Ser  Leu  Trp  Glu  Glu
                         725                      730                      735
    Glu  Gly  Thr  Pro  Arg  Asp  Gln  Arg  Ala  Gln  Gly  Lys  Asp  Ile  Pro  Pro
                   740                      745                      750
    Ile  Leu  Arg  Pro  Ser  Leu  His  Ser  Glu  Thr  Trp  Glu  Ile  Pro  Phe  Glu
                   755                      760                      765
    Lys  Asn  Cys  Gly  Glu  Asp  Lys  Lys  Cys  Glu  Ala  Asn  Leu  Arg  Val  Ser
              770                      775                      780
    Phe  Ser  Pro  Ala  Thr  Ser  Arg  Ala  Leu  Arg  Leu  Thr  Ala  Phe  Ala  Ser
    785                     790                      795                      800
    Leu  Ser  Val  Glu  Leu  Ser  Leu  Ser  Asn  Leu  Glu  Glu  Asp  Ala  Tyr  Trp
                         805                      810                      815
    Val  Gln  Leu  Asp  Leu  His  Phe  Pro  Pro  Gly  Leu  Ser  Phe  Arg  Lys  Val
                   820                      825                      830
    Glu  Met  Leu  Lys  Pro  His  Ser  Gln  Ile  Pro  Val  Ser  Cys  Glu  Glu  Leu
              835                      840                      845
    Pro  Glu  Glu  Ser  Arg  Leu  Leu  Ser  Arg  Ala  Leu  Ser  Cys  Asn  Val  Ser
         850                      855                      860
    Ser  Pro  Ile  Phe  Lys  Ala  Gly  His  Ser  Val  Ala  Leu  Gln  Met  Met  Phe
    865                     870                      875                      880
    Asn  Thr  Leu  Val  Asn  Ser  Ser  Trp  Gly  Asp  Ser  Val  Glu  Leu  His  Ala
                         885                      890                      895
    Asn  Val  Thr  Cys  Asn  Asn  Glu  Asp  Ser  Asp  Leu  Leu  Glu  Asp  Asn  Ser
                   900                      905                      910
    Ala  Thr  Thr  Ile  Ile  Pro  Ile  Leu  Tyr  Pro  Ile  Asn  Ile  Leu  Ile  Gln
              915                      920                      925
    Asp  Gln  Glu  Asp  Ser  Thr  Leu  Tyr  Val  Ser  Phe  Thr  Pro  Lys  Gly  Pro
         930                      935                      940
    Lys  Ile  His  Gln  Val  Lys  His  Met  Tyr  Gln  Val  Arg  Ile  Gln  Pro  Ser
    945                     950                      955                      960
    Ile  His  Asp  His  Asn  Ile  Pro  Thr  Leu  Glu  Ala  Val  Val  Gly  Val  Pro
                         965                      970                      975
    Gln  Pro  Pro  Ser  Glu  Gly  Pro  Ile  Thr  His  Gln  Trp  Ser  Val  Gln  Met
                   980                      985                      990
    Glu  Pro  Pro  Val  Pro  Cys  His  Tyr  Glu  Asp  Leu  Glu  Arg  Leu  Pro  Asp
              995                     1000                     1005
    Ala  Ala  Glu  Pro  Cys  Leu  Pro  Gly  Pro  Leu  Phe  Arg  Cys  Pro  Val  Val
         1010                     1015                     1020
    Phe  Arg  Gln  Glu  Ile  Leu  Val  Gln  Val  Ile  Gly  Thr  Leu  Glu  Leu  Val
    1025                    1030                     1035                     1040
    Gly  Glu  Ile  Glu  Ala  Ser  Ser  Met  Phe  Ser  Leu  Cys  Ser  Ser  Leu  Ser
                         1045                     1050                     1055
    Ile  Ser  Phe  Asn  Ser  Ser  Lys  His  Phe  His  Leu  Tyr  Gly  Ser  Asn  Ala
                   1060                     1065                     1070
```

Ser Leu Ala Gln Val Val Met Lys Val Asp Val Val Tyr Glu Lys Gln
            1075                1080                1085

Met Leu Tyr Leu Tyr Val Leu Ser Gly Ile Gly Gly Leu Leu Leu Leu
            1090                1095                1100

Leu Leu Ile Xaa Ile Val Leu Tyr Lys Val Gly Phe Phe Lys Arg Asn
1105                1110                1115                1120

Leu Lys Glu Lys Met Glu Ala Gly Arg Gly Val Pro Asn Gly Ile Pro
            1125                1130                1135

Ala Glu Asp Ser Glu Gln Leu Ala Ser Gly Gln Glu Ala Gly Asp Pro
            1140                1145                1150

Gly Cys Leu Lys Pro Leu His Glu Lys Asp Ser Glu Ser Gly Gly Gly
            1155                1160                1165

Lys Asp
    1170

( 2 ) INFORMATION FOR SEQ ID NO:43:

( i ) SEQUENCE CHARACTERISTICS:
   ( A ) LENGTH: 1152 amino acids
   ( B ) TYPE: amino acid
   ( D ) TOPOLOGY: linear ( i i ) MOLECULE TYPE: protein ( v ) FRAGMENT TYPE: internal ( x i ) SEQUENCE DESCRIPTION: SEQ ID NO:43:

Met Ala Leu Arg Val Leu Leu Leu Thr Ala Leu Thr Leu Cys His Gly
1               5                   10                  15

Phe Asn Leu Asp Thr Glu Asn Ala Met Thr Phe Gln Glu Asn Ala Arg
            20                  25                  30

Gly Phe Gly Gln Ser Val Val Gln Leu Gln Gly Ser Arg Val Val Val
            35                  40                  45

Gly Ala Pro Gln Glu Ile Val Ala Ala Asn Gln Arg Gly Ser Leu Tyr
        50                  55                  60

Gln Cys Asp Tyr Ser Thr Gly Ser Cys Glu Pro Ile Arg Leu Gln Val
65                  70                  75                  80

Pro Val Glu Ala Val Asn Met Ser Leu Gly Leu Ser Leu Ala Ala Thr
                    85                  90                  95

Thr Ser Pro Pro Gln Leu Leu Ala Cys Gly Pro Thr Val His Gln Thr
            100                 105                 110

Cys Ser Glu Asn Thr Tyr Val Lys Gly Leu Cys Phe Leu Phe Gly Ser
            115                 120                 125

Asn Leu Arg Gln Gln Pro Gln Lys Phe Pro Glu Ala Leu Arg Gly Cys
    130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
            180                 185                 190

Ser Glu Glu Phe Arg Ile His Phe Thr Phe Lys Glu Phe Gln Asn Asn
            195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

```
Ile  Thr  Asn  Gly  Ala  Arg  Lys  Asn  Ala  Phe  Lys  Ile  Leu  Val  Val  Ile
               245                      250                      255

Thr  Asp  Gly  Glu  Lys  Phe  Gly  Asp  Pro  Leu  Gly  Tyr  Glu  Asp  Val  Ile
               260                      265                      270

Pro  Glu  Ala  Asp  Arg  Glu  Gly  Val  Ile  Arg  Tyr  Val  Ile  Gly  Val  Gly
          275                      280                      285

Asp  Ala  Phe  Arg  Ser  Glu  Lys  Ser  Arg  Gln  Glu  Leu  Asn  Thr  Ile  Ala
     290                      295                      300

Ser  Lys  Pro  Pro  Arg  Asp  His  Val  Phe  Gln  Val  Asn  Asn  Phe  Glu  Ala
305                           310                      315                      320

Leu  Lys  Thr  Ile  Gln  Asn  Gln  Leu  Arg  Glu  Lys  Ile  Phe  Ala  Ile  Glu
                    325                      330                           335

Gly  Thr  Gln  Thr  Gly  Ser  Ser  Ser  Phe  Glu  His  Glu  Met  Ser  Gln
                340                      345                      350

Glu  Gly  Phe  Ser  Ala  Ala  Ile  Thr  Ser  Asn  Gly  Pro  Leu  Leu  Ser  Thr
               355                      360                      365

Val  Gly  Ser  Tyr  Asp  Trp  Ala  Gly  Gly  Val  Phe  Leu  Tyr  Thr  Ser  Lys
     370                      375                      380

Glu  Lys  Ser  Thr  Phe  Ile  Asn  Met  Thr  Arg  Val  Asp  Ser  Asp  Met  Asn
385                           390                      395                      400

Asp  Ala  Tyr  Leu  Gly  Tyr  Ala  Ala  Ala  Ile  Ile  Leu  Arg  Asn  Arg  Val
               405                      410                      415

Gln  Ser  Leu  Val  Leu  Gly  Ala  Pro  Arg  Tyr  Gln  His  Ile  Gly  Leu  Val
               420                      425                      430

Ala  Met  Phe  Arg  Gln  Asn  Thr  Gly  Met  Trp  Glu  Ser  Asn  Ala  Asn  Val
          435                      440                      445

Lys  Gly  Thr  Gln  Ile  Gly  Ala  Tyr  Phe  Gly  Ala  Ser  Leu  Cys  Ser  Val
     450                      455                      460

Asp  Val  Asp  Ser  Asn  Gly  Ser  Thr  Asp  Leu  Val  Leu  Ile  Gly  Ala  Pro
465                      470                      475                      480

His  Tyr  Tyr  Glu  Gln  Thr  Arg  Gly  Gly  Gln  Val  Ser  Val  Cys  Pro  Leu
                    485                      490                      495

Pro  Arg  Gly  Arg  Ala  Arg  Trp  Gln  Cys  Asp  Ala  Val  Leu  Tyr  Gly  Glu
               500                      505                      510

Gln  Gly  Gln  Pro  Trp  Gly  Arg  Phe  Gly  Ala  Ala  Leu  Thr  Val  Leu  Gly
          515                      520                      525

Asp  Val  Asn  Gly  Asp  Lys  Leu  Thr  Asp  Val  Ala  Ile  Gly  Ala  Pro  Gly
     530                      535                      540

Glu  Glu  Asp  Asn  Arg  Gly  Ala  Val  Tyr  Leu  Phe  His  Gly  Thr  Ser  Gly
545                      550                      555                      560

Ser  Gly  Ile  Ser  Pro  Ser  His  Ser  Gln  Arg  Ile  Ala  Gly  Ser  Lys  Leu
               565                      570                      575

Ser  Pro  Arg  Leu  Gln  Tyr  Phe  Gly  Gln  Ser  Leu  Ser  Gly  Gly  Gln  Asp
          580                      585                      590

Leu  Thr  Met  Asp  Gly  Leu  Val  Asp  Leu  Thr  Val  Gly  Ala  Gln  Gly  His
          595                      600                      605

Val  Leu  Leu  Leu  Arg  Ser  Gln  Pro  Val  Leu  Arg  Val  Lys  Ala  Ile  Met
     610                      615                      620

Glu  Phe  Asn  Pro  Arg  Glu  Val  Ala  Arg  Asn  Val  Phe  Glu  Cys  Asn  Asp
625                      630                      635                      640

Gln  Val  Val  Lys  Gly  Lys  Glu  Ala  Gly  Glu  Val  Arg  Val  Cys  Leu  His
                    645                      650                      655

Val  Gln  Lys  Ser  Thr  Arg  Asp  Arg  Leu  Arg  Glu  Gly  Gln  Ile  Gln  Ser
               660                      665                      670
```

| | | | | | | | | | | | | | | |
|---|---|---|---|---|---|---|---|---|---|---|---|---|---|---|
| Val | Val | Thr 675 | Tyr | Asp | Leu | Ala 680 | Leu | Asp | Ser | Gly | Arg 685 | Pro | His | Ser | Arg |
| Ala | Val 690 | Phe | Asn | Glu | Thr 695 | Lys | Asn | Ser | Thr | Arg 700 | Arg | Gln | Thr | Gln | Val |
| Leu 705 | Gly | Leu | Thr | Gln | Thr 710 | Cys | Glu | Thr | Leu | Lys 715 | Leu | Gln | Leu | Pro | Asn 720 |
| Cys | Ile | Glu | Asp | Pro 725 | Val | Ser | Pro | Ile | Val 730 | Leu | Arg | Leu | Asn | Phe 735 | Ser |
| Leu | Val | Gly | Thr 740 | Pro | Leu | Ser | Ala | Phe 745 | Gly | Asn | Leu | Arg | Pro 750 | Val | Leu |
| Ala | Glu | Asp 755 | Ala | Gln | Arg | Leu | Phe 760 | Thr | Ala | Leu | Phe | Pro 765 | Phe | Glu | Lys |
| Asn | Cys 770 | Gly | Asn | Asp | Asn | Ile 775 | Cys | Gln | Asp | Asp | Leu 780 | Ser | Ile | Thr | Phe |
| Ser 785 | Phe | Met | Ser | Leu | Asp 790 | Cys | Leu | Val | Val | Gly 795 | Gly | Pro | Arg | Glu | Ser 800 |
| Asn | Val | Thr | Val 805 | Thr | Val | Arg | Asn | Asp 810 | Gly | Glu | Asp | Ser | Tyr 815 | Arg | Thr |
| Gln | Val | Thr | Phe 820 | Phe | Pro | Leu | Asp 825 | Leu | Ser | Tyr | Arg | Lys 830 | Val | Ser |
| Thr | Leu | Gln 835 | Asn | Gln | Arg | Ser | Gln 840 | Arg | Ser | Trp | Arg | Leu 845 | Ala | Cys | Glu |
| Ser | Ala 850 | Ser | Ser | Thr | Glu | Val 855 | Ser | Gly | Ala | Leu | Lys 860 | Ser | Thr | Ser | Cys |
| Ser | Ile 865 | Asn | His | Pro | Ile 870 | Phe | Pro | Glu | Asn | Ser 875 | Glu | Val | Thr | Phe | Asn 880 |
| Ile | Thr | Phe | Asp | Val 885 | Asp | Ser | Lys | Ala | Ser 890 | Leu | Gly | Asn | Lys | Leu 895 | Leu |
| Leu | Lys | Ala | Asn 900 | Val | Thr | Ser | Glu | Asn 905 | Asn | Met | Pro | Arg | Thr 910 | Asn | Lys |
| Thr | Glu | Phe 915 | Gln | Leu | Glu | Leu | Pro 920 | Val | Lys | Tyr | Ala | Val 925 | Tyr | Met | Val |
| Val | Thr 930 | Ser | His | Gly | Val | Ser 935 | Thr | Lys | Tyr | Leu | Asn 940 | Phe | Thr | Ala | Ser |
| Glu 945 | Asn | Thr | Ser | Arg | Val 950 | Met | Gln | His | Gln | Tyr 955 | Gln | Val | Ser | Asn | Leu 960 |
| Gly | Gln | Arg | Ser | Pro 965 | Pro | Ile | Ser | Leu | Val 970 | Phe | Leu | Val | Pro 975 | Val | Arg |
| Leu | Asn | Gln | Thr 980 | Val | Ile | Trp | Asp | Arg 985 | Pro | Gln | Val | Thr | Phe 990 | Ser | Glu |
| Asn | Leu | Ser 995 | Ser | Thr | Cys | His | Thr 1000 | Lys | Glu | Arg | Leu | Pro 1005 | Ser | His | Ser |
| Asp | Phe 1010 | Leu | Ala | Glu | Leu | Arg 1015 | Lys | Ala | Pro | Val | Val 1020 | Asn | Cys | Ser | Ile |
| Ala 1025 | Val | Cys | Gln | Arg | Ile 1030 | Gln | Cys | Asp | Ile | Pro 1035 | Phe | Phe | Gly | Ile | Gln 1040 |
| Glu | Glu | Phe | Asn | Ala 1045 | Thr | Leu | Lys | Gly | Asn 1050 | Leu | Ser | Phe | Asp | Trp 1055 | Tyr |
| Ile | Lys | Thr | Ser 1060 | His | Asn | His | Leu 1065 | Leu | Ile | Val | Ser | Thr 1070 | Ala | Glu | Ile |
| Leu | Phe | Asn 1075 | Asp | Ser | Val | Phe 1080 | Thr | Leu | Leu | Pro | Gly 1085 | Gln | Gly | Ala | Phe |
| Val | Arg | Ser | Gln | Thr | Glu | Thr | Lys | Val | Glu | Pro | Phe | Glu | Val | Pro | Asn |

-continued

```
                        1090                           1095                           1100

Pro  Leu  Pro  Leu  Ile  Val  Gly  Ser  Ser  Val  Gly  Gly  Leu  Leu  Leu  Leu
      1105                           1110                           1115                           1120

Ala  Leu  Ile  Thr  Ala  Ala  Leu  Tyr  Lys  Leu  Gly  Phe  Phe  Lys  Arg  Gln
                             1125                           1130                           1135

Tyr  Lys  Asp  Met  Met  Ser  Glu  Gly  Gly  Pro  Pro  Gly  Ala  Glu  Pro  Gln
                             1140                           1145                           1150
```

( 2 ) INFORMATION FOR SEQ ID NO:44:

( i ) SEQUENCE CHARACTERISTICS:
        ( A ) LENGTH: 1163 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

```
Met  Thr  Arg  Thr  Arg  Ala  Ala  Leu  Leu  Leu  Phe  Thr  Ala  Leu  Ala  Thr
  1                    5                            10                           15

Ser  Leu  Gly  Phe  Asn  Leu  Asp  Thr  Glu  Glu  Leu  Thr  Ala  Phe  Arg  Val
                20                           25                           30

Asp  Ser  Ala  Gly  Phe  Gly  Asp  Ser  Val  Val  Gln  Tyr  Ala  Asn  Ser  Trp
              35                           40                           45

Val  Val  Val  Gly  Ala  Pro  Gln  Lys  Ile  Thr  Ala  Ala  Asn  Gln  Thr  Gly
      50                           55                           60

Gly  Leu  Tyr  Gln  Cys  Gly  Tyr  Ser  Thr  Gly  Ala  Cys  Glu  Pro  Ile  Gly
 65                           70                           75                           80

Leu  Gln  Val  Pro  Pro  Glu  Ala  Val  Asn  Met  Ser  Leu  Gly  Leu  Ser  Leu
                        85                           90                           95

Ala  Ser  Thr  Thr  Ser  Pro  Ser  Gln  Leu  Leu  Ala  Cys  Gly  Pro  Thr  Val
                     100                          105                          110

His  His  Glu  Cys  Gly  Arg  Asn  Met  Tyr  Leu  Thr  Gly  Leu  Cys  Phe  Leu
               115                          120                          125

Leu  Gly  Pro  Thr  Gln  Leu  Thr  Gln  Arg  Leu  Pro  Val  Ser  Arg  Gln  Glu
           130                          135                          140

Cys  Pro  Arg  Gln  Glu  Gln  Asp  Ile  Val  Phe  Leu  Ile  Asp  Gly  Ser  Gly
145                          150                          155                          160

Ser  Ile  Ser  Ser  Arg  Asn  Phe  Ala  Thr  Met  Met  Asn  Phe  Val  Arg  Ala
                     165                          170                          175

Val  Ile  Ser  Gln  Phe  Gln  Arg  Pro  Ser  Thr  Gln  Phe  Ser  Leu  Met  Gln
                180                          185                          190

Phe  Ser  Asn  Lys  Phe  Gln  Thr  His  Phe  Thr  Phe  Glu  Glu  Phe  Arg  Arg
           195                          200                          205

Thr  Ser  Asn  Pro  Leu  Ser  Leu  Leu  Ala  Ser  Val  His  Gln  Leu  Gln  Gly
      210                          215                          220

Phe  Thr  Tyr  Thr  Ala  Thr  Ala  Ile  Gln  Asn  Val  Val  His  Arg  Leu  Phe
225                          230                          235                          240

His  Ala  Ser  Tyr  Gly  Ala  Arg  Arg  Asp  Ala  Thr  Lys  Ile  Leu  Ile  Val
                245                          250                          255

Ile  Thr  Asp  Gly  Lys  Lys  Glu  Gly  Asp  Ser  Leu  Asp  Tyr  Lys  Asp  Val
           260                          265                          270

Ile  Pro  Met  Ala  Asp  Ala  Ala  Gly  Ile  Ile  Arg  Tyr  Ala  Ile  Gly  Val
      275                          280                          285

Gly  Leu  Ala  Phe  Gln  Asn  Arg  Asn  Ser  Trp  Lys  Glu  Leu  Asn  Asp  Ile
     290                          295                          300
```

-continued

| | | | | | | | | | | | | | | |
|---|---|---|---|---|---|---|---|---|---|---|---|---|---|---|
| Ala | Ser | Lys | Pro | Ser | Gln | Glu | His | Ile | Phe | Lys | Val | Glu | Asp | Phe | Asp |
| 305 | | | | 310 | | | | | 315 | | | | | 320 |
| Ala | Leu | Lys | Asp | Ile | Gln | Asn | Gln | Leu | Lys | Glu | Lys | Ile | Phe | Ala | Ile |
| | | | | 325 | | | | 330 | | | | | | 335 |
| Glu | Gly | Thr | Glu | Thr | Thr | Ser | Ser | Ser | Phe | Glu | Leu | Glu | Met | Ala |
| | | | 340 | | | | | 345 | | | | 350 | | |
| Gln | Glu | Gly | Phe | Ser | Ala | Val | Phe | Thr | Pro | Asp | Gly | Pro | Val | Leu | Gly |
| | | 355 | | | | | 360 | | | | | 365 | | | |
| Ala | Val | Gly | Ser | Phe | Thr | Trp | Ser | Gly | Gly | Ala | Phe | Leu | Tyr | Pro | Pro |
| | | 370 | | | | 375 | | | | | 380 | | | | |
| Asn | Met | Ser | Pro | Thr | Phe | Ile | Asn | Met | Ser | Gln | Glu | Asn | Val | Asp | Met |
| 385 | | | | | 390 | | | | 395 | | | | | | 400 |
| Arg | Asp | Ser | Tyr | Leu | Gly | Tyr | Ser | Thr | Glu | Leu | Ala | Leu | Trp | Lys | Gly |
| | | | | 405 | | | | | 410 | | | | | 415 | |
| Val | Gln | Ser | Leu | Val | Leu | Gly | Ala | Pro | Arg | Tyr | Gln | His | Thr | Gly | Lys |
| 420 | | | | | | | | | 425 | | | | 430 | | |
| Ala | Val | Ile | Phe | Thr | Gln | Val | Ser | Arg | Gln | Trp | Arg | Met | Lys | Ala | Glu |
| | | 435 | | | | | 440 | | | | | 445 | | | |
| Val | Thr | Gly | Thr | Gln | Ile | Gly | Ser | Tyr | Phe | Gly | Ala | Ser | Leu | Cys | Ser |
| | 450 | | | | | 455 | | | | | 460 | | | | |
| Val | Asp | Val | Asp | Thr | Asp | Gly | Ser | Thr | Asp | Leu | Val | Leu | Ile | Gly | Ala |
| 465 | | | | | 470 | | | | | 475 | | | | | 480 |
| Pro | His | Tyr | Tyr | Glu | Gln | Thr | Arg | Gly | Gly | Gln | Val | Ser | Val | Cys | Pro |
| | | | | 485 | | | | | 490 | | | | | 495 | |
| Leu | Pro | Arg | Gly | Trp | Arg | Arg | Trp | Trp | Cys | Asp | Ala | Val | Leu | Tyr | Gly |
| | | | 500 | | | | | 505 | | | | | 510 | | |
| Glu | Gln | Gly | His | Pro | Trp | Gly | Arg | Phe | Gly | Ala | Ala | Leu | Thr | Val | Leu |
| | | | 515 | | | | | 520 | | | | | 525 | | |
| Gly | Asp | Val | Asn | Gly | Asp | Lys | Leu | Thr | Asp | Val | Val | Ile | Gly | Ala | Pro |
| | 530 | | | | | 535 | | | | | 540 | | | | |
| Gly | Glu | Glu | Glu | Asn | Arg | Gly | Ala | Val | Tyr | Leu | Phe | His | Gly | Val | Leu |
| 545 | | | | | 550 | | | | | 555 | | | | | 560 |
| Gly | Pro | Ser | Ile | Ser | Pro | Ser | His | Ser | Gln | Arg | Ile | Ala | Gly | Ser | Gln |
| | | | | 565 | | | | | 570 | | | | | 575 | |
| Leu | Ser | Ser | Arg | Leu | Gln | Tyr | Phe | Gly | Gln | Ala | Leu | Ser | Gly | Gly | Gln |
| | | | 580 | | | | | 585 | | | | | 590 | | |
| Asp | Leu | Thr | Gln | Asp | Gly | Leu | Val | Asp | Leu | Ala | Val | Gly | Ala | Arg | Gly |
| | | 595 | | | | 600 | | | | | 605 | | | | |
| Gln | Val | Leu | Leu | Leu | Arg | Thr | Arg | Pro | Val | Leu | Trp | Val | Gly | Val | Ser |
| | 610 | | | | | 615 | | | | | 620 | | | | |
| Met | Gln | Phe | Ile | Pro | Ala | Glu | Ile | Pro | Arg | Ser | Ala | Phe | Glu | Cys | Arg |
| 625 | | | | | 630 | | | | | 635 | | | | | 640 |
| Glu | Gln | Val | Val | Ser | Glu | Gln | Thr | Leu | Val | Gln | Ser | Asn | Ile | Cys | Leu |
| | | | | 645 | | | | | 650 | | | | | 655 | |
| Tyr | Ile | Asp | Lys | Arg | Ser | Lys | Asn | Leu | Leu | Gly | Ser | Arg | Asp | Leu | Gln |
| | | | 660 | | | | | 665 | | | | | 670 | | |
| Ser | Ser | Val | Thr | Leu | Asp | Leu | Ala | Leu | Asp | Pro | Gly | Arg | Leu | Ser | Pro |
| | | 675 | | | | | 680 | | | | | 685 | | | |
| Arg | Ala | Thr | Phe | Gln | Glu | Thr | Lys | Asn | Arg | Ser | Leu | Ser | Arg | Val | Arg |
| | 690 | | | | | 695 | | | | | 700 | | | | |
| Val | Leu | Gly | Leu | Lys | Ala | His | Cys | Glu | Asn | Phe | Asn | Leu | Leu | Leu | Pro |
| 705 | | | | | 710 | | | | | 715 | | | | | 720 |
| Ser | Cys | Val | Glu | Asp | Ser | Val | Thr | Pro | Ile | Thr | Leu | Arg | Leu | Asn | Phe |
| | | | | 725 | | | | | 730 | | | | | 735 | |

Thr Leu Val Gly Lys Pro Leu Leu Ala Phe Arg Asn Leu Arg Pro Met
            740                 745                 750

Leu Ala Ala Leu Ala Gln Arg Tyr Phe Thr Ala Ser Leu Pro Phe Glu
            755                 760                 765

Lys Asn Cys Gly Ala Asp His Ile Cys Gln Asp Asn Leu Gly Ile Ser
            770                 775                 780

Phe Ser Phe Pro Gly Leu Lys Ser Leu Leu Val Gly Ser Asn Leu Glu
785                 790                 795                 800

Leu Asn Ala Glu Val Met Val Trp Asn Asp Gly Glu Asp Ser Tyr Gly
            805                 810                 815

Thr Thr Ile Thr Phe Ser His Pro Ala Gly Leu Ser Tyr Arg Tyr Val
            820                 825                 830

Ala Glu Gly Gln Lys Gln Gly Gln Leu Arg Ser Leu His Leu Thr Cys
            835                 840                 845

Asp Ser Ala Pro Val Gly Ser Gln Gly Thr Trp Ser Thr Ser Cys Arg
            850                 855                 860

Ile Asn His Leu Ile Phe Arg Gly Gly Ala Gln Ile Thr Phe Leu Ala
865                 870                 875                 880

Thr Phe Asp Val Ser Pro Lys Ala Val Leu Gly Asp Arg Leu Leu Leu
                885                 890                 895

Thr Ala Asn Val Ser Ser Glu Asn Thr Pro Arg Thr Ser Lys Thr
            900                 905                 910

Thr Phe Gln Leu Glu Leu Pro Val Lys Tyr Ala Val Tyr Thr Val Val
            915                 920                 925

Ser Ser His Glu Gln Phe Thr Lys Tyr Leu Asn Phe Ser Glu Ser Glu
    930                 935                 940

Glu Lys Glu Ser His Val Ala Met His Arg Tyr Gln Val Asn Asn Leu
945                 950                 955                 960

Gly Gln Arg Asp Leu Pro Val Ser Ile Asn Phe Trp Val Pro Val Glu
            965                 970                 975

Leu Asn Gln Glu Ala Val Trp Met Asp Val Glu Val Ser His Pro Gln
            980                 985                 990

Asn Pro Ser Leu Arg Cys Ser Ser Glu Lys Ile Ala Pro Pro Ala Ser
    995                 1000                1005

Asp Phe Leu Ala His Ile Gln Lys Asn Pro Val Leu Asp Cys Ser Ile
    1010                1015                1020

Ala Gly Cys Leu Arg Phe Arg Cys Asp Val Pro Ser Phe Ser Val Gln
025                 1030                1035                1040

Glu Glu Leu Asp Phe Thr Leu Lys Gly Asn Leu Ser Phe Gly Trp Val
            1045                1050                1055

Arg Gln Ile Leu Gln Lys Lys Val Ser Val Val Ser Val Ala Glu Ile
            1060                1065                1070

Thr Phe Asp Thr Ser Val Tyr Ser Gln Leu Pro Gly Gln Glu Ala Phe
    1075                1080                1085

Met Arg Ala Gln Thr Thr Thr Val Leu Glu Lys Tyr Lys Val His Asn
    1090                1095                1100

Pro Thr Pro Leu Ile Val Gly Ser Ser Ile Gly Gly Leu Leu Leu Leu
1105                1110                1115                1120

Ala Leu Ile Thr Ala Val Leu Tyr Lys Val Gly Phe Phe Lys Arg Gln
                1125                1130                1135

Tyr Lys Glu Met Met Glu Glu Ala Asn Gly Gln Ile Ala Pro Glu Asn
            1140                1145                1150

Gly Thr Gln Thr Pro Ser Pro Pro Ser Glu Lys 1155          1160

(2) INFORMATION FOR SEQ ID NO:45:

(i) SEQUENCE CHARACTERISTICS:
        (A) LENGTH: 769 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:45:

```
Met Leu Gly Leu Arg Pro Pro Leu Leu Ala Leu Val Gly Leu Leu Ser
 1               5                  10                  15
Leu Gly Cys Val Leu Ser Gln Glu Cys Thr Lys Phe Lys Val Ser Ser
                20                  25                  30
Cys Arg Glu Cys Ile Glu Ser Gly Pro Gly Cys Thr Trp Cys Gln Lys
            35                  40                  45
Leu Asn Phe Thr Gly Pro Gly Asp Pro Asp Ser Ile Arg Cys Asp Thr
        50                  55                  60
Arg Pro Gln Leu Leu Met Arg Gly Cys Ala Ala Asp Asp Ile Met Asp
 65                  70                  75                  80
Pro Thr Ser Leu Ala Glu Thr Gln Glu Asp His Asn Gly Gly Gln Lys
                85                  90                  95
Gln Leu Ser Pro Gln Lys Val Thr Leu Tyr Leu Arg Pro Gly Gln Ala
               100                 105                 110
Ala Ala Phe Asn Val Thr Phe Arg Arg Ala Lys Gly Tyr Pro Ile Asp
           115                 120                 125
Leu Tyr Tyr Leu Met Asp Leu Ser Tyr Ser Met Leu Asp Asp Leu Arg
       130                 135                 140
Asn Val Lys Lys Leu Gly Gly Asp Leu Leu Arg Ala Leu Asn Glu Ile
145                 150                 155                 160
Thr Glu Ser Gly Arg Ile Gly Phe Gly Ser Phe Val Asp Lys Thr Val
               165                 170                 175
Leu Pro Phe Val Asn Thr His Pro Asp Lys Leu Arg Asn Pro Cys Pro
           180                 185                 190
Asn Lys Glu Lys Glu Cys Gln Pro Pro Phe Ala Phe Arg His Val Leu
       195                 200                 205
Lys Leu Thr Asn Asn Ser Asn Gln Phe Gln Thr Glu Val Gly Lys Gln
       210                 215                 220
Leu Ile Ser Gly Asn Leu Asp Ala Pro Glu Gly Gly Leu Asp Ala Met
225                 230                 235                 240
Met Gln Val Ala Ala Cys Pro Glu Glu Ile Gly Trp Arg Asn Val Thr
               245                 250                 255
Arg Leu Leu Val Phe Ala Thr Asp Asp Gly Phe His Phe Ala Gly Asp
           260                 265                 270
Gly Lys Leu Gly Ala Ile Leu Thr Pro Asn Asp Gly Arg Cys His Leu
       275                 280                 285
Glu Asp Asn Leu Tyr Lys Arg Ser Asn Glu Phe Asp Tyr Pro Ser Val
       290                 295                 300
Gly Gln Leu Ala His Lys Leu Ala Glu Asn Asn Ile Gln Pro Ile Phe
305                 310                 315                 320
Ala Val Thr Ser Arg Met Val Lys Thr Tyr Glu Lys Leu Thr Glu Ile
               325                 330                 335
Ile Pro Lys Ser Ala Val Gly Glu Leu Ser Glu Asp Ser Ser Asn Val
```

|   |   |   | 340 |   |   |   | 345 |   |   |   | 350 |   |   |
|---|---|---|---|---|---|---|---|---|---|---|---|---|---|
| Val | His | Leu 355 | Ile | Lys | Asn | Ala | Tyr 360 | Asn | Lys | Leu | Ser | Ser 365 | Arg | Val | Phe |
| Leu | Asp 370 | His | Asn | Ala | Leu | Pro 375 | Asp | Thr | Leu | Lys | Val 380 | Thr | Tyr | Asp | Ser |
| Phe 385 | Cys | Ser | Asn | Gly | Val 390 | Thr | His | Arg | Asn | Gln 395 | Pro | Arg | Gly | Asp | Cys 400 |
| Asp | Gly | Val | Gln | Ile 405 | Asn | Val | Pro | Ile | Thr 410 | Phe | Gln | Val | Lys | Val 415 | Thr |
| Ala | Thr | Glu | Cys 420 | Ile | Gln | Glu | Gln | Ser 425 | Phe | Val | Ile | Arg | Ala 430 | Leu | Gly |
| Phe | Thr | Asp 435 | Ile | Val | Thr | Val | Gln 440 | Val | Leu | Pro | Gln | Cys 445 | Glu | Cys | Arg |
| Cys | Arg 450 | Asp | Gln | Ser | Arg | Asp 455 | Arg | Ser | Leu | Cys | His 460 | Gly | Lys | Gly | Phe |
| Leu 465 | Glu | Cys | Gly | Ile | Cys 470 | Arg | Cys | Asp | Thr | Gly 475 | Tyr | Ile | Gly | Lys | Asn 480 |
| Cys | Glu | Cys | Gln | Thr 485 | Gln | Gly | Arg | Ser | Ser 490 | Gln | Glu | Leu | Glu | Gly 495 | Ser |
| Cys | Arg | Lys | Asp 500 | Asn | Asn | Ser | Ile | Ile 505 | Cys | Ser | Gly | Leu | Gly 510 | Asp | Cys |
| Val | Cys | Gly 515 | Gln | Cys | Leu | Cys | His 520 | Thr | Ser | Asp | Val | Pro 525 | Gly | Lys | Leu |
| Ile | Tyr 530 | Gly | Gln | Tyr | Cys | Glu 535 | Cys | Asp | Thr | Ile | Asn 540 | Cys | Glu | Arg | Tyr |
| Asn 545 | Gly | Gln | Val | Cys | Gly 550 | Gly | Pro | Gly | Arg | Gly 555 | Leu | Cys | Phe | Cys | Gly 560 |
| Lys | Cys | Arg | Cys | His 565 | Pro | Gly | Phe | Glu | Gly 570 | Ser | Ala | Cys | Gln | Cys 575 | Glu |
| Arg | Thr | Thr | Glu 580 | Gly | Cys | Leu | Asn | Pro 585 | Arg | Arg | Val | Glu | Cys 590 | Ser | Gly |
| Arg | Gly | Arg 595 | Cys | Arg | Cys | Asn | Val 600 | Cys | Glu | Cys | His | Ser 605 | Gly | Tyr | Gln |
| Leu | Pro 610 | Leu | Cys | Gln | Glu | Cys 615 | Pro | Gly | Cys | Pro | Ser 620 | Pro | Cys | Gly | Lys |
| Tyr 625 | Ile | Ser | Cys | Ala | Glu 630 | Cys | Leu | Lys | Phe | Glu 635 | Lys | Gly | Pro | Phe | Gly 640 |
| Lys | Asn | Cys | Ser | Ala 645 | Ala | Cys | Pro | Gly | Leu 650 | Gln | Leu | Ser | Asn | Asn 655 | Pro |
| Val | Lys | Gly | Arg 660 | Thr | Cys | Lys | Glu | Arg 665 | Asp | Ser | Glu | Gly | Cys 670 | Trp | Val |
| Ala | Tyr | Thr 675 | Leu | Glu | Gln | Gln | Asp 680 | Gly | Met | Asp | Arg | Tyr 685 | Leu | Ile | Tyr |
| Val | Asp 690 | Glu | Ser | Arg | Glu | Cys 695 | Val | Ala | Gly | Pro | Asn 700 | Ile | Ala | Ala | Ile |
| Val 705 | Gly | Gly | Thr | Val | Ala 710 | Gly | Ile | Val | Leu | Ile 715 | Gly | Ile | Leu | Leu | Leu 720 |
| Val | Ile | Trp | Lys | Ala 725 | Leu | Ile | His | Leu | Ser 730 | Asp | Leu | Arg | Glu | Tyr 735 | Arg |
| Arg | Phe | Glu | Lys 740 | Glu | Lys | Leu | Lys | Ser 745 | Gln | Trp | Asn | Asn | Asp 750 | Asn | Pro |
| Leu | Phe | Lys 755 | Ser | Ala | Thr | Thr | Thr 760 | Val | Met | Asn | Pro | Lys 765 | Phe | Ala | Glu |

Ser ( 2 ) INFORMATION FOR SEQ ID NO:46:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:46:

Asp Val Asp Ser Asn Gly Ser Thr Asp
1               5

( 2 ) INFORMATION FOR SEQ ID NO:47:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:47:

Asp Val Asn Gly Asp Lys Leu Thr Asp
1               5

( 2 ) INFORMATION FOR SEQ ID NO:48:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:48:

Asp Leu Thr Met Asp Gly Leu Val Asp
1               5

( 2 ) INFORMATION FOR SEQ ID NO:49:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:49:

Asp Ser Asp Met Asn Asp Ala Tyr Leu
1               5

( 2 ) INFORMATION FOR SEQ ID NO:50:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:50:

Asn Ala Phe Lys Ile Leu Val Val Ile Thr Asp Gly Glu Lys Phe Gly
1               5                   10                  15

Asp Pro Leu Gly Tyr Glu Asp Val Ile Pro Glu Ala Asp Arg Glu Gly
              20                  25                  30

Val ( 2 ) INFORMATION FOR SEQ ID NO:51:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:51:

Asp Gly Glu Lys Phe
 1               5

( 2 ) INFORMATION FOR SEQ ID NO:52:

( i ) SEQUENCE CHARACTERISTICS:
      ( A ) LENGTH: 4704 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:52:

| | | | | | | |
|---|---|---|---|---|---|---|
| GAATTCCTGC | CACTCTTCCT | GCAACGGCCC | AGGAGCTCAG | AGCTCCACAT | CTGACCTTCT | 60 |
| AGTCATGACC | AGGACCAGGG | CAGCACTCCT | CCTGTTCACA | GCCTTAGCAA | CTTCTCTAGG | 120 |
| TTTCAACTTG | GACACAGAGG | AGCTGACAGC | CTTCCGTGTG | GACAGCGCTG | GGTTTGGAGA | 180 |
| CAGCGTGGTC | CAGTATGCCA | ACTCCTGGGT | GGTGGTTGGA | GCCCCCAAA | AGATAACAGC | 240 |
| TGCCAACCAA | ACGGGTGGCC | TCTACCAGTG | TGGCTACAGC | ACTGGTGCCT | GTGAGCCCAT | 300 |
| CGGCCTGCAG | GTGCCCCCGG | AGGCCGTGAA | CATGTCCCTG | GGCCTGTCCC | TGGCGTCTAC | 360 |
| CACCAGCCCT | TCCCAGCTGC | TGGCCTGCGG | CCCCACCGTG | CACCACGAGT | GCGGGAGGAA | 420 |
| CATGTACCTC | ACCGGACTCT | GCTTCCTCCT | GGGCCCCACC | CAGCTCACCC | AGAGGCTCCC | 480 |
| GGTGTCCAGG | CAGGAGTGCC | CAAGACAGGA | GCAGGACATT | GTGTTCCTGA | TCGATGGCTC | 540 |
| AGGCAGCATC | TCCTCCCGCA | ACTTTGCCAC | GATGATGAAC | TTCGTGAGAG | CTGTGATAAG | 600 |
| CCAGTTCCAG | AGACCCAGCA | CCCAGTTTTC | CCTGATGCAG | TTCTCCAACA | AATTCCAAAC | 660 |
| ACACTTCACT | TTCGAGGAAT | TCAGGCGCAC | GTCAAACCCC | CTCAGCCTGT | TGGCTTCTGT | 720 |
| TCACCAGCTG | CAAGGGTTTA | CATACACGGC | CACCGCCATC | CAAAATGTCG | TGCACCGATT | 780 |
| GTTCCATGCC | TCATATGGGG | CCCGTAGGGA | TGCCACCAAA | ATTCTCATTG | TCATCACTGA | 840 |
| TGGGAAGAAA | GAAGGCGACA | GCCTGGATTA | TAAGGATGTC | ATCCCCATGG | CTGATGCAGC | 900 |
| AGGCATCATC | CGCTATGCAA | TTGGGGTTGG | ATTAGCTTTT | CAAAACAGAA | ATTCTTGGAA | 960 |
| AGAATTAAAT | GACATTGCAT | CGAAGCCCTC | CCAGGAACAC | ATATTTAAAG | TGGAGGACTT | 1020 |
| TGATGCTCTG | AAAGATATTC | AAAACCAACT | GAAGGAGAAG | ATCTTTGCCA | TTGAGGGTAC | 1080 |
| GGAGACCACA | AGCAGTAGCT | CCTTCGAATT | GGAGATGGCA | CAGGAGGGCT | TCAGCGCTGT | 1140 |
| GTTCACACCT | GATGGCCCCG | TTCTGGGGGC | TGTGGGGAGC | TTCACCTGGT | CTGGAGGTGC | 1200 |
| CTTCCTGTAC | CCCCCAAATA | TGAGCCCTAC | CTTCATCAAC | ATGTCTCAGG | AGAATGTGGA | 1260 |
| CATGAGGGAC | TCTTACCTGG | GTTACTCCAC | CGAGCTGGCC | CTCTGGAAAG | GGTGCAGAG | 1320 |
| CCTGGTCCTG | GGGGCCCCCC | GCTACCAGCA | CACCGGGAAG | GCTGTCATCT | TCACCCAGGT | 1380 |
| GTCCAGGCAA | TGGAGGATGA | AGGCCGAAGT | CACGGGGACT | CAGATCGGCT | CCTACTTCGG | 1440 |
| GGCCTCCCTC | TGCTCCGTGG | ACGTAGACAC | CGACGGCAGC | ACCGACCTGG | TCCTCATCGG | 1500 |

```
GGCCCCCCAT TACTACGAGC AGACCCGAGG GGGCCAGGTG TCTGTGTGTC CCTTGCCCAG    1560
GGGGTGGAGA AGGTGGTGGT GTGATGCTGT TCTCTACGGG GAGCAGGGCC ACCCCTGGGG    1620
TCGCTTTGGG GCGGCTCTGA CAGTGCTGGG GGATGTGAAT GGGGACAAGC TGACAGACGT    1680
GGTCATCGGG GCCCCAGGAG AGGAGGAGAA CCGGGGTGCT GTCTACCTGT TTCACGGAGT    1740
CTTGGGACCC AGCATCAGCC CCTCCCACAG CCAGCGGATC GCGGGCTCCC AGCTCTCCTC    1800
CAGGCTGCAG TATTTTGGGC AGGCACTGAG CGGGGGTCAA GACCTCACCC AGGATGGACT    1860
GGTGGACCTG GCTGTGGGGG CCCGGGGCCA GGTGCTCCTG CTCAGGACCA GACCTGTGCT    1920
CTGGGTGGGG GTGAGCATGC AGTTCATACC TGCCGAGATC CCCAGGTCTG CGTTTGAGTG    1980
TCGGGAGCAG GTGGTCTCTG AGCAGACCCT GGTACAGTCC AACATCTGCC TTTACATTGA    2040
CAAACGTTCT AAGAACCTGC TTGGGAGCCG TGACCTCCAA AGCTCTGTGA CCTTGGACCT    2100
GGCCCTCGAC CCTGGCCGCC TGAGTCCCCG TGCCACCTTC CAGGAAACAA AGAACCGGAG    2160
TCTGAGCCGA GTCCGAGTCC TCGGGCTGAA GGCACACTGT GAAAACTTCA ACCTGCTGCT    2220
CCCGAGCTGC GTGGAGGACT CTGTGACCCC CATTACCTTG CGTCTGAACT TCACGCTGGT    2280
GGGCAAGCCC CTCCTTGCCT TCAGAAACCT GCGGCCTATG CTGGCCGCAC TGGCTCAGAG    2340
ATACTTCACG GCCTCCCTAC CCTTTGAGAA GAACTGTGGA GCCGACCATA TCTGCCAGGA    2400
CAATCTCGGC ATCTCCTTCA GCTTCCCAGG CTTGAAGTCC CTGCTGGTGG GGAGTAACCT    2460
GGAGCTGAAC GCAGAAGTGA TGGTGTGGAA TGACGGGGAA GACTCCTACG GAACCACCAT    2520
CACCTTCTCC CACCCCGCAG GACTGTCCTA CCGCTACGTG GCAGAGGGCC AGAAACAAGG    2580
GCAGCTGCGT TCCCTGCACC TGACATGTGA CAGCGCCCCA GTTGGGAGCC AGGGCACCTG    2640
GAGCACCAGC TGCAGAATCA ACCACCTCAT CTTCCGTGGC GGCGCCCAGA TCACCTTCTT    2700
GGCTACCTTT GACGTCTCCC CCAAGGCTGT CCTGGGAGAC CGGCTGCTTC TGACAGCCAA    2760
TGTGAGCAGT GAGAACAACA CTCCCAGGAC CAGCAAGACC ACCTTCCAGC TGGAGCTCCC    2820
GGTGAAGTAT GCTGTCTACA CTGTGGTTAG CAGCCACGAA CAATTCACCA AATACCTCAA    2880
CTTCTCAGAG TCTGAGGAGA AGGAAAGCCA TGTGGCCATG CACAGATACC AGGTCAATAA    2940
CCTGGGACAG AGGGACCTGC CTGTCAGCAT CAACTTCTGG GTGCCTGTGG AGCTGAACCA    3000
GGAGGCTGTG TGGATGGATG TGGAGGTCTC CCACCCCCAG AACCCATCCC TTCGGTGCTC    3060
CTCAGAGAAA ATCGCACCCC CAGCATCTGA CTTCCTGGCG CACATTCAGA AGAATCCCGT    3120
GCTGGACTGC TCCATTGCTG GCTGCCTGCG GTTCCGCTGT GACGTCCCCT CCTTCAGCGT    3180
CCAGGAGGAG CTGGATTTCA CCCTGAAGGG CAACCTCAGC TTTGGCTGGG TCCGCCAGAT    3240
ATTGCAGAAG AAGGTGTCGG TCGTGAGTGT GGCTGAAATT ACGTTCGACA CATCCGTGTA    3300
CTCCCAGCTT CCAGGACAGG AGGCATTTAT GAGAGCTCAG ACGACAACGG TGCTGGAGAA    3360
GTACAAGGTC CACAACCCCA CCCCCCTCAT CGTAGGCAGC TCCATTGGGG GTCTGTTGCT    3420
GCTGGCACTC ATCACAGCGG TACTGTACAA AGTTGGCTTC TTCAAGCGTC AGTACAAGGA    3480
AATGATGGAG GAGGCAAATG GACAAATTGC CCCAGAAAAC GGGACACAGA CCCCCAGCCC    3540
GCCCAGTGAG AAATGATCCC TCTTTGCCTT GGACTTCTTC TCCCGCGATT TTCCCCACTT    3600
ACTTACCCTC ACCTGTCAGG CTGACGGGGA GGAACCACTG CACCACCGAG AGAGGCTGGG    3660
ATGGGCCTGC TTCCTGTCTT TGGGAGAAAA CGTCTTGCTT GGGAAGGGGC CTTTGTCTTG    3720
TCAAGGTTCC AACTGGAAAC CCTTAGGACA GGGTCCCTGC TGTGTTCCCC AAAAGGACTT    3780
GACTTGCAAT TTCTACCTAG AAATACATGG ACAATACCCC CAGGCCTCAG TCTCCCTTCT    3840
CCCATGAGGC ACGAATGATC TTTCTTTCCT TTCCTTTTTT TTTTTTTCT TTTCTTTTTT    3900
```

| | | | | | |
|---|---|---|---|---|---|
| TTTTTTTTTG | AGACGGAGTC | TCGCTCTGTC | ACCCAGGCTG | GAGTGCAATG | GCGTGATCTC | 3960
| GGCTCGCTGC | AACCTCCGCC | TCCCGGGTTC | AAGTAATTCT | GCTGTCTCAG | CCTCCTGCGT | 4020
| AGCTGGGACT | ACAGGCACAC | GCCACCTCGC | CCGGCCCGAT | CTTTCTAAAA | TACAGTTCTG | 4080
| AATATGCTGC | TCATCCCCAC | CTGTCTTCAA | CAGCTCCCCA | TTACCCTCAG | GACAATGTCT | 4140
| GAACTCTCCA | GCTTCGCGTG | AGAAGTCCCC | TTCCATCCCA | GAGGGTGGGC | TTCAGGGCGC | 4200
| ACAGCATGAG | AGCCTCTGTG | CCCCCATCAC | CCTCGTTTCC | AGTGAATTAG | TGTCATGTCA | 4260
| GCATCAGCTC | AGGGCTTCAT | CGTGGGCTC | TCAGTTCCGA | TTCCCAGGC | TGAATTGGGA | 4320
| GTGAGATGCC | TGCATGCTGG | GTTCTGCACA | GCTGGCCTCC | CGCGGTTGGG | TCAACATTGC | 4380
| TGGCCTGGAA | GGGAGGAGCG | CCCTCTAGGG | AGGGACATGG | CCCCGGTGCG | GCTGCAGCTC | 4440
| ACCAGCCCCA | GGGGCAGAAG | AGACCCAACC | ACTTCCTATT | TTTTGAGGCT | ATGAATATAG | 4500
| TACCTGAAAA | AATGCCAAGC | ACTAGATTAT | TTTTTAAAA | AGCGTACTTT | AAATGTTTGT | 4560
| GTTAATACAC | ATTAAAACAT | CGCACAAAAA | CGATGCATCT | ACCGCTCCTT | GGGAAATAAT | 4620
| CTGAAAGGTC | TAAAAATAAA | AAAGCCTTCT | GTGGAAAAAA | AAAAAAAAAA | AAAAAAAAA | 4680
| AAAAAAAAAA | AAAAAAAAAA | AAAA | | | | 4704

( 2 ) INFORMATION FOR SEQ ID NO:53:

( i ) SEQUENCE CHARACTERISTICS:
        ( A ) LENGTH: 2291 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:53:

| | | | | | |
|---|---|---|---|---|---|
| CTCGCCCTGG | TGGGGCTGCT | CTCCCTCGGG | TGCGTCCTCT | CTCAGGAGTG | CACGAAGTTC | 60
| AAGGTCAGCA | GCTGCCGGGA | ATGCATCGAG | TCGGGGCCCG | GCTGCACCTG | GTGCCAGAAG | 120
| CTGAACTTCA | CAGGGCCGGG | GGATCCTGAC | TCCATTCGCT | GCGACACCCG | GCCACAGCTG | 180
| CTCATGAGGG | GCTGTGCGGC | TGACGACATC | ATGGACCCCA | CAAGCCTCGC | TGAAACCCAG | 240
| GAAGACCACA | ATGGGGGCCA | GAAGCAGCTG | TCCCCACAAA | AAGTGACGCT | TTACCTGCGA | 300
| CCAGGCCAGG | CAGCAGCGTT | CAACGTGACC | TTCCGGCGGG | CCAAGGGCTA | CCCCATCGAC | 360
| CTGTACTATC | TGATGGACCT | CTCCTACTCC | ATGCTTGATG | ACCTCAGGAA | TGTCAAGAAG | 420
| CTAGGTGGCG | ACCTGCTCCG | GGCCCTCAAC | GAGATCACCG | AGTCCGGCCG | CATTGGCTTC | 480
| GGGTCCTTCG | TGGACAAGAC | CGTGCTGCCG | TTCGTGAACA | CGCACCCTGA | TAAGCTGCGA | 540
| AACCCATGCC | CCAACAAGGA | GAAAGAGTGC | CAGCCCCCGT | TTGCCTTCAG | GCACGTGCTG | 600
| AAGCTGACCA | ACAACTCCAA | CCAGTTTCAG | ACCGAGGTCG | GGAAGCAGCT | GATTTCCGGA | 660
| AACCTGGATG | CACCCGAGGG | TGGGCTGGAC | GCCATGATGC | AGGTCGCCGC | CTGCCCGGAG | 720
| GAAATCGGCT | GGCGCAACGT | CACGCGGCTG | CTGGTGTTTG | CCACTGATGA | CGGCTTCCAT | 780
| TTCGCGGGCG | ACGGAAAGCT | GGGCGCCATC | CTGACCCCCA | ACGACGGCCG | CTGTCACCTG | 840
| GAGGACAACT | TGTACAAGAG | GAGCAACGAA | TTCGACTACC | CATCGGTGGG | CCAGCTGGCG | 900
| CACAAGCTGG | CTGAAAACAA | CATCCAGCCC | ATCTTCGCGG | TGACCAGTAG | GATGGTGAAG | 960
| ACCTACGAGA | AACTCACCGA | GATCATCCCC | AAGTCAGCCG | TGGGGGAGCT | GTCTGAGGAC | 1020
| TCCAGCAATG | TGGTCCATCT | CATTAAGAAT | GCTTACAATA | AACTCTCCTC | CAGGGTCTTC | 1080
| CTGGATCACA | ACGCCCTCCC | CGACACCCTG | AAAGTCACCT | ACGACTCCTT | CTGCAGCAAT | 1140
| GGAGTGACGC | ACAGGAACCA | GCCCAGAGGT | GACTGTGATG | GCGTGCAGAT | CAATGTCCCG | 1200

```
ATCACCTTCC  AGGTGAAGGT  CACGGCCACA  GAGTGCATCC  AGGAGCAGTC  GTTTGTCATC    1260

CGGGCGCTGG  GCTTCACGGA  CATAGTGACC  GTGCAGGTCC  TTCCCCAGTG  TGAGTGCCGG    1320

TGCCGGGACC  AGAGCAGAGA  CCGCAGCCTC  TGCCATGGCA  AGGGCTTCTT  GGAGTGCGGC    1380

ATCTGCAGGT  GTGACACTGG  CTACATTGGG  AAAAACTGTG  AGTGCCAGAC  ACAGGGCCGG    1440

AGCAGCCAGG  AGCTGGAAGG  AAGCTGCCGG  AAGGACAACA  ACTCCATCAT  CTGCTCAGGG    1500

CTGGGGGACT  GTGTCTGCGG  GCAGTGCCTG  TGCCACACCA  GCGACGTCCC  CGGCAAGCTG    1560

ATATACGGGC  AGTACTGCGA  GTGTGACACC  ATCAACTGTG  AGCGCTACAA  CGGCCAGGTC    1620

TGCGGCGGCC  CGGGGAGGGG  GCTCTGCTTC  TGCGGGAAGT  GCCGCTGCCA  CCCGGGCTTT    1680

GAGGGCTCAG  CGTGCCAGTG  CGAGAGGACC  ACTGAGGGCT  GCCTGAACCC  GCGGCGTGTT    1740

GAGTGTAGTG  GTCGTGGCCG  GTGCCGCTGC  AACGTATGCG  AGTGCCATTC  AGGCTACCAG    1800

CTGCCTCTGT  GCCAGGAGTG  CCCCGGCTGC  CCCTCACCCT  GTGGCAAGTA  CATCTCCTGC    1860

GCCGAGTGCC  TGAAGTTCGA  AAAGGGCCCC  TTTGGGAAGA  ACTGCAGCGC  GGCGTGTCCG    1920

GGCCTGCAGC  TGTCGAACAA  CCCCGTGAAG  GGCAGGACCT  GCAAGGAGAG  GGACTCAGAG    1980

GGCTGCTGGG  TGGCCTACAC  GCTGGAGCAG  CAGGACGGGA  TGGACCGCTA  CCTCATCTAT    2040

GTGGATGAGA  GCCGAGAGTG  TGTGGCAGGC  CCCAACATCG  CCGCCATCGT  CGGGGGCACC    2100

GTGGCAGGCA  TCGTGCTGAT  CGGCATTCTC  CTGCTGGTCA  TCTGGAAGGC  TCTGATCCAC    2160

CTGAGCGACC  TCCGGGAGTA  CAGGCGCTTT  GAGAAGGAGA  AGCTCAAGTC  CCAGTGGAAC    2220

AATGATAATC  CCCTTTTCAA  GAGCGCCACC  ACGACGGTCA  TGAACCCCAA  GTTTGCTGAG    2280

AGTTAGGAGC  A                                                             2291
```